(12) United States Patent
Rueger et al.

(10) Patent No.: US 6,949,505 B1
(45) Date of Patent: Sep. 27, 2005

(54) MORPHOGEN-INDUCED DENDRITIC GROWTH

(75) Inventors: David C. Rueger, Hopkinton, MA (US); Kuber T. Sampath, Medway, MA (US); John E. Smart, Weston, MA (US); Hermann Oppermann, Medway, MA (US); Engin Ozkaynak, Milford, MA (US); Charles M. Cohen, Weston, MA (US); Dennis Higgins, Amherst, NY (US)

(73) Assignees: Curis, Inc., Cambridge, MA (US); The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 08/292,782

(22) Filed: Aug. 18, 1994

Related U.S. Application Data

(63) Continuation-in-part of application No. 08/260,675, filed on Jun. 16, 1994, now Pat. No. 6,800,603, which is a continuation of application No. 08/126,100, filed on Sep. 23, 1993, now abandoned, which is a continuation of application No. 07/922,813, filed on Jul. 31, 1992, now abandoned, which is a continuation-in-part of application No. 07/752,764, filed on Aug. 30, 1991, now abandoned, which is a continuation-in-part of application No. 07/667,274, filed on Mar. 11, 1991, now abandoned, application No. 08/292,782, which is a continuation-in-part of application No. 07/971,091, filed on Nov. 3, 1992, now abandoned, which is a continuation-in-part of application No. 07/752,764, filed on Aug. 30, 1991, now abandoned, which is a continuation-in-part of application No. 07/667,274, filed on Mar. 11, 1991, now abandoned, application No. 08/292,782, which is a continuation-in-part of application No. 07/938,336, filed on Aug. 28, 1992, now abandoned, and a continuation-in-part of application No. 07/938,337, filed on Aug. 28, 1992, now abandoned, said application No. 07/938,336, is a continuation-in-part of application No. 07/667,274, filed on Mar. 11, 1991, now abandoned, said application No. 07/938,337, is a continuation-in-part of application No. 07/667,274, filed on Mar. 11, 1991, now abandoned, application No. 08/292,782, which is a continuation-in-part of application No. 07/938,021, filed on Aug. 28, 1992, now abandoned, which is a continuation-in-part of application No. 07/752,861, filed on Aug. 30, 1991, now abandoned, which is a continuation-in-part of application No. 07/667,274, filed on Mar. 11, 1991, now abandoned, application No. 08/292,782, which is a continuation-in-part of application No. 07/752,764, filed on Aug. 30, 1991, now abandoned.

(51) Int. Cl.[7] ............................................. A01N 37/18
(52) U.S. Cl. ........................... 514/2; 530/300; 530/350
(58) Field of Search ............................. 514/2, 21, 12; 530/300, 350; 424/184.1, 198.1, 570, 484; 435/240.2

(56) References Cited

U.S. PATENT DOCUMENTS

| 4,801,575 | A | 1/1989 | Pardridge ...................... 514/4 |
|---|---|---|---|
| 4,877,864 | A | 10/1989 | Wang et al. .................. 514/12 |
| 4,968,590 | A | 11/1990 | Kuberasampath et al. ... 530/326 |
| 4,975,526 | A | 12/1990 | Kuberasampath et al. ... 530/350 |
| 5,011,486 | A | 4/1991 | Aebischer et al. ........... 606/152 |
| 5,011,691 | A | 4/1991 | Oppermann et al. ......... 424/423 |
| 5,013,649 | A | 5/1991 | Wang et al. ................ 435/69.1 |
| 5,091,513 | A | 2/1992 | Huston et al. ............ 530/387.3 |
| 5,093,317 | A | 3/1992 | Lewis et al. ................... 514/12 |
| 5,106,626 | A | 4/1992 | Parsons et al. .............. 424/423 |
| 5,108,753 | A | 4/1992 | Kuberasampath et al. ... 424/422 |
| 5,141,905 | A | 8/1992 | Rosen et al. ................ 435/69.1 |

FOREIGN PATENT DOCUMENTS

| EP | 0148155 | 1/1985 |
|---|---|---|
| WO | WO92/00382 | 1/1992 |
| WO | WO 92/15323 | 9/1992 |

OTHER PUBLICATIONS

Lein et al. Neuron 15 (1995) 597–604.*
Jackowski British J. of Neurosurgery 9 (1995) 303–317.*
Skolnick et al., Trends in Biotech., 18(1):34–39, 2000.*
Zheng et al., Pathology Research and Practice 1992 188(8):1104–21.*
Kawamata et al., Neuroreport May 11, 1998, 9(7):1441–5.*
Ren et al., Neuropharm., Mar. 3, 2000, 39(5):860–65.*
Hulley et al., J. of Neurosci. Res., Jul. 15, 1998, 53(2):129–34.*
Chen et al., J. of Neurobiol., Feb. 15, 1999, 38(3):428–39.*
Chao et al., Neurobiol. Of aging, Jan.–Feb., 2003, 24(1):105–16.*
Ditlevsen et al., J. of Neurochem., Feb., 2003, 84(3):546–56.*
Basler et al. (1993), "Control of Cell Pattern in the Neural Tube: Regulation of Cell Differentiation by dorsalin–1, a Novel TGFB Family Member," 73 *Cell* 687–702.

* cited by examiner

*Primary Examiner*—Sharon L. Turner
(74) *Attorney, Agent, or Firm*—Fish & Neave IP Group, Ropes & Gray LLP

(57) ABSTRACT

Disclosed are methods and compositions for maintaining neural pathways in a mammal including: enhancing survival of neurons at risk of dying; inducing cellular repair of damaged neurons and neural pathways; stimulating neurons to maintain their differentiated phenotype; and promoting dendritic outgrowth, including maintaining dendritic arbors and regenerating dendritic architecture. In one embodiment, the invention provides means for stimulating CAM expression in neurons. The invention also provides means for evaluating the status of nerve tissue, including means for detecting and monitoring neuropathies in a mammal. The methods, devices and compositions include a morphogen or morphogen-stimulating agent provided to the mammal in a therapeutically effective concentration. In another embodiment, the invention provides methods and compositions which include a morphogen or morphogen-stimulating agent, and a nerve trophic factor or nerve trophic factor-stimulating agent at concentrations effective for stimulating dendrite outgrowth. The morphogen and the nerve trophic factor can be admixed in combination.

18 Claims, 6 Drawing Sheets

```
                           SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..97
        (D) OTHER INFORMATION: /label= GENERIC-SEQ1
            /note= "WHEREIN EACH XAA INDEPENDENTLY INDICATES
            ONE OF THE 20 NATURALLY-OCCURING L-ISOMER, A-AMINO
            ACIDS, OR A DERIVATIVE THEREOF."

(xi) SEQUENCE DESCRIPTION: SEQ ID NO:1:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Cys Xaa Xaa Xaa Cys Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Cys Cys Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Cys Xaa Cys
                85                  90                  95

Xaa
```

(2) INFORMATION FOR SEQ ID NO:2:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..97
        (D) OTHER INFORMATION: /label= GENERIC-SEQ2
            /note= "WHEREIN EACH XAA INDEPENDENTLY INDICATES
            ONE OF THE 20 NATURALLY OCCURING L-ISOMER A-AMINO
            ACIDS, OR A DERIVATIVE THEREOF."

(xi) SEQUENCE DESCRIPTION: SEQ ID NO:2:

```
Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Cys Xaa Xaa Xaa Cys Xaa Xaa Xaa
            20                  25                  30

Xaa Xaa Xaa Cys Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Cys Cys Xaa Xaa
        50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Cys Xaa Cys
                85                  90                  95

Xaa
```

(2) INFORMATION FOR SEQ ID NO:3:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..97
        (D) OTHER INFORMATION: /label= GENERIC-SEQ3
            /note= "WHEREIN EACH XAA IS INDEPENDENTLY SELECTED
            FROM A GROUP OF ONE OR MORE SPECIFIED AMINO ACIDS
            AS DEFINED IN THE SPECIFICATION."

(xi) SEQUENCE DESCRIPTION: SEQ ID NO:3:

```
Leu Tyr Val Xaa Phe Xaa Xaa Xaa Gly Trp Xaa Xaa Trp Xaa Xaa Ala
 1               5                  10                  15

Pro Xaa Gly Xaa Xaa Ala Xaa Tyr Cys Xaa Gly Xaa Cys Xaa Xaa Pro
            20                  25                  30

Xaa Xaa Xaa Xaa Xaa Xaa Xaa Asn His Ala Xaa Xaa Xaa Xaa Leu
        35                  40                  45

Xaa Xaa Xaa Xaa Xaa Xaa Xaa Xaa Xaa Xaa Xaa Cys Cys Xaa Pro
        50                  55                  60

Xaa Xaa Xaa Xaa Xaa Xaa Xaa Leu Xaa Xaa Xaa Xaa Xaa Xaa Xaa
65                  70                  75                  80

Val Xaa Leu Xaa Xaa Xaa Xaa Xaa Met Xaa Val Xaa Xaa Cys Gly Cys
```

```
                    85                  90                  95
Xaa
```

(2) INFORMATION FOR SEQ ID NO:4:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /label= GENERIC-SEQ4
            /note= "WHEREIN EACH XAA IS INDEPENDENTLY SELECTED
            FROM A GROUP OF ONE OR MORE SPECIFIED AMINO ACIDS
            AS DEFINED IN THE SPECIFICATION."

(xi) SEQUENCE DESCRIPTION: SEQ ID NO:4:

```
Cys Xaa Xaa Xaa Xaa Leu Tyr Val Xaa Phe Xaa Xaa Xaa Gly Trp Xaa
1               5                   10                  15

Xaa Trp Xaa Xaa Ala Pro Xaa Gly Xaa Xaa Ala Xaa Tyr Cys Xaa Gly
            20                  25                  30

Xaa Cys Xaa Xaa Pro Xaa Xaa Xaa Xaa Xaa Xaa Xaa Xaa Asn His Ala
        35                  40                  45

Xaa Xaa Xaa Xaa Leu Xaa Xaa Xaa Xaa Xaa Xaa Xaa Xaa Xaa Xaa Xaa
    50                  55                  60

Xaa Cys Cys Xaa Pro Xaa Xaa Xaa Xaa Xaa Xaa Xaa Xaa Leu Xaa Xaa
65                  70                  75                  80

Xaa Xaa Xaa Xaa Xaa Val Xaa Leu Xaa Xaa Xaa Xaa Xaa Met Xaa Val
                85                  90                  95

Xaa Xaa Cys Gly Cys Xaa
            100
```

(2) INFORMATION FOR SEQ ID NO:5:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens
        (F) TISSUE TYPE: HIPPOCAMPUS (ix) FEATURE:
        (A) NAME/KEY: Protein
        (B) LOCATION: 1..139
        (D) OTHER INFORMATION: /label= hOP1-MATURE (xi) SEQUENCE DESCRIPTION: SEQ ID NO:5:

```
Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60
```

```
Tyr Tyr Cys Glu Gly Glu Cys Ala Phe Pro Leu Asn Ser Tyr Met Asn
 65                  70                  75                  80

Ala Thr Asn His Ala Ile Val Gln Thr Leu Val His Phe Ile Asn Pro
                 85                  90                  95

Glu Thr Val Pro Lys Pro Cys Cys Ala Pro Thr Gln Leu Asn Ala Ile
                100                 105                 110

Ser Val Leu Tyr Phe Asp Asp Ser Ser Asn Val Ile Leu Lys Lys Tyr
                115                 120                 125

Arg Asn Met Val Val Arg Ala Cys Gly Cys His
                130                 135

(2) INFORMATION FOR SEQ ID NO:6:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: MURIDAE
        (F) TISSUE TYPE: EMBRYO (ix) FEATURE:
        (A) NAME/KEY: Protein
        (B) LOCATION: 1..139
        (D) OTHER INFORMATION: /label= MOP1-MATURE (xi) SEQUENCE DESCRIPTION: SEQ ID NO:6:

Ser Thr Gly Gly Lys Gln Arg Ser Gln Asn Arg Ser Lys Thr Pro Lys
 1               5                  10                  15

Asn Gln Glu Ala Leu Arg Met Ala Ser Val Ala Glu Asn Ser Ser Ser
                 20                  25                  30

Asp Gln Arg Gln Ala Cys Lys Lys His Glu Leu Tyr Val Ser Phe Arg
                 35                  40                  45

Asp Leu Gly Trp Gln Asp Trp Ile Ile Ala Pro Glu Gly Tyr Ala Ala
 50                  55                  60

Tyr Tyr Cys Glu Gly Glu Cys Ala Phe Pro Leu Asn Ser Tyr Met Asn
 65                  70                  75                  80

Ala Thr Asn His Ala Ile Val Gln Thr Leu Val His Phe Ile Asn Pro
                 85                  90                  95

Asp Thr Val Pro Lys Pro Cys Cys Ala Pro Thr Gln Leu Asn Ala Ile
                100                 105                 110

Ser Val Leu Tyr Phe Asp Asp Ser Ser Asn Val Ile Leu Lys Lys Tyr
                115                 120                 125

Arg Asn Met Val Val Arg Ala Cys Gly Cys His
                130                 135

(2) INFORMATION FOR SEQ ID NO:7:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: HOMO SAPIENS
        (F) TISSUE TYPE: HIPPOCAMPUS
```

-continued

```
    (ix) FEATURE:
         (A) NAME/KEY: Protein
         (B) LOCATION: 1..139
         (D) OTHER INFORMATION: /label= HOP2-MATURE (xi) SEQUENCE DESCRIPTION: SEQ ID NO:7:

Ala Val Arg Pro Leu Arg Arg Gln Pro Lys Lys Ser Asn Glu Leu
1               5                   10                  15

Pro Gln Ala Asn Arg Leu Pro Gly Ile Phe Asp Asp Val His Gly Ser
            20                  25                  30

His Gly Arg Gln Val Cys Arg Arg His Glu Leu Tyr Val Ser Phe Gln
        35                  40                  45

Asp Leu Gly Trp Leu Asp Trp Val Ile Ala Pro Gln Gly Tyr Ser Ala
    50                  55                  60

Tyr Tyr Cys Glu Gly Glu Cys Ser Phe Pro Leu Asp Ser Cys Met Asn
65              70                  75                  80

Ala Thr Asn His Ala Ile Leu Gln Ser Leu Val His Leu Met Lys Pro
                85                  90                  95

Asn Ala Val Pro Lys Ala Cys Cys Ala Pro Thr Lys Leu Ser Ala Thr
            100                 105                 110

Ser Val Leu Tyr Tyr Asp Ser Ser Asn Asn Val Ile Leu Arg Lys His
        115                 120                 125

Arg Asn Met Val Val Lys Ala Cys Gly Cys His
    130                 135

(2) INFORMATION FOR SEQ ID NO:8:

(i) SEQUENCE CHARACTERISTICS:
         (A) LENGTH: 139 amino acids
         (B) TYPE: amino acid
         (C) STRANDEDNESS: single
         (D) TOPOLOGY: linear (ii) MOLECULE TYPE: protein (vi) ORIGINAL SOURCE:
         (A) ORGANISM: MURIDAE
         (F) TISSUE TYPE: EMBRYO (ix) FEATURE:
         (A) NAME/KEY: Protein
         (B) LOCATION: 1..139
         (D) OTHER INFORMATION: /label= MOP2-MATURE (xi) SEQUENCE DESCRIPTION: SEQ ID NO:8:

Ala Ala Arg Pro Leu Lys Arg Gln Pro Lys Lys Thr Asn Glu Leu
1               5                   10                  15

Pro His Pro Asn Lys Leu Pro Gly Ile Phe Asp Asp Gly His Gly Ser
            20                  25                  30

Arg Gly Arg Glu Val Cys Arg Arg His Glu Leu Tyr Val Ser Phe Arg
        35                  40                  45

Asp Leu Gly Trp Leu Asp Trp Val Ile Ala Pro Gln Gly Tyr Ser Ala
    50                  55                  60

Tyr Tyr Cys Glu Gly Glu Cys Ala Phe Pro Leu Asp Ser Cys Met Asn
65              70                  75                  80

Ala Thr Asn His Ala Ile Leu Gln Ser Leu Val His Leu Met Lys Pro
                85                  90                  95

Asp Val Val Pro Lys Ala Cys Cys Ala Pro Thr Lys Leu Ser Ala Thr
            100                 105                 110

Ser Val Leu Tyr Tyr Asp Ser Ser Asn Asn Val Ile Leu Arg Lys His
```

```
                    115                 120                 125
Arg Asn Met Val Val Lys Ala Cys Gly Cys His
    130                 135

(2) INFORMATION FOR SEQ ID NO:9:

(i) SEQUENCE CHARACTERISTICS:
        (A) LENGTH: 101 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: bovinae (ix) FEATURE:
        (A) NAME/KEY: Protein
        (B) LOCATION: 1..101
        (D) OTHER INFORMATION: /label= CBMP-2A-FX (xi) SEQUENCE DESCRIPTION: SEQ ID NO:9:

Cys Lys Arg His Pro Leu Tyr Val Asp Phe Ser Asp Val Gly Trp Asn
 1               5                  10                  15

Asp Trp Ile Val Ala Pro Pro Gly Tyr His Ala Phe Tyr Cys His Gly
                20                  25                  30

Glu Cys Pro Phe Pro Leu Ala Asp His Leu Asn Ser Thr Asn His Ala
            35                  40                  45

Ile Val Gln Thr Leu Val Asn Ser Val Asn Ser Lys Ile Pro Lys Ala
        50                  55                  60

Cys Cys Val Pro Thr Glu Leu Ser Ala Ile Ser Met Leu Tyr Leu Asp
65                  70                  75                  80

Glu Asn Glu Lys Val Val Leu Lys Asn Tyr Gln Asp Met Val Val Glu
                85                  90                  95

Gly Cys Gly Cys Arg
            100

(2) INFORMATION FOR SEQ ID NO:10:

(i) SEQUENCE CHARACTERISTICS:
        (A) LENGTH: 101 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: HOMO SAPIENS
        (F) TISSUE TYPE: hippocampus (ix) FEATURE:
        (A) NAME/KEY: Protein
        (B) LOCATION: 1..101
        (D) OTHER INFORMATION: /label= CBMP-2B-FX (xi) SEQUENCE DESCRIPTION: SEQ ID NO:10:

Cys Arg Arg His Ser Leu Tyr Val Asp Phe Ser Asp Val Gly Trp Asn
 1               5                  10                  15

Asp Trp Ile Val Ala Pro Pro Gly Tyr Gln Ala Phe Tyr Cys His Gly
                20                  25                  30

Asp Cys Pro Phe Pro Leu Ala Asp His Leu Asn Ser Thr Asn His Ala
            35                  40                  45

Ile Val Gln Thr Leu Val Asn Ser Val Asn Ser Ser Ile Pro Lys Ala
```

```
                   50                  55                  60
Cys Cys Val Pro Thr Glu Leu Ser Ala Ile Ser Met Leu Tyr Leu Asp
 65                  70                  75                  80

Glu Tyr Asp Lys Val Val Leu Lys Asn Tyr Gln Glu Met Val Val Glu
                     85                  90                  95

Gly Cys Gly Cys Arg
                100
```

(2) INFORMATION FOR SEQ ID NO:11:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: DROSOPHILA MELANOGASTER (ix) FEATURE:
        (A) NAME/KEY: Protein
        (B) LOCATION: 1..101
        (D) OTHER INFORMATION: /label= DPP-FX (xi) SEQUENCE DESCRIPTION: SEQ ID NO:11:

```
Cys Arg Arg His Ser Leu Tyr Val Asp Phe Ser Asp Val Gly Trp Asp
 1                   5                  10                  15

Asp Trp Ile Val Ala Pro Leu Gly Tyr Asp Ala Tyr Tyr Cys His Gly
                    20                  25                  30

Lys Cys Pro Phe Pro Leu Ala Asp His Phe Asn Ser Thr Asn His Ala
                    35                  40                  45

Val Val Gln Thr Leu Val Asn Asn Asn Asn Pro Gly Lys Val Pro Lys
                    50                  55                  60

Ala Cys Cys Val Pro Thr Gln Leu Asp Ser Val Ala Met Leu Tyr Leu
 65                  70                  75                  80

Asn Asp Gln Ser Thr Val Val Leu Lys Asn Tyr Gln Glu Met Thr Val
                    85                  90                  95

Val Gly Cys Gly Cys Arg
                    100
```

(2) INFORMATION FOR SEQ ID NO:12:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: XENOPUS (ix) FEATURE:
        (A) NAME/KEY: Protein
        (B) LOCATION: 1..102
        (D) OTHER INFORMATION: /label= VGL-FX (xi) SEQUENCE DESCRIPTION: SEQ ID NO:12:

```
Cys Lys Lys Arg His Leu Tyr Val Glu Phe Lys Asp Val Gly Trp Gln
 1                   5                  10                  15

Asn Trp Val Ile Ala Pro Gln Gly Tyr Met Ala Asn Tyr Cys Tyr Gly
                    20                  25                  30
```

```
Glu Cys Pro Tyr Pro Leu Thr Glu Ile Leu Asn Gly Ser Asn His Ala
            35                  40                  45

Ile Leu Gln Thr Leu Val His Ser Ile Glu Pro Glu Asp Ile Pro Leu
 50                      55                  60

Pro Cys Cys Val Pro Thr Lys Met Ser Pro Ile Ser Met Leu Phe Tyr
 65                  70                  75                  80

Asp Asn Asn Asp Asn Val Val Leu Arg His Tyr Glu Asn Met Ala Val
                 85                  90                  95

Asp Glu Cys Gly Cys Arg
           100
```

(2) INFORMATION FOR SEQ ID NO:13:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: MURIDAE (ix) FEATURE:
        (A) NAME/KEY: Protein
        (B) LOCATION: 1..102
        (D) OTHER INFORMATION: /label= VGR-1-FX (xi) SEQUENCE DESCRIPTION: SEQ ID NO:13:

```
Cys Lys Lys His Glu Leu Tyr Val Ser Phe Gln Asp Val Gly Trp Gln
 1               5                  10                  15

Asp Trp Ile Ile Ala Pro Lys Gly Tyr Ala Ala Asn Tyr Cys Asp Gly
             20                  25                  30

Glu Cys Ser Phe Pro Leu Asn Ala His Met Asn Ala Thr Asn His Ala
            35                  40                  45

Ile Val Gln Thr Leu Val His Val Met Asn Pro Glu Tyr Val Pro Lys
 50                      55                  60

Pro Cys Cys Ala Pro Thr Lys Val Asn Ala Ile Ser Val Leu Tyr Phe
 65                  70                  75                  80

Asp Asp Asn Ser Asn Val Ile Leu Lys Lys Tyr Arg Asn Met Val Val
                 85                  90                  95

Arg Ala Cys Gly Cys His
           100
```

(2) INFORMATION FOR SEQ ID NO:14:

(i) SEQUENCE CHARACTERISTICS:
        (A) LENGTH: 106 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Homo sapiens
        (F) TISSUE TYPE: brain (ix) FEATURE:
        (A) NAME/KEY: Protein (B) LOCATION: 1..106
        (D) OTHER INFORMATION: /note= "GDF-1 (fx)"

(xi) SEQUENCE DESCRIPTION: SEQ ID NO:14:

Cys Arg Ala Arg Arg Leu Tyr Val Ser Phe Arg Glu Val Gly Trp His
1               5                   10                  15

Arg Trp Val Ile Ala Pro Arg Gly Phe Leu Ala Asn Tyr Cys Gln Gly
            20                  25                  30

Gln Cys Ala Leu Pro Val Ala Leu Ser Gly Ser Gly Pro Pro Ala
        35                  40                  45

Leu Asn His Ala Val Leu Arg Ala Leu Met His Ala Ala Ala Pro Gly
    50                  55                  60

Ala Ala Asp Leu Pro Cys Cys Val Pro Ala Arg Leu Ser Pro Ile Ser
65              70                  75                  80

Val Leu Phe Phe Asp Asn Ser Asp Asn Val Val Leu Arg Gln Tyr Glu
                85                  90                  95

Asp Met Val Val Asp Glu Cys Gly Cys Arg
            100                 105

(2) INFORMATION FOR SEQ ID NO:15:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Cys Xaa Xaa Xaa Xaa
1               5

(2) INFORMATION FOR SEQ ID NO:16:

(i) SEQUENCE CHARACTERISTICS:
        (A) LENGTH: 1822 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: HOMO SAPIENS
        (F) TISSUE TYPE: HIPPOCAMPUS (ix) FEATURE:
        (A) NAME/KEY: CDS
        (B) LOCATION: 49..1341
        (C) IDENTIFICATION METHOD: experimental
        (D) OTHER INFORMATION: /function= "OSTEOGENIC PROTEIN"
            /product= "OP1"
            /evidence= EXPERIMENTAL
            /standard_name= "OP1"

(xi) SEQUENCE DESCRIPTION: SEQ ID NO:16:

GGTGCGGGCC CGGAGCCCGG AGCCCGGGTA GCGCGTAGAG CCGGCGCG ATG CAC GTG      57
                                                    Met His Val
                                                    1

CGC TCA CTG CGA GCT GCG GCG CCG CAC AGC TTC GTG GCG CTC TGG GCA     105
Arg Ser Leu Arg Ala Ala Ala Pro His Ser Phe Val Ala Leu Trp Ala
    5                   10                  15

-continued

| | | | | | | | | | | | | | | | | |
|---|---|---|---|---|---|---|---|---|---|---|---|---|---|---|---|---|
| CCC | CTG | TTC | CTG | CTG | CGC | TCC | GCC | CTG | GCC | GAC | TTC | AGC | CTG | GAC | AAC | 153 |
| Pro | Leu | Phe | Leu | Leu | Arg | Ser | Ala | Leu | Ala | Asp | Phe | Ser | Leu | Asp | Asn | |
| 20 | | | | 25 | | | | | 30 | | | | | 35 | | |
| GAG | GTG | CAC | TCG | AGC | TTC | ATC | CAC | CGG | CGC | CTC | CGC | AGC | CAG | GAG | CGG | 201 |
| Glu | Val | His | Ser | Ser | Phe | Ile | His | Arg | Arg | Leu | Arg | Ser | Gln | Glu | Arg | |
| | | | 40 | | | | | 45 | | | | | 50 | | | |
| CGG | GAG | ATG | CAG | CGC | GAG | ATC | CTC | TCC | ATT | TTG | GGC | TTG | CCC | CAC | CGC | 249 |
| Arg | Glu | Met | Gln | Arg | Glu | Ile | Leu | Ser | Ile | Leu | Gly | Leu | Pro | His | Arg | |
| | | | 55 | | | | | 60 | | | | | 65 | | | |
| CCG | CGC | CCG | CAC | CTC | CAG | GGC | AAG | CAC | AAC | TCG | GCA | CCC | ATG | TTC | ATG | 297 |
| Pro | Arg | Pro | His | Leu | Gln | Gly | Lys | His | Asn | Ser | Ala | Pro | Met | Phe | Met | |
| | | 70 | | | | | 75 | | | | | 80 | | | | |
| CTG | GAC | CTG | TAC | AAC | GCC | ATG | GCG | GTG | GAG | GAG | GGC | GGC | GGG | CCC | GGC | 345 |
| Leu | Asp | Leu | Tyr | Asn | Ala | Met | Ala | Val | Glu | Glu | Gly | Gly | Gly | Pro | Gly | |
| | | 85 | | | | | 90 | | | | | 95 | | | | |
| GGC | CAG | GGC | TTC | TCC | TAC | CCC | TAC | AAG | GCC | GTC | TTC | AGT | ACC | CAG | GGC | 393 |
| Gly | Gln | Gly | Phe | Ser | Tyr | Pro | Tyr | Lys | Ala | Val | Phe | Ser | Thr | Gln | Gly | |
| 100 | | | | 105 | | | | | 110 | | | | | 115 | | |
| CCC | CCT | CTG | GCC | AGC | CTG | CAA | GAT | AGC | CAT | TTC | CTC | ACC | GAC | GCC | GAC | 441 |
| Pro | Pro | Leu | Ala | Ser | Leu | Gln | Asp | Ser | His | Phe | Leu | Thr | Asp | Ala | Asp | |
| | | | 120 | | | | | 125 | | | | | 130 | | | |
| ATG | GTC | ATG | AGC | TTC | GTC | AAC | CTC | GTG | GAA | CAT | GAC | AAG | GAA | TTC | TTC | 489 |
| Met | Val | Met | Ser | Phe | Val | Asn | Leu | Val | Glu | His | Asp | Lys | Glu | Phe | Phe | |
| | | | 135 | | | | | 140 | | | | | 145 | | | |
| CAC | CCA | CGC | TAC | CAC | CAT | CGA | GAG | TTC | CGG | TTT | GAT | CTT | TCC | AAG | ATC | 537 |
| His | Pro | Arg | Tyr | His | His | Arg | Glu | Phe | Arg | Phe | Asp | Leu | Ser | Lys | Ile | |
| | | 150 | | | | | 155 | | | | | 160 | | | | |
| CCA | GAA | GGG | GAA | GCT | GTC | ACG | GCA | GCC | GAA | TTC | CGG | ATC | TAC | AAG | GAC | 585 |
| Pro | Glu | Gly | Glu | Ala | Val | Thr | Ala | Ala | Glu | Phe | Arg | Ile | Tyr | Lys | Asp | |
| | 165 | | | | | 170 | | | | | 175 | | | | | |
| TAC | ATC | CGG | GAA | CGC | TTC | GAC | AAT | GAG | ACG | TTC | CGG | ATC | AGC | GTT | TAT | 633 |
| Tyr | Ile | Arg | Glu | Arg | Phe | Asp | Asn | Glu | Thr | Phe | Arg | Ile | Ser | Val | Tyr | |
| 180 | | | | 185 | | | | | 190 | | | | | 195 | | |
| CAG | GTG | CTC | CAG | GAG | CAC | TTG | GGC | AGG | GAA | TCG | GAT | CTC | TTC | CTG | CTC | 681 |
| Gln | Val | Leu | Gln | Glu | His | Leu | Gly | Arg | Glu | Ser | Asp | Leu | Phe | Leu | Leu | |
| | | | 200 | | | | | 205 | | | | | 210 | | | |
| GAC | AGC | CGT | ACC | CTC | TGG | GCC | TCG | GAG | GAG | GGC | TGG | CTG | GTG | TTT | GAC | 729 |
| Asp | Ser | Arg | Thr | Leu | Trp | Ala | Ser | Glu | Glu | Gly | Trp | Leu | Val | Phe | Asp | |
| | | | 215 | | | | | 220 | | | | | 225 | | | |
| ATC | ACA | GCC | ACC | AGC | AAC | CAC | TGG | GTG | GTC | AAT | CCG | CGG | CAC | AAC | CTG | 777 |
| Ile | Thr | Ala | Thr | Ser | Asn | His | Trp | Val | Val | Asn | Pro | Arg | His | Asn | Leu | |
| | | | 230 | | | | | 235 | | | | | 240 | | | |
| GGC | CTG | CAG | CTC | TCG | GTG | GAG | ACG | CTG | GAT | GGG | CAG | AGC | ATC | AAC | CCC | 825 |
| Gly | Leu | Gln | Leu | Ser | Val | Glu | Thr | Leu | Asp | Gly | Gln | Ser | Ile | Asn | Pro | |
| | 245 | | | | | 250 | | | | | 255 | | | | | |
| AAG | TTG | GCG | GGC | CTG | ATT | GGG | CGG | CAC | GGG | CCC | CAG | AAC | AAG | CAG | CCC | 873 |
| Lys | Leu | Ala | Gly | Leu | Ile | Gly | Arg | His | Gly | Pro | Gln | Asn | Lys | Gln | Pro | |
| 260 | | | | 265 | | | | | 270 | | | | | 275 | | |
| TTC | ATG | GTG | GCT | TTC | TTC | AAG | GCC | ACG | GAG | GTC | CAC | TTC | CGC | AGC | ATC | 921 |
| Phe | Met | Val | Ala | Phe | Phe | Lys | Ala | Thr | Glu | Val | His | Phe | Arg | Ser | Ile | |
| | | | 280 | | | | | 285 | | | | | 290 | | | |
| CGG | TCC | ACG | GGG | AGC | AAA | CAG | CGC | AGC | CAG | AAC | CGC | TCC | AAG | ACG | CCC | 969 |
| Arg | Ser | Thr | Gly | Ser | Lys | Gln | Arg | Ser | Gln | Asn | Arg | Ser | Lys | Thr | Pro | |
| | | 295 | | | | | 300 | | | | | 305 | | | | |
| AAG | AAC | CAG | GAA | GCC | CTG | CGG | ATG | GCC | AAC | GTG | GCA | GAG | AAC | AGC | AGC | 1017 |
| Lys | Asn | Gln | Glu | Ala | Leu | Arg | Met | Ala | Asn | Val | Ala | Glu | Asn | Ser | Ser | |
| | 310 | | | | | 315 | | | | | 320 | | | | | |
| AGC | GAC | CAG | AGG | CAG | GCC | TGT | AAG | AAG | CAC | GAG | CTG | TAT | GTC | AGC | TTC | 1065 |
| Ser | Asp | Gln | Arg | Gln | Ala | Cys | Lys | Lys | His | Glu | Leu | Tyr | Val | Ser | Phe | |

-continued

```
        325                 330                 335
CGA GAC CTG GGC TGG CAG GAC TGG ATC ATC GCG CCT GAA GGC TAC GCC    1113
Arg Asp Leu Gly Trp Gln Asp Trp Ile Ile Ala Pro Glu Gly Tyr Ala
340                 345                 350                 355

GCC TAC TAC TGT GAG GGG GAG TGT GCC TTC CCT CTG AAC TCC TAC ATG    1161
Ala Tyr Tyr Cys Glu Gly Glu Cys Ala Phe Pro Leu Asn Ser Tyr Met
                360                 365                 370

AAC GCC ACC AAC CAC GCC ATC GTG CAG ACG CTG GTC CAC TTC ATC AAC    1209
Asn Ala Thr Asn His Ala Ile Val Gln Thr Leu Val His Phe Ile Asn
        375                 380                 385

CCG GAA ACG GTG CCC AAG CCC TGC TGT GCG CCC ACG CAG CTC AAT GCC    1257
Pro Glu Thr Val Pro Lys Pro Cys Cys Ala Pro Thr Gln Leu Asn Ala
            390                 395                 400

ATC TCC GTC CTC TAC TTC GAT GAC AGC TCC AAC GTC ATC CTG AAG AAA    1305
Ile Ser Val Leu Tyr Phe Asp Asp Ser Ser Asn Val Ile Leu Lys Lys
405                 410                 415

TAC AGA AAC ATG GTG GTC CGG GCC TGT GGC TGC CAC TAGCTCCTCC         1351
Tyr Arg Asn Met Val Val Arg Ala Cys Gly Cys His
420                 425                 430

GAGAATTCAG ACCCTTTGGG GCCAAGTTTT TCTGGATCCT CCATTGCTCG CCTTGGCCAG   1411

GAACCAGCAG ACCAACTGCC TTTTGTGAGA CCTTCCCCTC CCTATCCCCA ACTTTAAAGG   1471

TGTGAGAGTA TTAGGAAACA TGAGCAGCAT ATGGCTTTTG ATCAGTTTTT CAGTGGCAGC   1531

ATCCAATGAA CAAGATCCTA CAAGCTGTGC AGGCAAAACC TAGCAGGAAA AAAAAACAAC   1591

GCATAAAGAA AAATGGCCGG GCCAGGTCAT TGGCTGGGAA GTCTCAGCCA TGCACGGACT   1651

CGTTTCCAGA GGTAATTATG AGCGCCTACC AGCCAGGCCA CCCAGCCGTG GGAGGAAGGG   1711

GGCGTGGCAA GGGGTGGGCA CATTGGTGTC TGTGCGAAAG GAAAATTGAC CCGGAAGTTC   1771

CTGTAATAAA TGTCACAATA AAACGAATGA ATGAAAAAAA AAAAAAAAA A            1822

(2) INFORMATION FOR SEQ ID NO:17:

(i) SEQUENCE CHARACTERISTICS:
        (A) LENGTH: 431 amino acids
        (B) TYPE: amino acid
        (D) TOPOLOGY: linear (ii) MOLECULE TYPE: protein (xi) SEQUENCE DESCRIPTION: SEQ ID NO:17:

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
                100                 105                 110

Thr Gln Gly Pro Pro Leu Ala Ser Leu Gln Asp Ser His Phe Leu Thr
            115                 120                 125

Asp Ala Asp Met Val Met Ser Phe Val Asn Leu Val Glu His Asp Lys
```

```
              130                 135                 140
Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
                180                 185                 190

Ser Val Tyr Gln Val Leu Gln Glu His Leu Gly Arg Glu Ser Asp Leu
                195                 200                 205

Phe Leu Leu Asp Ser Arg Thr Leu Trp Ala Ser Glu Glu Gly Trp Leu
210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
                260                 265                 270

Lys Gln Pro Phe Met Val Ala Phe Phe Lys Ala Thr Glu Val His Phe
                275                 280                 285

Arg Ser Ile Arg Ser Thr Gly Ser Lys Gln Arg Ser Gln Asn Arg Ser
290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
                340                 345                 350

Gly Tyr Ala Ala Tyr Tyr Cys Glu Gly Glu Cys Ala Phe Pro Leu Asn
                355                 360                 365

Ser Tyr Met Asn Ala Thr Asn His Ala Ile Val Gln Thr Leu Val His
                370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
                420                 425                 430
```

(2) INFORMATION FOR SEQ ID NO:18:

(i) SEQUENCE CHARACTERISTICS:
        (A) LENGTH: 1873 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: MURIDAE
        (F) TISSUE TYPE: EMBRYO (ix) FEATURE:
        (A) NAME/KEY: CDS
        (B) LOCATION: 104..1393
        (D) OTHER INFORMATION: /function= "OSTEOGENIC PROTEIN"

-continued

/product= "MOP1"
/note= "MOP1 (CDNA)"

(xi) SEQUENCE DESCRIPTION: SEQ ID NO:18:

```
CTGCAGCAAG TGACCTCGGG TCGTGGACCG CTGCCCTGCC CCCTCCGCTG CCACCTGGGG      60

CGGCGCGGGC CCGGTGCCCC GGATCGCGCG TAGAGCCGGC GCG ATG CAC GTG CGC       115
                                               Met His Val Arg
                                                 1

TCG CTG CGC GCT GCG GCG CCA CAC AGC TTC GTG GCG CTC TGG GCG CCT       163
Ser Leu Arg Ala Ala Ala Pro His Ser Phe Val Ala Leu Trp Ala Pro
  5              10                  15                  20

CTG TTC TTG CTG CGC TCC GCC CTG GCC GAT TTC AGC CTG GAC AAC GAG       211
Leu Phe Leu Leu Arg Ser Ala Leu Ala Asp Phe Ser Leu Asp Asn Glu
                 25                  30                  35

GTG CAC TCC AGC TTC ATC CAC CGG CGC CTC CGC AGC CAG GAG CGG CGG       259
Val His Ser Ser Phe Ile His Arg Arg Leu Arg Ser Gln Glu Arg Arg
                 40                  45                  50

GAG ATG CAG CGG GAG ATC CTG TCC ATC TTA GGG TTG CCC CAT CGC CCG       307
Glu Met Gln Arg Glu Ile Leu Ser Ile Leu Gly Leu Pro His Arg Pro
         55                  60                  65

CGC CCG CAC CTC CAG GGA AAG CAT AAT TCG GCG CCC ATG TTC ATG TTG       355
Arg Pro His Leu Gln Gly Lys His Asn Ser Ala Pro Met Phe Met Leu
 70                  75                  80

GAC CTG TAC AAC GCC ATG GCG GTG GAG GAG AGC GGG CCG GAC GGA CAG       403
Asp Leu Tyr Asn Ala Met Ala Val Glu Glu Ser Gly Pro Asp Gly Gln
 85                  90                  95                 100

GGC TTC TCC TAC CCC TAC AAG GCC GTC TTC AGT ACC CAG GGC CCC CCT       451
Gly Phe Ser Tyr Pro Tyr Lys Ala Val Phe Ser Thr Gln Gly Pro Pro
                105                 110                 115

TTA GCC AGC CTG CAG GAC AGC CAT TTC CTC ACT GAC GCC GAC ATG GTC       499
Leu Ala Ser Leu Gln Asp Ser His Phe Leu Thr Asp Ala Asp Met Val
                120                 125                 130

ATG AGC TTC GTC AAC CTA GTG GAA CAT GAC AAA GAA TTC TTC CAC CCT       547
Met Ser Phe Val Asn Leu Val Glu His Asp Lys Glu Phe Phe His Pro
        135                 140                 145

CGA TAC CAC CAT CGG GAG TTC CGG TTT GAT CTT TCC AAG ATC CCC GAG       595
Arg Tyr His His Arg Glu Phe Arg Phe Asp Leu Ser Lys Ile Pro Glu
    150                 155                 160

GGC GAA CGG GTG ACC GCA GCC GAA TTC AGG ATC TAT AAG GAC TAC ATC       643
Gly Glu Arg Val Thr Ala Ala Glu Phe Arg Ile Tyr Lys Asp Tyr Ile
165                 170                 175                 180

CGG GAG CGA TTT GAC AAC GAG ACC TTC CAG ATC ACA GTC TAT CAG GTG       691
Arg Glu Arg Phe Asp Asn Glu Thr Phe Gln Ile Thr Val Tyr Gln Val
                185                 190                 195

CTC CAG GAG CAC TCA GGC AGG GAG TCG GAC CTC TTC TTG CTG GAC AGC       739
Leu Gln Glu His Ser Gly Arg Glu Ser Asp Leu Phe Leu Leu Asp Ser
                200                 205                 210

CGC ACC ATC TGG GCT TCT GAG GAG GGC TGG TTG GTG TTT GAT ATC ACA       787
Arg Thr Ile Trp Ala Ser Glu Glu Gly Trp Leu Val Phe Asp Ile Thr
                215                 220                 225

GCC ACC AGC AAC CAC TGG GTG GTC AAC CCT CGG CAC AAC CTG GGC TTA       835
Ala Thr Ser Asn His Trp Val Val Asn Pro Arg His Asn Leu Gly Leu
        230                 235                 240

CAG CTC TCT GTG GAG ACC CTG GAT GGG CAG AGC ATC AAC CCC AAG TTG       883
Gln Leu Ser Val Glu Thr Leu Asp Gly Gln Ser Ile Asn Pro Lys Leu
245                 250                 255                 260

GCA GGC CTG ATT GGA CGG CAT GGA CCC CAG AAC AAG CAA CCC TTC ATG       931
Ala Gly Leu Ile Gly Arg His Gly Pro Gln Asn Lys Gln Pro Phe Met
                265                 270                 275
```

-continued

```
GTG GCC TTC TTC AAG GCC ACG GAA GTC CAT CTC CGT AGT ATC CGG TCC        979
Val Ala Phe Phe Lys Ala Thr Glu Val His Leu Arg Ser Ile Arg Ser
            280                 285                 290

ACG GGG GGC AAG CAG CGC AGC CAG AAT CGC TCC AAG ACG CCA AAG AAC       1027
Thr Gly Gly Lys Gln Arg Ser Gln Asn Arg Ser Lys Thr Pro Lys Asn
            295                 300                 305

CAA GAG GCC CTG AGG ATG GCC AGT GTG GCA GAA AAC AGC AGC AGT GAC       1075
Gln Glu Ala Leu Arg Met Ala Ser Val Ala Glu Asn Ser Ser Ser Asp
    310                 315                 320

CAG AGG CAG GCC TGC AAG AAA CAT GAG CTG TAC GTC AGC TTC CGA GAC       1123
Gln Arg Gln Ala Cys Lys Lys His Glu Leu Tyr Val Ser Phe Arg Asp
325                 330                 335                 340

CTT GGC TGG CAG GAC TGG ATC ATT GCA CCT GAA GGC TAT GCT GCC TAC       1171
Leu Gly Trp Gln Asp Trp Ile Ile Ala Pro Glu Gly Tyr Ala Ala Tyr
                345                 350                 355

TAC TGT GAG GGA GAG TGC GCC TTC CCT CTG AAC TCC TAC ATG AAC GCC       1219
Tyr Cys Glu Gly Glu Cys Ala Phe Pro Leu Asn Ser Tyr Met Asn Ala
            360                 365                 370

ACC AAC CAC GCC ATC GTC CAG ACA CTG GTT CAC TTC ATC AAC CCA GAC       1267
Thr Asn His Ala Ile Val Gln Thr Leu Val His Phe Ile Asn Pro Asp
            375                 380                 385

ACA GTA CCC AAG CCC TGC TGT GCG CCC ACC CAG CTC AAC GCC ATC TCT       1315
Thr Val Pro Lys Pro Cys Cys Ala Pro Thr Gln Leu Asn Ala Ile Ser
    390                 395                 400

GTC CTC TAC TTC GAC GAC AGC TCT AAT GTC GAC CTG AAG AAG TAC AGA       1363
Val Leu Tyr Phe Asp Asp Ser Ser Asn Val Asp Leu Lys Lys Tyr Arg
405                 410                 415                 420

AAC ATG GTG GTC CGG GCC TGT GGC TGC CAC TAGCTCTTCC TGAGACCCTG         1413
Asn Met Val Val Arg Ala Cys Gly Cys His
                425                 430

ACCTTTGCGG GGCCACACCT TTCCAAATCT TCGATGTCTC ACCATCTAAG TCTCTCACTG     1473

CCCACCTTGG CGAGGAGAAC AGACCAACCT CTCCTGAGCC TTCCCTCACC TCCCAACCGG     1533

AAGCATGTAA GGGTTCCAGA AACCTGAGCG TGCAGCAGCT GATGAGCGCC CTTTCCTTCT     1593

GGCACGTGAC GGACAAGATC CTACCAGCTA CCACAGCAAA CGCCTAAGAG CAGGAAAAAT     1653

GTCTGCCAGG AAAGTGTCCA GTGTCCACAT GGCCCCTGGC GCTCTGAGTC TTTGAGGAGT     1713

AATCGCAAGC CTCGTTCAGC TGCAGCAGAA GGAAGGGCTT AGCCAGGGTG GGCGCTGGCG     1773

TCTGTGTTGA AGGGAAACCA AGCAGAAGCC ACTGTAATGA TATGTCACAA TAAAACCCAT     1833

GAATGAAAAA AAAAAAAAAA AAAAAAAAAA AAAAGAATTC                           1873
```

(2) INFORMATION FOR SEQ ID NO:19:

(i) SEQUENCE CHARACTERISTICS:
        (A) LENGTH: 430 amino acids
        (B) TYPE: amino acid
        (D) TOPOLOGY: linear (ii) MOLECULE TYPE: protein (xi) SEQUENCE DESCRIPTION: SEQ ID NO:19:

```
Met His Val Arg Ser Leu Arg Ala Ala Ala Pro His Ser Phe Val Ala
  1               5                  10                  15

Leu Trp Ala Pro Leu Phe Leu Leu Arg Ser Ala Leu Ala Asp Phe Ser
             20                  25                  30

Leu Asp Asn Glu Val His Ser Ser Phe Ile His Arg Arg Leu Arg Ser
         35                  40                  45

Gln Glu Arg Arg Glu Met Gln Arg Glu Ile Leu Ser Ile Leu Gly Leu
     50                  55                  60
```

```
Pro His Arg Pro Arg Pro His Leu Gln Gly Lys His Asn Ser Ala Pro
 65                  70                  75                  80

Met Phe Met Leu Asp Leu Tyr Asn Ala Met Ala Val Glu Glu Ser Gly
                 85                  90                  95

Pro Asp Gly Gln Gly Phe Ser Tyr Pro Tyr Lys Ala Val Phe Ser Thr
            100                 105                 110

Gln Gly Pro Pro Leu Ala Ser Leu Gln Asp Ser His Phe Leu Thr Asp
        115                 120                 125

Ala Asp Met Val Met Ser Phe Val Asn Leu Val Glu His Asp Lys Glu
    130                 135                 140

Phe Phe His Pro Arg Tyr His His Arg Glu Phe Arg Phe Asp Leu Ser
145                 150                 155                 160

Lys Ile Pro Glu Gly Glu Arg Val Thr Ala Ala Glu Phe Arg Ile Tyr
                165                 170                 175

Lys Asp Tyr Ile Arg Glu Arg Phe Asp Asn Glu Thr Phe Gln Ile Thr
            180                 185                 190

Val Tyr Gln Val Leu Gln Glu His Ser Gly Arg Glu Ser Asp Leu Phe
        195                 200                 205

Leu Leu Asp Ser Arg Thr Ile Trp Ala Ser Glu Glu Gly Trp Leu Val
    210                 215                 220

Phe Asp Ile Thr Ala Thr Ser Asn His Trp Val Val Asn Pro Arg His
225                 230                 235                 240

Asn Leu Gly Leu Gln Leu Ser Val Glu Thr Leu Asp Gly Gln Ser Ile
                245                 250                 255

Asn Pro Lys Leu Ala Gly Leu Ile Gly Arg His Gly Pro Gln Asn Lys
            260                 265                 270

Gln Pro Phe Met Val Ala Phe Phe Lys Ala Thr Glu Val His Leu Arg
        275                 280                 285

Ser Ile Arg Ser Thr Gly Gly Lys Gln Arg Ser Gln Asn Arg Ser Lys
    290                 295                 300

Thr Pro Lys Asn Gln Glu Ala Leu Arg Met Ala Ser Val Ala Glu Asn
305                 310                 315                 320

Ser Ser Ser Asp Gln Arg Gln Ala Cys Lys Lys His Glu Leu Tyr Val
                325                 330                 335

Ser Phe Arg Asp Leu Gly Trp Gln Asp Trp Ile Ile Ala Pro Glu Gly
            340                 345                 350

Tyr Ala Ala Tyr Tyr Cys Glu Gly Glu Cys Ala Phe Pro Leu Asn Ser
        355                 360                 365

Tyr Met Asn Ala Thr Asn His Ala Ile Val Gln Thr Leu Val His Phe
    370                 375                 380

Ile Asn Pro Asp Thr Val Pro Lys Pro Cys Cys Ala Pro Thr Gln Leu
385                 390                 395                 400

Asn Ala Ile Ser Val Leu Tyr Phe Asp Asp Ser Ser Asn Val Asp Leu
                405                 410                 415

Lys Lys Tyr Arg Asn Met Val Val Arg Ala Cys Gly Cys His
            420                 425                 430
```

(2) INFORMATION FOR SEQ ID NO:20:

(i) SEQUENCE CHARACTERISTICS:
        (A) LENGTH: 1723 base pairs
        (B) TYPE: nucleic acid
        (C) STRANDEDNESS: single
        (D) TOPOLOGY: linear -continued

```
    (ii) MOLECULE TYPE: cDNA (vi) ORIGINAL SOURCE:
          (A) ORGANISM: Homo sapiens
          (F) TISSUE TYPE: HIPPOCAMPUS (ix) FEATURE:
          (A) NAME/KEY: CDS
          (B) LOCATION: 490..1696
          (D) OTHER INFORMATION: /function= "OSTEOGENIC PROTEIN"
              /product= "hOP2-PP"
              /note= "hOP2 (cDNA)"

(xi) SEQUENCE DESCRIPTION: SEQ ID NO:20:

GGCGCCGGCA GAGCAGGAGT GGCTGGAGGA GCTGTGGTTG GAGCAGGAGG TGGCACGGCA        60

GGGCTGGAGG GCTCCCTATG AGTGGCGGAG ACGGCCCAGG AGGCGCTGGA GCAACAGCTC       120

CCACACCGCA CCAAGCGGTG GCTGCAGGAG CTCGCCCATC GCCCCTGCGC TGCTCGGACC       180

GCGGCCACAG CCGGACTGGC GGGTACGGCG GCGACAGAGG CATTGGCCGA GAGTCCCAGT       240

CCGCAGAGTA GCCCCGGCCT CGAGGCGGTG GCGTCCCGGT CCTCTCCGTC CAGGAGCCAG       300

GACAGGTGTC GCGCGGCGGG GCTCCAGGGA CCGCGCCTGA GGCCGGCTGC CCGCCCGTCC       360

CGCCCCGCCC CGCCGCCCGC CGCCCGCCGA GCCCAGCCTC CTTGCCGTCG GGGCGTCCCC       420

AGGCCCTGGG TCGGCCGCGG AGCCGATGCG CGCCCGCTGA GCGCCCCAGC TGAGCGCCCC       480

CGGCCTGCC ATG ACC GCG CTC CCC GGC CCG CTC TGG CTC CTG GGC CTG          528
           Met Thr Ala Leu Pro Gly Pro Leu Trp Leu Leu Gly Leu
             1               5                  10

GCG CTA TGC GCG CTG GGC GGG GGC GGC CCC GGC CTG CGA CCC CCG CCC        576
Ala Leu Cys Ala Leu Gly Gly Gly Gly Pro Gly Leu Arg Pro Pro Pro
 15                  20                  25

GGC TGT CCC CAG CGA CGT CTG GGC GCG CGC GAG CGC CGG GAC GTG CAG        624
Gly Cys Pro Gln Arg Arg Leu Gly Ala Arg Glu Arg Arg Asp Val Gln
 30                  35                  40                  45

CGC GAG ATC CTG GCG GTG CTC GGG CTG CCT GGG CGG CCC CGG CCC CGC        672
Arg Glu Ile Leu Ala Val Leu Gly Leu Pro Gly Arg Pro Arg Pro Arg
                 50                  55                  60

GCG CCA CCC GCC GCC TCC CGG CTG CCC GCG TCC GCG CCG CTC TTC ATG        720
Ala Pro Pro Ala Ala Ser Arg Leu Pro Ala Ser Ala Pro Leu Phe Met
                 65                  70                  75

CTG GAC CTG TAC CAC GCC ATG GCC GGC GAC GAC GAC GAG GAC GGC GCG        768
Leu Asp Leu Tyr His Ala Met Ala Gly Asp Asp Asp Glu Asp Gly Ala
             80                  85                  90

CCC GCG GAG CGG CGC CTG GGC CGC GCC GAC CTG GTC ATG AGC TTC GTT        816
Pro Ala Glu Arg Arg Leu Gly Arg Ala Asp Leu Val Met Ser Phe Val
         95                  100                 105

AAC ATG GTG GAG CGA GAC CGT GCC CTG GGC CAC CAG GAG CCC CAT TGG        864
Asn Met Val Glu Arg Asp Arg Ala Leu Gly His Gln Glu Pro His Trp
110                 115                 120                 125

AAG GAG TTC CGC TTT GAC CTG ACC CAG ATC CCG GCT GGG GAG GCG GTC        912
Lys Glu Phe Arg Phe Asp Leu Thr Gln Ile Pro Ala Gly Glu Ala Val
                130                 135                 140

ACA GCT GCG GAG TTC CGG ATT TAC AAG GTG CCC AGC ATC CAC CTG CTC        960
Thr Ala Ala Glu Phe Arg Ile Tyr Lys Val Pro Ser Ile His Leu Leu
                145                 150                 155

AAC AGG ACC CTC CAC GTC AGC ATG TTC CAG GTG GTC CAG GAG CAG TCC       1008
Asn Arg Thr Leu His Val Ser Met Phe Gln Val Val Gln Glu Gln Ser
                160                 165                 170

AAC AGG GAG TCT GAC TTG TTC TTT TTG GAT CTT CAG ACG CTC CGA GCT       1056
Asn Arg Glu Ser Asp Leu Phe Phe Leu Asp Leu Gln Thr Leu Arg Ala
175                 180                 185
```

```
GGA GAC GAG GGC TGG CTG GTG CTG GAT GTC ACA GCA GCC AGT GAC TGC        1104
Gly Asp Glu Gly Trp Leu Val Leu Asp Val Thr Ala Ala Ser Asp Cys
190                 195                 200                 205

TGG TTG CTG AAG CGT CAC AAG GAC CTG GGA CTC CGC CTC TAT GTG GAG        1152
Trp Leu Leu Lys Arg His Lys Asp Leu Gly Leu Arg Leu Tyr Val Glu
                210                 215                 220

ACT GAG GAC GGG CAC AGC GTG GAT CCT GGC CTG GCC GGC CTG CTG GGT        1200
Thr Glu Asp Gly His Ser Val Asp Pro Gly Leu Ala Gly Leu Leu Gly
            225                 230                 235

CAA CGG GCC CCA CGC TCC CAA CAG CCT TTC GTG GTC ACT TTC TTC AGG        1248
Gln Arg Ala Pro Arg Ser Gln Gln Pro Phe Val Val Thr Phe Phe Arg
        240                 245                 250

GCC AGT CCG AGT CCC ATC CGC ACC CCT CGG GCA GTG AGG CCA CTG AGG        1296
Ala Ser Pro Ser Pro Ile Arg Thr Pro Arg Ala Val Arg Pro Leu Arg
    255                 260                 265

AGG AGG CAG CCG AAG AAA AGC AAC GAG CTG CCG CAG GCC AAC CGA CTC        1344
Arg Arg Gln Pro Lys Lys Ser Asn Glu Leu Pro Gln Ala Asn Arg Leu
270                 275                 280                 285

CCA GGG ATC TTT GAT GAC GTC CAC GGC TCC CAC GGC CGG CAG GTC TGC        1392
Pro Gly Ile Phe Asp Asp Val His Gly Ser His Gly Arg Gln Val Cys
                290                 295                 300

CGT CGG CAC GAG CTC TAC GTC AGC TTC CAG GAC CTC GGC TGG CTG GAC        1440
Arg Arg His Glu Leu Tyr Val Ser Phe Gln Asp Leu Gly Trp Leu Asp
            305                 310                 315

TGG GTC ATC GCT CCC CAA GGC TAC TCG GCC TAT TAC TGT GAG GGG GAG        1488
Trp Val Ile Ala Pro Gln Gly Tyr Ser Ala Tyr Tyr Cys Glu Gly Glu
        320                 325                 330

TGC TCC TTC CCA CTG GAC TCC TGC ATG AAT GCC ACC AAC CAC GCC ATC        1536
Cys Ser Phe Pro Leu Asp Ser Cys Met Asn Ala Thr Asn His Ala Ile
    335                 340                 345

CTG CAG TCC CTG GTG CAC CTG ATG AAG CCA AAC GCA GTC CCC AAG GCG        1584
Leu Gln Ser Leu Val His Leu Met Lys Pro Asn Ala Val Pro Lys Ala
350                 355                 360                 365

TGC TGT GCA CCC ACC AAG CTG AGC GCC ACC TCT GTG CTC TAC TAT GAC        1632
Cys Cys Ala Pro Thr Lys Leu Ser Ala Thr Ser Val Leu Tyr Tyr Asp
                370                 375                 380

AGC AGC AAC AAC GTC ATC CTG CGC AAA GCC CGC AAC ATG GTG GTC AAG        1680
Ser Ser Asn Asn Val Ile Leu Arg Lys Ala Arg Asn Met Val Val Lys
            385                 390                 395

GCC TGC GGC TGC CAC T GAGTCAGCCC GCCCAGCCCT ACTGCAG                    1723
Ala Cys Gly Cys His
            400

(2) INFORMATION FOR SEQ ID NO:21:

(i) SEQUENCE CHARACTERISTICS:
        (A) LENGTH: 402 amino acids
        (B) TYPE: amino acid
        (D) TOPOLOGY: linear (ii) MOLECULE TYPE: protein (xi) SEQUENCE DESCRIPTION: SEQ ID NO:21:

Met Thr Ala Leu Pro Gly Pro Leu Trp Leu Leu Gly Leu Ala Leu Cys
1               5                   10                  15

Ala Leu Gly Gly Gly Gly Pro Gly Leu Arg Pro Pro Gly Cys Pro
            20                  25                  30

Gln Arg Arg Leu Gly Ala Arg Glu Arg Arg Asp Val Gln Arg Glu Ile
            35                  40                  45

Leu Ala Val Leu Gly Leu Pro Gly Arg Pro Arg Pro Arg Ala Pro Pro
        50                  55                  60
```

```
Ala Ala Ser Arg Leu Pro Ala Ser Ala Pro Leu Phe Met Leu Asp Leu
 65                  70                  75                  80

Tyr His Ala Met Ala Gly Asp Asp Glu Asp Gly Ala Pro Ala Glu
                 85                  90                  95

Arg Arg Leu Gly Arg Ala Asp Leu Val Met Ser Phe Val Asn Met Val
                100                 105                 110

Glu Arg Asp Arg Ala Leu Gly His Gln Glu Pro His Trp Lys Glu Phe
            115                 120                 125

Arg Phe Asp Leu Thr Gln Ile Pro Ala Gly Glu Ala Val Thr Ala Ala
        130                 135                 140

Glu Phe Arg Ile Tyr Lys Val Pro Ser Ile His Leu Leu Asn Arg Thr
145                 150                 155                 160

Leu His Val Ser Met Phe Gln Val Val Gln Glu Gln Ser Asn Arg Glu
                165                 170                 175

Ser Asp Leu Phe Phe Leu Asp Leu Gln Thr Leu Arg Ala Gly Asp Glu
            180                 185                 190

Gly Trp Leu Val Leu Asp Val Thr Ala Ala Ser Asp Cys Trp Leu Leu
        195                 200                 205

Lys Arg His Lys Asp Leu Gly Leu Arg Leu Tyr Val Glu Thr Glu Asp
210                 215                 220

Gly His Ser Val Asp Pro Gly Leu Ala Gly Leu Leu Gly Gln Arg Ala
225                 230                 235                 240

Pro Arg Ser Gln Gln Pro Phe Val Val Thr Phe Phe Arg Ala Ser Pro
                245                 250                 255

Ser Pro Ile Arg Thr Pro Arg Ala Val Arg Pro Leu Arg Arg Arg Gln
            260                 265                 270

Pro Lys Lys Ser Asn Glu Leu Pro Gln Ala Asn Arg Leu Pro Gly Ile
        275                 280                 285

Phe Asp Asp Val His Gly Ser His Gly Arg Gln Val Cys Arg Arg His
290                 295                 300

Glu Leu Tyr Val Ser Phe Gln Asp Leu Gly Trp Leu Asp Trp Val Ile
305                 310                 315                 320

Ala Pro Gln Gly Tyr Ser Ala Tyr Tyr Cys Glu Gly Glu Cys Ser Phe
                325                 330                 335

Pro Leu Asp Ser Cys Met Asn Ala Thr Asn His Ala Ile Leu Gln Ser
            340                 345                 350

Leu Val His Leu Met Lys Pro Asn Ala Val Pro Lys Ala Cys Cys Ala
        355                 360                 365

Pro Thr Lys Leu Ser Ala Thr Ser Val Leu Tyr Tyr Asp Ser Ser Asn
370                 375                 380

Asn Val Ile Leu Arg Lys Ala Arg Asn Met Val Val Lys Ala Cys Gly
385                 390                 395                 400

Cys His (2) INFORMATION FOR SEQ ID NO:22:

(i) SEQUENCE CHARACTERISTICS:
        (A) LENGTH: 1926 base pairs
        (B) TYPE: nucleic acid
        (C) STRANDEDNESS: single
        (D) TOPOLOGY: linear (vi) ORIGINAL SOURCE:
        (A) ORGANISM: MURIDAE
        (F) TISSUE TYPE: EMBRYO
```

(ix) FEATURE:
    (A) NAME/KEY: CDS
    (B) LOCATION: 93..1289
    (D) OTHER INFORMATION: /function= "OSTEOGENIC PROTEIN"
        /product= "mOP2-PP"
        /note= "mOP2 cDNA"

(xi) SEQUENCE DESCRIPTION: SEQ ID NO:22:

```
GCCAGGCACA GGTGCGCCGT CTGGTCCTCC CCGTCTGGCG TCAGCCGAGC CCGACCAGCT        60

ACCAGTGGAT GCGCGCCGGC TGAAAGTCCG AG ATG GCT ATG CGT CCC GGG CCA         113
                                    Met Ala Met Arg Pro Gly Pro
                                     1               5

CTC TGG CTA TTG GGC CTT GCT CTG TGC GCG CTG GGA GGC GGC CAC GGT         161
Leu Trp Leu Leu Gly Leu Ala Leu Cys Ala Leu Gly Gly Gly His Gly
        10              15                  20

CCG CGT CCC CCG CAC ACC TGT CCC CAG CGT CGC CTG GGA GCG CGC GAG         209
Pro Arg Pro Pro His Thr Cys Pro Gln Arg Arg Leu Gly Ala Arg Glu
    25              30                  35

CGC CGC GAC ATG CAG CGT GAA ATC CTG GCG GTG CTC GGG CTA CCG GGA         257
Arg Arg Asp Met Gln Arg Glu Ile Leu Ala Val Leu Gly Leu Pro Gly
 40              45                  50                      55

CGG CCC CGA CCC CGT GCA CAA CCC GCC GCT GCC CGG CAG CCA GCG TCC         305
Arg Pro Arg Pro Arg Ala Gln Pro Ala Ala Arg Gln Pro Ala Ser
            60                  65                  70

GCG CCC CTC TTC ATG TTG GAC CTA TAC CAC GCC ATG ACC GAT GAC GAC         353
Ala Pro Leu Phe Met Leu Asp Leu Tyr His Ala Met Thr Asp Asp Asp
            75                  80                  85

GAC GGC GGG CCA CCA CAG GCT CAC TTA GGC CGT GCC GAC CTG GTC ATG         401
Asp Gly Gly Pro Pro Gln Ala His Leu Gly Arg Ala Asp Leu Val Met
            90                  95                  100

AGC TTC GTC AAC ATG GTG GAA CGC GAC CGT ACC CTG GGC TAC CAG GAG         449
Ser Phe Val Asn Met Val Glu Arg Asp Arg Thr Leu Gly Tyr Gln Glu
    105                 110                 115

CCA CAC TGG AAG GAA TTC CAC TTT GAC CTA ACC CAG ATC CCT GCT GGG         497
Pro His Trp Lys Glu Phe His Phe Asp Leu Thr Gln Ile Pro Ala Gly
120                 125                 130                 135

GAG GCT GTC ACA GCT GCT GAG TTC CGG ATC TAC AAA GAA CCC AGC ACC         545
Glu Ala Val Thr Ala Ala Glu Phe Arg Ile Tyr Lys Glu Pro Ser Thr
            140                 145                 150

CAC CCG CTC AAC ACA ACC CTC CAC ATC AGC ATG TTC GAA GTG GTC CAA         593
His Pro Leu Asn Thr Thr Leu His Ile Ser Met Phe Glu Val Val Gln
            155                 160                 165

GAG CAC TCC AAC AGG GAG TCT GAC TTG TTC TTT TTG GAT CTT CAG ACG         641
Glu His Ser Asn Arg Glu Ser Asp Leu Phe Phe Leu Asp Leu Gln Thr
            170                 175                 180

CTC CGA TCT GGG GAC GAG GGC TGG CTG GTG CTG GAC ATC ACA GCA GCC         689
Leu Arg Ser Gly Asp Glu Gly Trp Leu Val Leu Asp Ile Thr Ala Ala
    185                 190                 195

AGT GAC CGA TGG CTG CTG AAC CAT CAC AAG GAC CTG GGA CTC CGC CTC         737
Ser Asp Arg Trp Leu Leu Asn His His Lys Asp Leu Gly Leu Arg Leu
200                 205                 210                 215

TAT GTG GAA ACC GCG GAT GGG CAC AGC ATG GAT CCT GGC CTG GCT GGT         785
Tyr Val Glu Thr Ala Asp Gly His Ser Met Asp Pro Gly Leu Ala Gly
            220                 225                 230

CTG CTT GGA CGA CAA GCA CCA CGC TCC AGA CAG CCT TTC ATG GTA ACC         833
Leu Leu Gly Arg Gln Ala Pro Arg Ser Arg Gln Pro Phe Met Val Thr
        235                 240                 245

TTC TTC AGG GCC AGC CAG AGT CCT GTG CGG GCC CCT CGG GCA GCG AGA         881
Phe Phe Arg Ala Ser Gln Ser Pro Val Arg Ala Pro Arg Ala Ala Arg
        250                 255                 260
```

```
CCA CTG AAG AGG AGG CAG CCA AAG AAA ACG AAC GAG CTT CCG CAC CCC        929
Pro Leu Lys Arg Arg Gln Pro Lys Lys Thr Asn Glu Leu Pro His Pro
    265                 270                 275

AAC AAA CTC CCA GGG ATC TTT GAT GAT GGC CAC GGT TCC CGC GGC AGA        977
Asn Lys Leu Pro Gly Ile Phe Asp Asp Gly His Gly Ser Arg Gly Arg
280                 285                 290                 295

GAG GTT TGC CGC AGG CAT GAG CTC TAC GTC AGC TTC CGT GAC CTT GGC       1025
Glu Val Cys Arg Arg His Glu Leu Tyr Val Ser Phe Arg Asp Leu Gly
                300                 305                 310

TGG CTG GAC TGG GTC ATC GCC CCC CAG GGC TAC TCT GCC TAT TAC TGT       1073
Trp Leu Asp Trp Val Ile Ala Pro Gln Gly Tyr Ser Ala Tyr Tyr Cys
            315                 320                 325

GAG GGG GAG TGT GCT TTC CCA CTG GAC TCC TGT ATG AAC GCC ACC AAC       1121
Glu Gly Glu Cys Ala Phe Pro Leu Asp Ser Cys Met Asn Ala Thr Asn
        330                 335                 340

CAT GCC ATC TTG CAG TCT CTG GTG CAC CTG ATG AAG CCA GAT GTT GTC       1169
His Ala Ile Leu Gln Ser Leu Val His Leu Met Lys Pro Asp Val Val
    345                 350                 355

CCC AAG GCA TGC TGT GCA CCC ACC AAA CTG AGT GCC ACC TCT GTG CTG       1217
Pro Lys Ala Cys Cys Ala Pro Thr Lys Leu Ser Ala Thr Ser Val Leu
360                 365                 370                 375

TAC TAT GAC AGC AGC AAC AAT GTC ATC CTG CGT AAA CAC CGT AAC ATG       1265
Tyr Tyr Asp Ser Ser Asn Asn Val Ile Leu Arg Lys His Arg Asn Met
                380                 385                 390

GTG GTC AAG GCC TGT GGC TGC CAC TGAGGCCCCG CCCAGCATCC TGCTTCTACT      1319
Val Val Lys Ala Cys Gly Cys His
            395

ACCTTACCAT CTGGCCGGGC CCCTCTCCAG AGGCAGAAAC CCTTCTATGT TATCATAGCT     1379

CAGACAGGGG CAATGGGAGG CCCTTCACTT CCCCTGGCCA CTTCCTGCTA AAATTCTGGT     1439

CTTTCCCAGT TCCTCTGTCC TTCATGGGGT TTCGGGGCTA TCACCCCGCC CTCTCCATCC     1499

TCCTACCCCA AGCATAGACT GAATGCACAC AGCATCCCAG AGCTATGCTA ACTGAGAGGT     1559

CTGGGGTCAG CACTGAAGGC CCACATGAGG AAGACTGATC CTTGGCCATC CTCAGCCCAC     1619

AATGGCAAAT TCTGGATGGT CTAAGAAGGC CCTGGAATTC TAAACTAGAT GATCTGGGCT     1679

CTCTGCACCA TTCATTGTGG CAGTTGGGAC ATTTTTAGGT ATAACAGACA CATACACTTA     1739

GATCAATGCA TCGCTGTACT CCTTGAAATC AGAGCTAGCT TGTTAGAAAA AGAATCAGAG     1799

CCAGGTATAG CGGTGCATGT CATTAATCCC AGCGCTAAAG AGACAGAGAC AGGAGAATCT     1859

CTGTGAGTTC AAGGCCACAT AGAAAGAGCC TGTCTCGGGA GCAGGAAAAA AAAAAAAAAC     1919

GGAATTC                                                               1926
```

(2) INFORMATION FOR SEQ ID NO:23:

(i) SEQUENCE CHARACTERISTICS:
        (A) LENGTH: 399 amino acids
        (B) TYPE: amino acid
        (D) TOPOLOGY: linear (ii) MOLECULE TYPE: protein (xi) SEQUENCE DESCRIPTION: SEQ ID NO:23:

```
Met Ala Met Arg Pro Gly Pro Leu Trp Leu Leu Gly Leu Ala Leu Cys
1               5                   10                  15

Ala Leu Gly Gly Gly His Gly Pro Arg Pro Pro His Thr Cys Pro Gln
                20                  25                  30

Arg Arg Leu Gly Ala Arg Glu Arg Arg Asp Met Gln Arg Glu Ile Leu
        35                  40                  45
```

```
Ala Val Leu Gly Leu Pro Gly Arg Pro Arg Pro Arg Ala Gln Pro Ala
 50                  55                  60
Ala Ala Arg Gln Pro Ala Ser Ala Pro Leu Phe Met Leu Asp Leu Tyr
 65                  70                  75                  80
His Ala Met Thr Asp Asp Asp Gly Gly Pro Pro Gln Ala His Leu
                 85                  90                  95
Gly Arg Ala Asp Leu Val Met Ser Phe Val Asn Met Val Glu Arg Asp
                100                 105                 110
Arg Thr Leu Gly Tyr Gln Glu Pro His Trp Lys Glu Phe His Phe Asp
                115                 120                 125
Leu Thr Gln Ile Pro Ala Gly Glu Ala Val Thr Ala Ala Glu Phe Arg
    130                 135                 140
Ile Tyr Lys Glu Pro Ser Thr His Pro Leu Asn Thr Thr Leu His Ile
145                 150                 155                 160
Ser Met Phe Glu Val Val Gln Glu His Ser Asn Arg Glu Ser Asp Leu
                165                 170                 175
Phe Phe Leu Asp Leu Gln Thr Leu Arg Ser Asp Glu Gly Trp Leu
                180                 185                 190
Val Leu Asp Ile Thr Ala Ala Ser Asp Arg Trp Leu Leu Asn His His
    195                 200                 205
Lys Asp Leu Gly Leu Arg Leu Tyr Val Glu Thr Ala Asp Gly His Ser
    210                 215                 220
Met Asp Pro Gly Leu Ala Gly Leu Leu Gly Arg Gln Ala Pro Arg Ser
225                 230                 235                 240
Arg Gln Pro Phe Met Val Thr Phe Phe Arg Ala Ser Gln Ser Pro Val
                245                 250                 255
Arg Ala Pro Arg Ala Ala Arg Pro Leu Lys Arg Arg Gln Pro Lys Lys
                260                 265                 270
Thr Asn Glu Leu Pro His Pro Asn Lys Leu Pro Gly Ile Phe Asp Asp
    275                 280                 285
Gly His Gly Ser Arg Gly Arg Glu Val Cys Arg Arg His Glu Leu Tyr
    290                 295                 300
Val Ser Phe Arg Asp Leu Gly Trp Leu Asp Trp Val Ile Ala Pro Gln
305                 310                 315                 320
Gly Tyr Ser Ala Tyr Tyr Cys Glu Gly Glu Cys Ala Phe Pro Leu Asp
                325                 330                 335
Ser Cys Met Asn Ala Thr Asn His Ala Ile Leu Gln Ser Leu Val His
                340                 345                 350
Leu Met Lys Pro Asp Val Val Pro Lys Ala Cys Cys Ala Pro Thr Lys
    355                 360                 365
Leu Ser Ala Thr Ser Val Leu Tyr Tyr Asp Ser Ser Asn Asn Val Ile
    370                 375                 380
Leu Arg Lys His Arg Asn Met Val Val Lys Ala Cys Gly Cys His
385                 390                 395
```

(2) INFORMATION FOR SEQ ID NO:24:

(i) SEQUENCE CHARACTERISTICS:
        (A) LENGTH: 1368 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS -continued (B) LOCATION: 1..1368

(xi) SEQUENCE DESCRIPTION: SEQ ID NO:24:

| | | | | | | | | | | | | | | | | |
|---|---|---|---|---|---|---|---|---|---|---|---|---|---|---|---|---|
| ATG | TCG | GGA | CTG | CGA | AAC | ACC | TCG | GAG | GCC | GTT | GCA | GTG | CTC | GCC | TCC | 48 |
| Met | Ser | Gly | Leu | Arg | Asn | Thr | Ser | Glu | Ala | Val | Ala | Val | Leu | Ala | Ser | |
| 1 | | | | 5 | | | | | 10 | | | | | 15 | | |
| CTG | GGA | CTC | GGA | ATG | GTT | CTC | CTC | ATG | TTC | GTG | GCG | ACC | ACG | CCG | CCG | 96 |
| Leu | Gly | Leu | Gly | Met | Val | Leu | Leu | Met | Phe | Val | Ala | Thr | Thr | Pro | Pro | |
| | | | 20 | | | | | 25 | | | | | 30 | | | |
| GCC | GTT | GAG | GCC | ACC | CAG | TCG | GGG | ATT | TAC | ATA | GAC | AAC | GGC | AAG | GAC | 144 |
| Ala | Val | Glu | Ala | Thr | Gln | Ser | Gly | Ile | Tyr | Ile | Asp | Asn | Gly | Lys | Asp | |
| | | 35 | | | | | 40 | | | | | 45 | | | | |
| CAG | ACG | ATC | ATG | CAC | AGA | GTG | CTG | AGC | GAG | GAC | GAC | AAG | CTG | GAC | GTC | 192 |
| Gln | Thr | Ile | Met | His | Arg | Val | Leu | Ser | Glu | Asp | Asp | Lys | Leu | Asp | Val | |
| | 50 | | | | | 55 | | | | | 60 | | | | | |
| TCG | TAC | GAG | ATC | CTC | GAG | TTC | CTG | GGC | ATC | GCC | GAA | CGG | CCG | ACG | CAC | 240 |
| Ser | Tyr | Glu | Ile | Leu | Glu | Phe | Leu | Gly | Ile | Ala | Glu | Arg | Pro | Thr | His | |
| 65 | | | | | 70 | | | | | 75 | | | | | 80 | |
| CTG | AGC | AGC | CAC | CAG | TTG | TCG | CTG | AGG | AAG | TCG | GCT | CCC | AAG | TTC | CTG | 288 |
| Leu | Ser | Ser | His | Gln | Leu | Ser | Leu | Arg | Lys | Ser | Ala | Pro | Lys | Phe | Leu | |
| | | | | 85 | | | | | 90 | | | | | 95 | | |
| CTG | GAC | GTC | TAC | CAC | CGC | ATC | ACG | GCG | GAG | GAG | GGT | CTC | AGC | GAT | CAG | 336 |
| Leu | Asp | Val | Tyr | His | Arg | Ile | Thr | Ala | Glu | Glu | Gly | Leu | Ser | Asp | Gln | |
| | | | 100 | | | | | 105 | | | | | 110 | | | |
| GAT | GAG | GAC | GAC | GAC | TAC | GAA | CGC | GGC | CAT | CGG | TCC | AGG | AGG | AGC | GCC | 384 |
| Asp | Glu | Asp | Asp | Asp | Tyr | Glu | Arg | Gly | His | Arg | Ser | Arg | Arg | Ser | Ala | |
| | | 115 | | | | | 120 | | | | | 125 | | | | |
| GAC | CTC | GAG | GAG | GAT | GAG | GGC | GAG | CAG | CAG | AAG | AAC | TTC | ATC | ACC | GAC | 432 |
| Asp | Leu | Glu | Glu | Asp | Glu | Gly | Glu | Gln | Gln | Lys | Asn | Phe | Ile | Thr | Asp | |
| | 130 | | | | | 135 | | | | | 140 | | | | | |
| CTG | GAC | AAG | CGG | GCC | ATC | GAC | GAG | AGC | GAC | ATC | ATC | ATG | ACC | TTC | CTG | 480 |
| Leu | Asp | Lys | Arg | Ala | Ile | Asp | Glu | Ser | Asp | Ile | Ile | Met | Thr | Phe | Leu | |
| 145 | | | | | 150 | | | | | 155 | | | | | 160 | |
| AAC | AAG | CGC | CAC | CAC | AAT | GTG | GAC | GAA | CTG | CGT | CAC | GAG | CAC | GGC | CGT | 528 |
| Asn | Lys | Arg | His | His | Asn | Val | Asp | Glu | Leu | Arg | His | Glu | His | Gly | Arg | |
| | | | | 165 | | | | | 170 | | | | | 175 | | |
| CGC | CTG | TGG | TTC | GAC | GTC | TCC | AAC | GTG | CCC | AAC | GAC | AAC | TAC | CTG | GTG | 576 |
| Arg | Leu | Trp | Phe | Asp | Val | Ser | Asn | Val | Pro | Asn | Asp | Asn | Tyr | Leu | Val | |
| | | | 180 | | | | | 185 | | | | | 190 | | | |
| ATG | GCC | GAG | CTG | CGC | ATC | TAT | CAG | AAC | GCC | AAC | GAG | GGC | AAG | TGG | CTG | 624 |
| Met | Ala | Glu | Leu | Arg | Ile | Tyr | Gln | Asn | Ala | Asn | Glu | Gly | Lys | Trp | Leu | |
| | | 195 | | | | | 200 | | | | | 205 | | | | |
| ACC | GCC | AAC | AGG | GAG | TTC | ACC | ATC | ACG | GTA | TAC | GCC | ATT | GGC | ACC | GGC | 672 |
| Thr | Ala | Asn | Arg | Glu | Phe | Thr | Ile | Thr | Val | Tyr | Ala | Ile | Gly | Thr | Gly | |
| | 210 | | | | | 215 | | | | | 220 | | | | | |
| ACG | CTG | GGC | CAG | CAC | ACC | ATG | GAG | CCG | CTG | TCC | TCG | GTG | AAC | ACC | ACC | 720 |
| Thr | Leu | Gly | Gln | His | Thr | Met | Glu | Pro | Leu | Ser | Ser | Val | Asn | Thr | Thr | |
| 225 | | | | | 230 | | | | | 235 | | | | | 240 | |
| GGG | GAC | TAC | GTG | GGC | TGG | TTG | GAG | CTC | AAC | GTG | ACC | GAG | GGC | CTG | CAC | 768 |
| Gly | Asp | Tyr | Val | Gly | Trp | Leu | Glu | Leu | Asn | Val | Thr | Glu | Gly | Leu | His | |
| | | | | 245 | | | | | 250 | | | | | 255 | | |
| GAG | TGG | CTG | GTC | AAG | TCG | AAG | GAC | AAT | CAT | GGC | ATC | TAC | ATT | GGA | GCA | 816 |
| Glu | Trp | Leu | Val | Lys | Ser | Lys | Asp | Asn | His | Gly | Ile | Tyr | Ile | Gly | Ala | |
| | | | 260 | | | | | 265 | | | | | 270 | | | |
| CAC | GCT | GTC | AAC | CGA | CCC | GAC | CGC | GAG | GTG | AAG | CTG | GAC | GAC | ATT | GGA | 864 |
| His | Ala | Val | Asn | Arg | Pro | Asp | Arg | Glu | Val | Lys | Leu | Asp | Asp | Ile | Gly | |
| | | 275 | | | | | 280 | | | | | 285 | | | | |
| CTG | ATC | CAC | CGC | AAG | GTG | GAC | GAC | GAG | TTC | CAG | CCC | TTC | ATG | ATC | GGC | 912 |
| Leu | Ile | His | Arg | Lys | Val | Asp | Asp | Glu | Phe | Gln | Pro | Phe | Met | Ile | Gly | |
| | 290 | | | | | 295 | | | | | 300 | | | | | |

| | | | | | | | | | | | | | | |
|---|---|---|---|---|---|---|---|---|---|---|---|---|---|---|
| TTC | TTC | CGC | GGA | CCG | GAG | CTG | ATC | AAG | GCG | ACG | GCC | CAC | AGC | AGC | CAC | 960 |
| Phe | Phe | Arg | Gly | Pro | Glu | Leu | Ile | Lys | Ala | Thr | Ala | His | Ser | Ser | His | |
| 305 | | | | 310 | | | | | 315 | | | | | 320 | | |

```
TTC TTC CGC GGA CCG GAG CTG ATC AAG GCG ACG GCC CAC AGC AGC CAC          960
Phe Phe Arg Gly Pro Glu Leu Ile Lys Ala Thr Ala His Ser Ser His
305                 310                 315                 320

CAC AGG AGC AAG CGA AGC GCC AGC CAT CCA CGC AAG CGC AAG AAG TCG         1008
His Arg Ser Lys Arg Ser Ala Ser His Pro Arg Lys Arg Lys Lys Ser
                325                 330                 335

GTG TCG CCC AAC AAC GTG CCG CTG CTG GAA CCG ATG GAG AGC ACG CGC         1056
Val Ser Pro Asn Asn Val Pro Leu Leu Glu Pro Met Glu Ser Thr Arg
                340                 345                 350

AGC TGC CAG ATG CAG ACC CTG TAC ATA GAC TTC AAG GAT CTG GGC TGG         1104
Ser Cys Gln Met Gln Thr Leu Tyr Ile Asp Phe Lys Asp Leu Gly Trp
                355                 360                 365

CAT GAC TGG ATC ATC GCA CCA GAG GGC TAT GGC GCC TTC TAC TGC AGC         1152
His Asp Trp Ile Ile Ala Pro Glu Gly Tyr Gly Ala Phe Tyr Cys Ser
370                 375                 380

GGC GAG TGC AAT TTC CCG CTC AAT GCG CAC ATG AAC GCC ACG AAC CAT         1200
Gly Glu Cys Asn Phe Pro Leu Asn Ala His Met Asn Ala Thr Asn His
385                 390                 395                 400

GCG ATC GTC CAG ACC CTG GTC CAC CTG CTG GAG CCC AAG AAG GTG CCC         1248
Ala Ile Val Gln Thr Leu Val His Leu Leu Glu Pro Lys Lys Val Pro
                405                 410                 415

AAG CCC TGC TGC GCT CCG ACC AGG CTG GGA GCA CTA CCC GTT CTG TAC         1296
Lys Pro Cys Cys Ala Pro Thr Arg Leu Gly Ala Leu Pro Val Leu Tyr
                420                 425                 430

CAC CTG AAC GAC GAG AAT GTG AAC CTG AAA AAG TAT AGA AAC ATG ATT         1344
His Leu Asn Asp Glu Asn Val Asn Leu Lys Lys Tyr Arg Asn Met Ile
                435                 440                 445

GTG AAA TCC TGC GGG TGC CAT TGA                                         1368
Val Lys Ser Cys Gly Cys His
    450                 455
```

(2) INFORMATION FOR SEQ ID NO:25:

(i) SEQUENCE CHARACTERISTICS:
        (A) LENGTH: 455 amino acids
        (B) TYPE: amino acid
        (D) TOPOLOGY: linear (ii) MOLECULE TYPE: protein (xi) SEQUENCE DESCRIPTION: SEQ ID NO:25:

```
Met Ser Gly Leu Arg Asn Thr Ser Glu Ala Val Ala Val Leu Ala Ser
1               5                   10                  15

Leu Gly Leu Gly Met Val Leu Leu Met Phe Val Ala Thr Thr Pro Pro
                20                  25                  30

Ala Val Glu Ala Thr Gln Ser Gly Ile Tyr Ile Asp Asn Gly Lys Asp
            35                  40                  45

Gln Thr Ile Met His Arg Val Leu Ser Glu Asp Asp Lys Leu Asp Val
        50                  55                  60

Ser Tyr Glu Ile Leu Glu Phe Leu Gly Ile Ala Glu Arg Pro Thr His
65                  70                  75                  80

Leu Ser Ser His Gln Leu Ser Leu Arg Lys Ser Ala Pro Lys Phe Leu
                85                  90                  95

Leu Asp Val Tyr His Arg Ile Thr Ala Glu Glu Gly Leu Ser Asp Gln
                100                 105                 110

Asp Glu Asp Asp Asp Tyr Glu Arg Gly His Arg Ser Arg Arg Ser Ala
            115                 120                 125

Asp Leu Glu Glu Asp Glu Gly Glu Gln Gln Lys Asn Phe Ile Thr Asp
        130                 135                 140
```

```
Leu Asp Lys Arg Ala Ile Asp Glu Ser Asp Ile Ile Met Thr Phe Leu
145                 150                 155                 160

Asn Lys Arg His His Asn Val Asp Glu Leu Arg His Glu His Gly Arg
                165                 170                 175

Arg Leu Trp Phe Asp Val Ser Asn Val Pro Asn Asp Asn Tyr Leu Val
            180                 185                 190

Met Ala Glu Leu Arg Ile Tyr Gln Asn Ala Asn Glu Gly Lys Trp Leu
        195                 200                 205

Thr Ala Asn Arg Glu Phe Thr Ile Thr Val Tyr Ala Ile Gly Thr Gly
210                 215                 220

Thr Leu Gly Gln His Thr Met Glu Pro Leu Ser Ser Val Asn Thr Thr
225                 230                 235                 240

Gly Asp Tyr Val Gly Trp Leu Glu Leu Asn Val Thr Glu Gly Leu His
                245                 250                 255

Glu Trp Leu Val Lys Ser Lys Asp Asn His Gly Ile Tyr Ile Gly Ala
            260                 265                 270

His Ala Val Asn Arg Pro Asp Arg Glu Val Lys Leu Asp Asp Ile Gly
        275                 280                 285

Leu Ile His Arg Lys Val Asp Asp Glu Phe Gln Pro Phe Met Ile Gly
290                 295                 300

Phe Phe Arg Gly Pro Glu Leu Ile Lys Ala Thr Ala His Ser Ser His
305                 310                 315                 320

His Arg Ser Lys Arg Ser Ala Ser His Pro Arg Lys Arg Lys Lys Ser
                325                 330                 335

Val Ser Pro Asn Asn Val Pro Leu Leu Glu Pro Met Glu Ser Thr Arg
            340                 345                 350

Ser Cys Gln Met Gln Thr Leu Tyr Ile Asp Phe Lys Asp Leu Gly Trp
        355                 360                 365

His Asp Trp Ile Ile Ala Pro Glu Gly Tyr Gly Ala Phe Tyr Cys Ser
370                 375                 380

Gly Glu Cys Asn Phe Pro Leu Asn Ala His Met Asn Ala Thr Asn His
385                 390                 395                 400

Ala Ile Val Gln Thr Leu Val His Leu Leu Glu Pro Lys Lys Val Pro
                405                 410                 415

Lys Pro Cys Cys Ala Pro Thr Arg Leu Gly Ala Leu Pro Val Leu Tyr
            420                 425                 430

His Leu Asn Asp Glu Asn Val Asn Leu Lys Lys Tyr Arg Asn Met Ile
        435                 440                 445

Val Lys Ser Cys Gly Cys His
450                 455
```

(2) INFORMATION FOR SEQ ID NO:26:

(i) SEQUENCE CHARACTERISTICS:
        (A) LENGTH: 104 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..104
        (D) OTHER INFORMATION: /note= "BMP3"

(xi) SEQUENCE DESCRIPTION: SEQ ID NO:26:

-continued

```
Cys Ala Arg Arg Tyr Leu Lys Val Asp Phe Ala Asp Ile Gly Trp Ser
1               5                   10                  15

Glu Trp Ile Ile Ser Pro Lys Ser Phe Asp Ala Tyr Tyr Cys Ser Gly
                20              25                  30

Ala Cys Gln Phe Pro Met Pro Lys Ser Leu Lys Pro Ser Asn His Ala
            35              40                  45

Thr Ile Gln Ser Ile Val Ala Arg Ala Val Gly Val Val Pro Gly Ile
        50                  55                  60

Pro Glu Pro Cys Cys Val Pro Glu Lys Met Ser Ser Leu Ser Ile Leu
65              70                  75                      80

Phe Phe Asp Glu Asn Lys Asn Val Val Leu Lys Val Tyr Pro Asn Met
                85                  90                  95

Thr Val Glu Ser Cys Ala Cys Arg
            100
```

(2) INFORMATION FOR SEQ ID NO:27:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: HOMO SAPIENS (ix) FEATURE:
        (A) NAME/KEY: Protein
        (B) LOCATION: 1..102
        (D) OTHER INFORMATION: /note= "BMP5"

(xi) SEQUENCE DESCRIPTION: SEQ ID NO:27:

```
Cys Lys Lys His Glu Leu Tyr Val Ser Phe Arg Asp Leu Gly Trp Gln
1               5                   10                  15

Asp Trp Ile Ile Ala Pro Glu Gly Tyr Ala Ala Phe Tyr Cys Asp Gly
                20              25                  30

Glu Cys Ser Phe Pro Leu Asn Ala His Met Asn Ala Thr Asn His Ala
            35              40                  45

Ile Val Gln Thr Leu Val His Leu Met Phe Pro Asp His Val Pro Lys
        50                  55                  60

Pro Cys Cys Ala Pro Thr Lys Leu Asn Ala Ile Ser Val Leu Tyr Phe
65              70                  75                      80

Asp Asp Ser Ser Asn Val Ile Leu Lys Lys Tyr Arg Asn Met Val Val
                85                  90                  95

Arg Ser Cys Gly Cys His
            100
```

(2) INFORMATION FOR SEQ ID NO:28:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: HOMO SAPIENS (ix) FEATURE:
        (A) NAME/KEY: Protein (B) LOCATION: 1..102
                (D) OTHER INFORMATION: /note= "BMP6"

(xi) SEQUENCE DESCRIPTION: SEQ ID NO:28:

Cys Arg Lys His Glu Leu Tyr Val Ser Phe Gln Asp Leu Gly Trp Gln
    1               5                   10                  15

Asp Trp Ile Ile Ala Pro Lys Gly Tyr Ala Ala Asn Tyr Cys Asp Gly
                    20                  25                  30

Glu Cys Ser Phe Pro Leu Asn Ala His Met Asn Ala Thr Asn His Ala
                35                  40                  45

Ile Val Gln Thr Leu Val His Leu Met Asn Pro Glu Tyr Val Pro Lys
        50                  55                  60

Pro Cys Cys Ala Pro Thr Lys Leu Asn Ala Ile Ser Val Leu Tyr Phe
    65                  70                  75                  80

Asp Asp Asn Ser Asn Val Ile Leu Lys Lys Tyr Arg Trp Met Val Val
                    85                  90                  95

Arg Ala Cys Gly Cys His
                100

(2) INFORMATION FOR SEQ ID NO:29:

(i) SEQUENCE CHARACTERISTICS:
                (A) LENGTH: 102 amino acids
                (B) TYPE: amino acid
                (D) TOPOLOGY: linear (ii) MOLECULE TYPE: protein (ix) FEATURE:
                (A) NAME/KEY: Protein
                (B) LOCATION: 1..102
                (D) OTHER INFORMATION: /label= OPX
                    /note= "WHEREIN EACH XAA IS INDEPENDENTLY SELECTED
                    FROM A GROUP OF ONE OR MORE SPECIFIED AMINO ACIDS
                    AS DEFINED IN THE SPECIFICATION"

(xi) SEQUENCE DESCRIPTION: SEQ ID NO:29:

Cys Xaa Xaa His Glu Leu Tyr Val Xaa Phe Xaa Asp Leu Gly Trp Xaa
    1               5                   10                  15

Asp Trp Xaa Ile Ala Pro Xaa Gly Tyr Xaa Ala Tyr Tyr Cys Glu Gly
                    20                  25                  30

Glu Cys Xaa Phe Pro Leu Xaa Ser Xaa Met Asn Ala Thr Asn His Ala
                35                  40                  45

Ile Xaa Gln Xaa Leu Val His Xaa Xaa Xaa Pro Xaa Xaa Val Pro Lys
        50                  55                  60

Xaa Cys Cys Ala Pro Thr Xaa Leu Xaa Ala Xaa Ser Val Leu Tyr Xaa
    65                  70                  75                  80

Asp Xaa Ser Xaa Asn Val Xaa Leu Xaa Lys Xaa Arg Asn Met Val Val
                    85                  90                  95

Xaa Ala Cys Gly Cys His
                100

(2) INFORMATION FOR SEQ ID NO:30:

(i) SEQUENCE CHARACTERISTICS:
                (A) LENGTH: 97 amino acids
                (B) TYPE: amino acid
                (C) STRANDEDNESS: single
                (D) TOPOLOGY: linear (ii) MOLECULE TYPE: protein (ix) FEATURE:

(A) NAME/KEY: Protein
          (B) LOCATION: 1..97
          (D) OTHER INFORMATION: /label= GENERIC-SEQ5
              /note= "WHEREIN EACH XAA IS INDEPENDENTLY SELECTED
              FROM A GROUP OF ONE OR MORE SPECIFIED AMINO ACIDS
              AS DEFINED IN THE SPECIFICATION."

(xi) SEQUENCE DESCRIPTION: SEQ ID NO:30:

Leu Xaa Xaa Xaa Phe Xaa Xaa Xaa Gly Trp Xaa Xaa Trp Xaa Xaa
1               5                   10                  15

Pro Xaa Xaa Xaa Xaa Ala Xaa Tyr Cys Xaa Gly Xaa Cys Xaa Xaa Pro
                20              25              30

Xaa Xaa Xaa Xaa Xaa Xaa Xaa Asn His Ala Xaa Xaa Xaa Xaa Xaa
        35                  40              45

Xaa Xaa Xaa Xaa Xaa Xaa Xaa Xaa Xaa Xaa Cys Cys Xaa Pro
50                  55                  60

Xaa Xaa Xaa Xaa Xaa Xaa Xaa Xaa Leu Xaa Xaa Xaa Xaa Xaa Xaa
65                  70                  75                  80

Val Xaa Leu Xaa Xaa Xaa Xaa Xaa Met Xaa Val Xaa Xaa Cys Xaa Cys
            85                  90                  95

Xaa (2) INFORMATION FOR SEQ ID NO:31:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /label= GENERIC-SEQ6
              /note= "WHEREIN EACH XAA IS INDEPENDENTLY SELECTED
              FROM A GROUP OF ONE OR MORE SPECIFIED AMINO ACIDS
              AS DEFINED IN THE SPECIFICATION. "

(xi) SEQUENCE DESCRIPTION: SEQ ID NO:31:

Cys Xaa Xaa Xaa Xaa Leu Xaa Xaa Xaa Phe Xaa Xaa Xaa Gly Trp Xaa
1               5                   10                  15

Xaa Trp Xaa Xaa Xaa Pro Xaa Xaa Xaa Xaa Ala Xaa Tyr Cys Xaa Gly
                20                  25              30

Xaa Cys Xaa Xaa Pro Xaa Xaa Xaa Xaa Xaa Xaa Xaa Xaa Asn His Ala
        35                  40                  45

Xaa Xaa Xaa Xaa Xaa Xaa Xaa Xaa Xaa Xaa Xaa Xaa Xaa Xaa Xaa
50                  55                  60

Xaa Cys Cys Xaa Pro Xaa Xaa Xaa Xaa Xaa Xaa Xaa Leu Xaa Xaa
65              70                  75                  80

Xaa Xaa Xaa Xaa Xaa Val Xaa Leu Xaa Xaa Xaa Xaa Xaa Met Xaa Val
                85                  90                  95

Xaa Xaa Cys Xaa Cys Xaa
            100

(2) INFORMATION FOR SEQ ID NO:32:

(i) SEQUENCE CHARACTERISTICS:
        (A) LENGTH: 1247 base pairs
        (B) TYPE: nucleic acid
        (C) STRANDEDNESS: single
        (D) TOPOLOGY: linear -continued

```
      (ii) MOLECULE TYPE: cDNA (vi) ORIGINAL SOURCE:
           (A) ORGANISM: HOMO SAPIENS
           (F) TISSUE TYPE: BRAIN (ix) FEATURE:
           (A) NAME/KEY: CDS
           (B) LOCATION: 84..1199
           (D) OTHER INFORMATION: /product= "GDF-1"
               /note= "GDF-1 CDNA"

(xi) SEQUENCE DESCRIPTION: SEQ ID NO:32:

GGGGACACCG GCCCCGCCCT CAGCCCACTG GTCCCGGGCC GCCGCGGACC CTGCGCACTC         60

TCTGGTCATC GCCTGGGAGG AAG ATG CCA CCG CCG CAG CAA GGT CCC TGC           110
                         Met Pro Pro Pro Gln Gln Gly Pro Cys
                          1               5

GGC CAC CAC CTC CTC CTC CTC CTG GCC CTG CTG CTG CCC TCG CTG CCC         158
Gly His His Leu Leu Leu Leu Leu Ala Leu Leu Leu Pro Ser Leu Pro
 10              15                  20                  25

CTG ACC CGC GCC CCC GTG CCC CCA GGC CCA GCC GCC GCC CTG CTC CAG         206
Leu Thr Arg Ala Pro Val Pro Pro Gly Pro Ala Ala Ala Leu Leu Gln
              30                  35                  40

GCT CTA GGA CTG CGC GAT GAG CCC CAG GGT GCC CCC AGG CTC CGG CCG         254
Ala Leu Gly Leu Arg Asp Glu Pro Gln Gly Ala Pro Arg Leu Arg Pro
          45                  50                  55

GTT CCC CCG GTC ATG TGG CGC CTG TTT CGA CGC CGG GAC CCC CAG GAG         302
Val Pro Pro Val Met Trp Arg Leu Phe Arg Arg Arg Asp Pro Gln Glu
      60                  65                  70

ACC AGG TCT GGC TCG CGG CGG ACG TCC CCA GGG GTC ACC CTG CAA CCG         350
Thr Arg Ser Gly Ser Arg Arg Thr Ser Pro Gly Val Thr Leu Gln Pro
  75                  80                  85

TGC CAC GTG GAG GAG CTG GGG GTC GCC GGA AAC ATC GTG CGC CAC ATC         398
Cys His Val Glu Glu Leu Gly Val Ala Gly Asn Ile Val Arg His Ile
 90                  95                 100                 105

CCG GAC CGC GGT GCG CCC ACC CGG GCC TCG GAG CCT GTC TCG GCC GCG         446
Pro Asp Arg Gly Ala Pro Thr Arg Ala Ser Glu Pro Val Ser Ala Ala
                 110                 115                 120

GGG CAT TGC CCT GAG TGG ACA GTC GTC TTC GAC CTG TCG GCT GTG GAA         494
Gly His Cys Pro Glu Trp Thr Val Val Phe Asp Leu Ser Ala Val Glu
             125                 130                 135

CCC GCT GAG CGC CCG AGC CGG GCC CGC CTG GAG CTG CGT TTC GCG GCG         542
Pro Ala Glu Arg Pro Ser Arg Ala Arg Leu Glu Leu Arg Phe Ala Ala
         140                 145                 150

GCG GCG GCA GCC CCG GAG GGC GGC TGG GAG CTG AGC GTG GCG CAA             590
Ala Ala Ala Ala Pro Glu Gly Gly Trp Glu Leu Ser Val Ala Gln
     155                 160                 165

GCG GGC CAG GGC GCG GGC GCG GAC CCC GGG CCG GTG CTG CTC CGC CAG         638
Ala Gly Gln Gly Ala Gly Ala Asp Pro Gly Pro Val Leu Leu Arg Gln
170                 175                 180                 185

TTG GTG CCC GCC CTG GGG CCG CCA GTG CGC GCG GAG CTG CTG GGC GCC         686
Leu Val Pro Ala Leu Gly Pro Pro Val Arg Ala Glu Leu Leu Gly Ala
                 190                 195                 200

GCT TGG GCT CGC AAC GCC TCA TGG CCG CGC AGC CTC CGC CTG GCG CTG         734
Ala Trp Ala Arg Asn Ala Ser Trp Pro Arg Ser Leu Arg Leu Ala Leu
             205                 210                 215

GCG CTA CGC CCC CGG GCC CCT GCC GCC TGC GCG CGC CTG GCC GAG GCC         782
Ala Leu Arg Pro Arg Ala Pro Ala Ala Cys Ala Arg Leu Ala Glu Ala
         220                 225                 230

TCG CTG CTG CTG GTG ACC CTC GAC CCG CGC CTG TGC CAC CCC CTG GCC         830
Ser Leu Leu Leu Val Thr Leu Asp Pro Arg Leu Cys His Pro Leu Ala
```

```
                235                 240                 245
CGG CCG CGG CGC GAC GCC GAA CCC GTG TTG GGC GGC GGC CCC GGG GGC        878
Arg Pro Arg Arg Asp Ala Glu Pro Val Leu Gly Gly Gly Pro Gly Gly
250                 255                 260                 265

GCT TGT CGC GCG CGG CGG CTG TAC GTG AGC TTC CGC GAG GTG GGC TGG        926
Ala Cys Arg Ala Arg Arg Leu Tyr Val Ser Phe Arg Glu Val Gly Trp
                270                 275                 280

CAC CGC TGG GTC ATC GCG CCG CGC GGC TTC CTG GCC AAC TAC TGC CAG        974
His Arg Trp Val Ile Ala Pro Arg Gly Phe Leu Ala Asn Tyr Cys Gln
            285                 290                 295

GGT CAG TGC GCG CTG CCC GTC GCG CTG TCG GGG TCC GGG GGG CCG CCG       1022
Gly Gln Cys Ala Leu Pro Val Ala Leu Ser Gly Ser Gly Gly Pro Pro
        300                 305                 310

GCG CTC AAC CAC GCT GTG CTG CGC GCG CTC ATG CAC GCG GCC GCC CCG       1070
Ala Leu Asn His Ala Val Leu Arg Ala Leu Met His Ala Ala Ala Pro
    315                 320                 325

GGA GCC GCC GAC CTG CCC TGC TGC GTG CCC GCG CGC CTG TCG CCC ATC       1118
Gly Ala Ala Asp Leu Pro Cys Cys Val Pro Ala Arg Leu Ser Pro Ile
330                 335                 340                 345

TCC GTG CTC TTC TTT GAC AAC AGC GAC AAC GTG GTG CTG CGG CAG TAT       1166
Ser Val Leu Phe Phe Asp Asn Ser Asp Asn Val Val Leu Arg Gln Tyr
                350                 355                 360

GAG GAC ATG GTG GTG GAC GAG TGC GGC TGC CGC TAACCCGGGG CGGGCAGGGA     1219
Glu Asp Met Val Val Asp Glu Cys Gly Cys Arg
            365                 370

CCCGGGCCCA ACAATAAATG CCGCGTGG                                        1247

(2) INFORMATION FOR SEQ ID NO:33:

(i) SEQUENCE CHARACTERISTICS:
        (A) LENGTH: 372 amino acids
        (B) TYPE: amino acid
        (D) TOPOLOGY: linear (ii) MOLECULE TYPE: protein (xi) SEQUENCE DESCRIPTION: SEQ ID NO:33:

Met Pro Pro Gln Gln Gly Pro Cys Gly His His Leu Leu Leu Leu
 1               5                  10                  15

Leu Ala Leu Leu Leu Pro Ser Leu Pro Leu Thr Arg Ala Pro Val Pro
            20                  25                  30

Pro Gly Pro Ala Ala Ala Leu Leu Gln Ala Leu Gly Leu Arg Asp Glu
        35                  40                  45

Pro Gln Gly Ala Pro Arg Leu Arg Pro Val Pro Val Met Trp Arg
    50                  55                  60

Leu Phe Arg Arg Arg Asp Pro Gln Glu Thr Arg Ser Gly Ser Arg Arg
65                  70                  75                  80

Thr Ser Pro Gly Val Thr Leu Gln Pro Cys His Val Glu Glu Leu Gly
                85                  90                  95

Val Ala Gly Asn Ile Val Arg His Ile Pro Asp Arg Gly Ala Pro Thr
            100                 105                 110

Arg Ala Ser Glu Pro Val Ser Ala Gly His Cys Pro Glu Trp Thr
        115                 120                 125

Val Val Phe Asp Leu Ser Ala Val Glu Pro Ala Glu Arg Pro Ser Arg
    130                 135                 140

Ala Arg Leu Glu Leu Arg Phe Ala Ala Ala Ala Ala Pro Glu
145                 150                 155                 160

Gly Gly Trp Glu Leu Ser Val Ala Gln Ala Gly Gln Gly Ala Gly Ala
```

```
                    -continued
           165              170              175
Asp Pro Gly Pro Val Leu Leu Arg Gln Leu Val Pro Ala Leu Gly Pro
            180              185              190

Pro Val Arg Ala Glu Leu Leu Gly Ala Ala Trp Ala Arg Asn Ala Ser
            195              200              205

Trp Pro Arg Ser Leu Arg Leu Ala Leu Ala Leu Arg Pro Arg Ala Pro
            210              215              220

Ala Ala Cys Ala Arg Leu Ala Glu Ala Ser Leu Leu Leu Val Thr Leu
225              230              235              240

Asp Pro Arg Leu Cys His Pro Leu Ala Arg Pro Arg Arg Asp Ala Glu
            245              250              255

Pro Val Leu Gly Gly Gly Pro Gly Gly Ala Cys Arg Ala Arg Arg Leu
            260              265              270

Tyr Val Ser Phe Arg Glu Val Gly Trp His Arg Trp Val Ile Ala Pro
            275              280              285

Arg Gly Phe Leu Ala Asn Tyr Cys Gln Gly Gln Cys Ala Leu Pro Val
    290              295              300

Ala Leu Ser Gly Ser Gly Gly Pro Pro Ala Leu Asn His Ala Val Leu
305              310              315              320

Arg Ala Leu Met His Ala Ala Ala Pro Gly Ala Ala Asp Leu Pro Cys
            325              330              335

Cys Val Pro Ala Arg Leu Ser Pro Ile Ser Val Leu Phe Phe Asp Asn
            340              345              350

Ser Asp Asn Val Val Leu Arg Gln Tyr Glu Asp Met Val Val Asp Glu
    355              360              365

Cys Gly Cys Arg
    370
```

MORPHOGEN-INDUCED DENDRITIC GROWTH

CROSS REFERENCE TO RELATED APPLICATIONS

This is a continuation-in-part of application(s) Ser. No. 08/260,675, filed Jun. 16, 1994, now U.S. Pat. No. 6,800,603, as a file wrapper continuation of U.S. Ser. No. 08/126,100, filed Sep. 23, 1993, now abandoned as a file wrapper continuation of U.S. Ser. No. 07/922,813, filed Jul. 31, 1992, now abandoned as a continuation-in-part of U.S. Ser. No. 07/752,764, filed Aug. 30, 1991, now abandoned as a continuation-in-part of U.S. Ser. No. 07/667,274, filed Mar. 11, 1991, now abandoned. Prior related application U.S. Ser. No. 07/922,813, was also a continuation-in-part of U.S. Ser. No. 07/753,059, filed Aug. 30, 1991, now abandoned. The following is also a continuation-in-part of copending U.S. Ser. No. 07/971,091, filed Nov. 3, 1992, now abandoned as a continuation-in-part of U.S. Ser. No. 07/752,764, filed Aug. 30, 1991, now abandoned as a continuation-in-part of U.S. Ser. No. 07/667,274, filed Mar. 11, 1991, now abandoned. The following is also a continuation-in-part of U.S. Ser. No. 07/938,336, filed Aug. 28, 1992, now abandoned and of U.S. Ser. No. 07/938,337, also filed Aug. 28, 1992, now abandoned; both continuations-in-part are a continuation-in-part of U.S. Ser. No. 07/667,274, filed Mar. 11, 1991, now abandoned. The following is also a continuation-in-part of U.S. Ser. No. 07/938,021, filed Aug. 28, 1992, now abandoned which itself is a continuation-in-part of U.S. Ser. No. 07/752,861, filed Aug. 30, 1991, now abandoned, as a continuation-in-part of U.S. Ser. No. 07/667,274, filed Mar. 11, 1991, now abandoned. The following is also a continuation-in-part of U.S. Ser. No. 07/752,764, filed Aug. 30, 1991, now abandoned.

BACKGROUND OF THE INVENTION

The present invention relates to methods for enhancing the survival of neuronal cells in vivo and to methods, compositions and devices for maintaining neural pathways in vivo. More particularly, the invention provides methods for enhancing survival of neuronal cells at risk of dying, including methods for redifferentiating transformed cells of neural origin and methods for maintaining phenotypic expression of differentiated neuronal cells. The invention also provides means for repairing damaged neural pathways, including methods for stimulating axonal growth over extended distances, and methods for alleviating immunologically-related nerve tissue damage. In a particular embodiment, this invention provides a method for stimulating cell adhesion molecule expression in cells, and particularly nerve cell adhesion molecule expression in neurons. The invention further provides means for evaluating nerve tissue stasis and identifying neural dysfunction in a mammal. In other specific embodiments, the invention provides methods and compositions for promoting dendrite outgrowth of neural cells from both the central and peripheral nervous system.

The mammalian nervous system comprises a peripheral nervous system (PNS) and a central nervous system (CNS, comprising the brain and spinal cord), and is composed of two principal classes of cells: neurons and glial cells. The glial cells fill the spaces between neurons, nourishing them and modulating their function. Certain glial cells, such as Schwann cells in the PNS and oligodendrocytes in the CNS, also provide a protective myelin sheath that surrounds and protects neuronal axons, which are the processes that extend from the neuron cell body and through which the electric impulses of the neuron are transported. In the peripheral nervous system, the long axons of multiple neurons are bundled together to form a nerve or nerve fiber. These, in turn, may be combined into fascicles, wherein the nerve fibers form bundles embedded, together with the intraneural vascular supply, in a loose collagenous matrix bounded by a protective multilamellar sheath. In the central nervous system, the neuron cell bodies are visually distinguishable from their myelin-ensheathed processes, and are referenced in the art as grey and white matter, respectively.

During development, differentiating neurons from the central and peripheral nervous systems send out axons that must grow and make contact with specific target cells. In some cases, growing axons must cover enormous distances; some grow into the periphery, whereas others stay confined within the central nervous system. In mammals, this stage of neurogenesis is completed during the embryonic phase of life and neuronal cells do not multiply once they have fully differentiated.

In the vertebrate nervous system, dendrites are the primary site of synapse formation and neurons that lack dendrites typically receive fewer synaptic inputs than cells with complex dendritic arbors. Dendritic growth can be considered to occur in two phases: initial extension followed by elongation and ramification (Purves et al. (1988), 336 *Nature* 123–128). Some molecules, including neurotransmitters and hormones, have been shown to regulate expansion of an existing dendritic arbor. Much less is known, however, about the factors that influence earlier events and cause a neuron to initially form dendrites. In certain classes of neurons, initial dendritic sprouting occurs as part of an intrinsic development program which is relatively independent of trophic interactions (Dotti et al. (1988), 8 *J. Neurosci.* 1454–1468). In other classes of neurons, however, the regulation of the initial stages of dendritic growth appears to be quite different. For example, rat sympathetic neurons fail to form dendrites and extend only axons when they are cultured in the absence of nonneuronal cells. In contrast, co-culture with Schwann cells or astrocytes causes these neurons to form dendritic processes and to eventually generate a dendritic arbor which is comparable in size to that observed in situ (Tropea et al. (1988), 1 *Glia* 380–392). This change in cell shape is not observed when either fibroblasts or heart cells are co-cultured with Schwann cells. Thus, it would appear that specific trophic interactions are required to allow sympathetic neurons to form dendrites.

The foregoing observations have been taken to support a theory that the in situ environment specifies formation of a dendritic arbor. The environment in the vicinity of neural cells or developing neural processes is thus thought to include electromagnetic, electrochemical and/or biochemical fields or gradients which positively and negatively influence the extent and specificity of dendritic outgrowth as well as the formation of contacts (synapses) between dendrites and nerve cell bodies and axons. This theory, however, suffers from a paucity of identified mediators which have the capacity to cause neurons to sprout dendrites. Currently, the only molecule for which a role in the regulation of the initial stages of dendritic growth has been established is the nerve trophic factor, nerve growth factor (NGF). This growth factor can cause a subpopulation of nodose neurons to form dendrites in culture (de Koninck et al. (1993), 13 *J. Neurosci.* 577–585) and can enhance the growth of sympathetic dendrites when injected in situ (Snider, W. D. (1988), 8 *J. Neurosci.* 2628–2634, the teachings of which are herein incorporated by reference). NGF alone, however, does not support dendritic growth in cultures of sympathetic neurons (Bruckenstein and Higgins (1988), 128 *Dev. Biol.* 324–336, the teachings of which are herein incorporated by reference). It therefore appears that there are other molecules which can regulate the morphological development of neurons.

The neural pathways of a mammal are particularly at risk if neurons are subjected to mechanical or chemical trauma or to neuropathic degeneration sufficient to put the neurons that define the pathway at risk of dying. A host of neuropathies, some of which affect only a subpopulation or a system of neurons in the peripheral or central nervous systems (PNS or CNS) have been identified to date. The neuropathies, which may affect the neurons themselves or the associated glial cells, may result from cellular metabolic dysfunction, infection, exposure to toxic agents, autoimmunity dysfunction, malnutrition or ischemia. In some cases the cellular dysfunction is thought to induce cell death directly. In other cases, the neuropathy may induce sufficient tissue necrosis to stimulate the body's immune/inflammatory system and the mechanisms of the body's immune response to the initial neural injury then destroys the neurons and the pathway defined by these neurons.

Currently no satisfactory method exists to repair the damage caused by these neuropathies, which include multiple sclerosis, amyotrophic lateral sclerosis (ALS), Huntington's chorea, Alzheimer's disease, Parkinson's disease (parkinsonism), and metabolically derived disorders, such as hepatic encephalopathy. Current attempts to counteract the effects of severe traumatic or neural degenerative lesions of the brain and/or spinal cord have to date primarily involved implantation of embryonic neurons in an effort to replace functionally, or otherwise compensate for, lost or deficient neurons. Currently, however, human fetal cell transplantation research is severely restricted. Administration of nerve trophic factors such as nerve growth factor and insulin-like growth factor also have been suggested to stimulate neuronal growth within the CNS. (See, for example, Lundborg, (1987) *Acta Orthop. Scand.* 58: 145–169 and U.S. Pat. No. 5,093,317.) Administration of nerve trophic factors to the CNS requires bypassing the blood-brain barrier. The barrier may be overcome by direct infusion, or by modifying the molecule to enhance its transport across the barrier, as by chemical modification or conjugation, or by molecule truncation. Schwann cells also have been grafted to a site of a CNS lesion in an attempt to stimulate and maintain growth of damaged neuronal processes (Paino et al. (1991) *Exp. Neurology* 114(2): 254–257).

Where the damaged neural pathway results from CNS axonal damage, autologous peripheral nerve grafts have been used to bridge lesions in the central nervous system and to allow axons to make it back to their normal target area. In contrast to CNS neurons, neurons of the peripheral nervous system can extend new peripheral processes in response to axonal damage. This regenerative property of peripheral nervous system axons is thought to be sufficient to allow grafting of these segments to CNS axons. Successful grafting appears to be limited, however, by a number of factors, including the length of the CNS axonal lesion to be bypassed, and the distance of the graft sites from the CNS neuronal cell bodies, with successful grafts occurring near the cell body.

Within the peripheral nervous system, this cellular regenerative property of neurons has limited ability to repair function to a damaged neural pathway. Specifically, the new axons and dendrites extend randomly, and are often misdirected, making contact with inappropriate targets that can cause abnormal function. For example, if a motor nerve is damaged, regrowing axons may contact the wrong muscles, resulting in paralysis. In addition, where severed nerve processes result in a gap of longer than a few millimeters, e.g., greater than 10 millimeters (mm), appropriate nerve regeneration does not occur, either because the processes fail to grow the necessary distance, or because of misdirected axonal growth. Efforts to repair peripheral nerve damage by surgical means has met with mixed results, particularly where damage extends over a significant distance. In some cases, the suturing steps used to obtain proper alignment of severed nerve ends stimulates the formulation of scar tissue which is thought to inhibit axon regeneration. Even where scar tissue formation has been reduced, as with the use of nerve guidance channels or other tubular prostheses, successful regeneration generally still is limited to nerve damage of less than 10 millimeters in distance. In addition, the reparative ability of peripheral neurons is significantly inhibited where an injury or neuropathy affects the cell body itself or results in extensive degeneration of a distal axon.

Mammalian neural pathways also are at risk due to damage caused by neoplastic lesions. Neoplasias of both the neurons and glial cells have been identified. Transformed cells of neural origin generally lose their ability to behave as normal differentiated cells and can destroy neural pathways by loss of function. In addition, the proliferating tumors may induce lesions by distorting normal nerve tissue structure, inhibiting pathways by compressing nerves, inhibiting cerebrospinal fluid or blood supply flow, and/or by stimulating the body's immune response. Metastatic tumors, which are a significant cause of neoplastic lesions in the brain and spinal cord, also similarly may damage neural pathways and induce neuronal cell death.

One type of morphoregulatory molecule associated with neuronal cell growth, differentiation and development and the proper formation of cell—cell contacts (synapses) between neurons is the cell adhesion molecule ("CAM"), most notably the nerve cell adhesion molecule (N-CAM). CAMs belong to the immunoglobulin super-family and mediate cell—cell interactions in developing and adult tissues through homophilic binding, i.e., CAM-CAM binding on apposing cells. A number of different CAMs currently have been identified. Of these, the most thoroughly studied to date are N-CAM and L-CAM (liver cell adhesion molecules), both of which have been identified on all cells at early stages of development, as well as in different adult tissues. In neural tissue development, N-CAM expression is believed to be important in tissue organization, neuronal migration, nerve-muscle tissue adhesion, retinal formation, synaptogenesis, and neural degeneration. Reduced N-CAM expression also is thought to be associated with nerve dysfunction. For example, expression of at least one form of N-CAM, N-CAM-180, is reduced in a mouse dysmyelinating mutant (Bhat (1988) *Brain Res.* 452: 373–377). Reduced levels of N-CAM also have been associated with normal pressure hydrocephalus (Werdelin (1989) *Acta Neurol. Scand.* 79: 177–181), and with type II schizophrenia (Lyons et al., (1988) *Biol. Psychiatry* 23: 769–775.) In addition, antibodies to N-CAM have been shown to disrupt functional recovery in injured nerves (Remsen (1990) *Exp. Neurobiol.* 110: 268–273).

It is an object of this invention to provide methods for enhancing survival of neurons at risk of dying in a mammal. Another object is to provide methods for maintaining neural pathways in vivo at risk of injury, or following damage to nerve tissue due to mechanical or chemical trauma, a neuropathy, or a neoplastic lesion. Another object is to provide compositions and devices for repairing gaps in a neural pathway of the peripheral nervous system. Yet another object is to provide a means for redifferentiating transformed cells defining neural pathways, particularly transformed cells of neural origin. Another object is to provide a means for stimulating CAM expression, particularly N-CAM expression in a cell. Yet another object is to provide methods for monitoring the status of nerve tissue by monitoring fluctuations in protein levels present in nerve tissue, serum and/or cerebrospinal fluid. Still other objects are to provide methods and compositions for promoting dendrite outgrowth of neural cells from both the central and peripheral nervous system; to provide methods and compositions for preserving a dendritic arbor which may be at risk of deterioration or may be damaged by mechanical or chemical trauma, neuropathy, or a neoplastic lesion; and to provide methods and compositions for amelioration and clinical management of neurodegenerative disorders including memory, motor, associative, and metabolic disorders. Yet another object of this invention is to provide a composition for repairing a dendritic arbor and promoting regeneration of dendritic architecture at a site of injury, damage, or impairment.

These and other objects and features of the invention will be apparent from the description, drawings, and claims which follow.

SUMMARY OF THE INVENTION

Embodiments of the present invention provide methods and compositions for maintaining neural pathways in a mammal in vivo, including methods for enhancing the survival of neural cells.

As used herein, a "neural pathway" describes a nerve circuit for the passage of electric signals from a source to a target cell site. The pathway includes the neurons through which the electric impulse is transported, including groups of interconnecting neurons, the nerve fibers formed by bundled neuronal axons, and the glial cells surrounding and associated with the neurons. At the level of cell—cell interaction, the pathway includes neural processes such as axons an dendrites, which provide and participate in specific sites of electrical contact and/or signal transmission between the cells forming the pathway. Sites of contact and signal transmission between nerve cells or between a nerve cell and another type of cell are referred to herein as synapses.

In one aspect, the present invention features compositions and therapeutic treatment methods that comprise the step of administering to a mammal a therapeutically effective amount of a morphogenic protein ("morphogen"), as defined herein and set forth in detail below, upon injury to a neural pathway, or in anticipation of such injury, for a time and at a concentration sufficient to maintain or preserve the neural pathway, including repairing damaged pathways, or inhibiting additional damage thereto. Thus, in certain preferred embodiments, the present invention provides methods for promoting dendrite outgrowth, including methods for preserving dendritic arbors and promoting regeneration of dendritic architecture.

In another aspect, the invention features compositions and therapeutic treatment methods for maintaining neural pathways in a mammal in vivo which include administering to the mammal, upon injury to a neural pathway or in anticipation of such injury, a compound that stimulates in vivo a therapeutically effective concentration of an endogenous morphogen within the body of the mammal sufficient to maintain or preserve the neural pathway, including repairing damaged pathways or inhibiting additional damage thereto. These compounds are referred to herein as morphogen-stimulating agents, and are understood to include substances which, when administered to a mammal, act on tissue(s) or organ(s) that normally are responsible for, or competent for, producing or secreting a morphogen and which cause the endogenous level of the morphogen to be altered. The agent may act, for example, by stimulating expression, secretion, or both, of an endogenous morphogen.

In particular, the invention provides methods for enhancing the survival of neurons at risk of dying, including protecting neurons from the tissue destructive effects associated with the body's immune/inflammatory response to a nerve injury. The invention also provides methods for stimulating neurons to maintain their differentiated phenotype or to preserve expression of this phenotype, including inducing the redifferentiation of transformed cells of neuronal origin to a morphology characteristic of untransformed neurons. In one embodiment, the invention provides means for stimulating production of cell adhesion molecules in cells, particularly nerve cell adhesion molecules (N-CAM) in neurons. The invention also provides methods, compositions and devices for stimulating cellular repair of damaged neurons and neural pathways, including regenerating damaged axons of the peripheral and central nervous systems. In addition, the invention also provides means for evaluating the status of nerve tissue, and for detecting and monitoring neuropathies in a mammal by monitoring fluctuations in the morphogen levels or endogenous morphogen antibody levels present in a mammal's serum or cerebrospinal fluid.

As used herein, "dendrites" or "dendritic outgrowth" refers to nerve cell processes distinguishable from axons by virtue of their morphological and immunological characteristics (Lein and Higgins (1989), 136 *Dev. Biol.* 330–345, the teachings of which are herein incorporated by reference). For example, dendrites are morphologically distinguishable in that dendrites are broad-based (up to 5 $\mu$m in diameter), exhibit a distinct taper, and branch in a "Y"-shaped pattern with daughter processes being distinctly smaller than the parent process. Additionally, dendrites are thicker than axons, and unlike axons, they terminate locally usually extending less than 300 $\mu$m from the soma. With respect to immunological characteristics, dendrites and axons are also readily distinguishable using certain antibody-based probes. For example, antibodies to MAP2, non-phosphorylated forms of M and H neurofilaments, and the transferrin receptor are considered by the skilled artisan to be dendrite specific surface markers. Axon specific markers include antibodies to synaptophysin, Tau1, and phosphorylated forms of M and H neurofilament subunits. The appearance of these surface antigens can be differentially detected using, e.g., indirect immunofluoresence, thereby permitting identification of nerve cell processes as dendrites or axons.

In one aspect, the invention features compositions and methods that comprise the step of contacting neural cells with a morphogenic protein ("morphogen") as defined herein, for a time and at a concentration effective for promoting dendrite outgrowth, including preserving a dendritic arbor or regenerating dendritic architecture in both the central and peripheral nervous systems.

In another aspect of the invention, the morphogens described herein are useful in repairing damaged neural pathways of the peripheral nervous system. In particular, the morphogens are useful for repairing damaged pathways, including transected or otherwise damaged nerve fibers (nerves) requiring regeneration of neuronal processes, particularly axons, over extended distances to bridge a gap in the nerve itself, or between the nerve and a post-synaptic cell. Specifically, the morphogens described herein are capable of stimulating complete axonal nerve regeneration, including vascularization and reformation of the protective myelin sheath. The morphogen preferably is provided to the site of injury dispersed in a biocompatible, bioresorbable carrier material capable of maintaining the morphogen at the site and, where necessary, means for directing axonal growth from the proximal to the distal ends of a severed neuron or nerve. For example, means for directing axonal growth may be required where nerve regeneration is to be induced over an extended distance, such as greater than 10 mm. Many carriers capable of providing these functions are envisioned. For example, useful carriers include substantially insoluble materials or viscous solutions prepared as disclosed herein comprising laminin, hyaluronic acid or collagen, or other suitable synthetic, biocompatible polymeric materials such as polylactic, polyglycolic or polybutyric acids and/or copolymers thereof. The currently preferred carrier comprises an extracellular matrix composition, such as one described herein derived, for example, from mouse sarcoma cells. Also envisioned as especially useful are brain tissue-derived extracellular matrices.

In a particularly preferred embodiment, the morphogen is provided to the site as part of a device wherein the morphogen is disposed in a nerve guidance channel which spans the distance of the damaged pathway. The channel acts both as a protective covering and a physical means for guiding growth of a neuronal process such as an axon. Useful channels comprise a bibcompatible membrane or casing, which may be tubular in structure, having a dimension sufficient to span the gap or break in the nerve to be repaired, and having openings adapted to receive severed nerve ends. The casing or membrane may be made of any biocompatible, nonirritating material, such as silicone or a biocompatible polymer such as polyethylene or polyethylene vinyl acetate. The casing also may be composed of biocompatible, bioresorbable polymers, including, for example, collagen, hyaluronic acid, polylactic, polybutyric and polyglycolic acids. In a currently preferred embodiment, the outer surface of the channel is substantially impermeable.

The morphogen may be disposed in the channel in association with a biocompatible carrier material, or it may be adsorbed to or otherwise associated with the inner surface of the casing, such as is described in U.S. Pat. No. 5,011,486, provided that the morphogen is accessible to the severed nerve ends. Additionally, although the nerve guidance channels described herein generally are tubular in shape, it should be evident to those skilled in the art that various alternative shapes may be employed. The lumen of the guidance channels may, for example, be oval or even square in cross section. Moreover the guidance channels may be constructed of two or more parts which may be clamped together to secure the nerve stumps. Nerve endings may be secured to the nerve guidance channels by means of sutures, biocompatible adhesives such as fibrin glue, or other means known in the medical art.

The morphogens described herein also are envisioned to be useful in autologous peripheral nerve segment implants to bypass damaged neural pathways in the central nervous system, such as in the repair of damaged or detached retinas, or other damage to the optic nerve. Here the morphogen is provided to the site of attachment to stimulate axonal growth at the graft site, particularly where the damaged axonal segment to be bypassed occurs far from the neuronal cell body.

The morphogens described herein also are useful for enhancing survival of neuronal cells at risk of dying, thereby preventing, limiting or otherwise inhibiting damage to neural pathways. Non-mitotic neurons are at risk of dying as a result of a neuropathy or other cellular dysfunction of a neuron or glial cell inducing cell death, or following a chemical or mechanical lesion to the cell or its surrounding tissue. The chemical lesions may result from known toxic agents, including lead, ethanol, ammonia, formaldehyde and many other organic solvents, as well as the toxins in cigarette smoke and opiates. Excitatory amino acids, such as glutamate also may play a role in the pathogenesis of neuronal cell death (see Freese et al. (1990) *Brain Res.* 521: 254–264). Neuronal cell death also is thought to be a significant contributing factor in a number of progressive neuropathies currently classified as neurodegenerative diseases, including Alzheimer's disease, Huntington's chorea, and Parkinson's disease, amyotrophic lateral sclerosis and multiple sclerosis. The etiology of these diseases may be metabolic, as results in hepatic encephalopathy, infectious, toxic, autoimmune, nutritional or ischemic. In addition, ethanol and a number of other toxins also have been identified as significant contributing factors in neurodegenerative diseases. The morphogens described herein may be provided to cells at risk of dying to enhance their survival and thereby protect the integrity of the neural pathway. The morphogens may be provided directly to the site, or they may be provided systemically. Alternatively, as described above, an agent capable of stimulating endogenous morphogen expression and/or secretion, preferably in cells associated with the nerve tissue of interest, may be administered to the mammal.

In another aspect of the invention, the method disclosed is useful for redifferentiating transformed cells, particularly transformed cells of neuronal or glial origin, such that the morphogen-treated cells are induced to display a morphology characteristic of untransformed cells. Where the transformed cells are cells of neuronal origin, morphogen treatment preferably induces cell rounding and cell aggregation (clumping), cell—cell adhesion, neurite outgrowth formation and elongation, and N-CAM production. The methods described herein are anticipated to substantially inhibit or reduce neural cell tumor formation and/or proliferation in nerve tissue. It is anticipated that the methods of this invention will be useful in substantially reducing the effects of various carcinomas of nerve tissue origin such as retinoblastomas, neuroblastomas, and gliomas or glioblastomas. In addition, the method also is anticipated to aid in inhibiting neoplastic lesions caused by metastatic tissue. Metastatic tumors are one of the most common neoplasms of the CNS, as they can reach the intracranial compartment through the bloodstream. Metastatic tumors may damage neural pathways for example, by distorting normal nerve tissue structure, compressing nerves, blocking flow of cerebrospinal fluid or the blood supply nourishing brain tissue, and/or by stimulating the body's immune response.

In another aspect of the invention, the morphogens described herein are useful for providing neuroprotective effects to alleviate neural pathway damage associated with the body's immune/inflammatory response to an initial injury to nerve tissue. Such a response may follow trauma to nerve tissue, caused, for example, by an autoimmune dysfunction, neoplastic lesion, infection, chemical or mechanical trauma, disease, by interruption of blood flow to the neurons or glial cells, for example following ischemia or hypoxia, or by other trauma to the nerve or surrounding material. For example, the primary damage resulting from hypoxia or ischemia-reperfusion following occlusion of a neural blood supply, as in an embolic stroke, is believed to be immunologically associated. In addition, at least part of the damage associated with a number of primary brain tumors also appears to be immunologically related. Application of the morphogen directly to the cells to be treated, or providing the morphogen to the mammal systemically, for example, intravenously or indirectly by oral administration, may be used to alleviate and/or inhibit the immunologically related response to a neural injury. Alternatively, administration of an agent capable of stimulating morphogen expression and/or secretion in vivo, preferably at the site of injury, also may be used. Where the injury is to be induced, as during surgery or other aggressive clinical treatment, the morphogen or agent may be provided prior to induction of the injury to provide a neuroprotective effect to the nerve tissue at risk.

In still another aspect, the invention described herein provides methods for supporting the growth and maintenance of differentiated neurons, including inducing neurons to continue expressing their active differentiated phenotype. It is anticipated that this activity will be particularly useful in the treatment of nerve tissue disorders where loss of function is caused by reduced or lost cellular metabolic function and cells become senesent or quiescent, such as is thought to occur in aging cells and to be manifested in Alzheimer's disease. Application of the morphogen directly to cells to be treated, or providing it systemically by parenteral or oral administration stimulates these cells to continue expressing their active differentiated phenotype, significantly inhibiting and/or reversing the effects of the cellular metabolic dysfunction, thereby maintaining the neural pathway at risk. Alternatively, administration of an agent capable of stimulating endogenous morphogen expression and/or secretion in vivo may be used.

In still another aspect, the invention provides methods for stimulating CAM expression levels in a cell, particularly N-CAM expression in neurons. CAMs are molecules defined as carrying out cell—cell interactions necessary for tissue formation. CAMs are believed to play a fundamental regulatory role in tissue development, including tissue boundary formation, embryonic induction and migration, and tissue stabilization and regeneration. Thus, patterns of expression of individual CAMs may guide, in a positive (attractant) or negative (deterrent) sense, the formation of specific cell—cell contacts, including synapses, within nerve tissue and among nerve and innervated tissues. Alternatively, CAM expression may respond to fluctuations in electromagnetic and/or biochemical signals within and between cells and tissues. Gradients of biochemical signals (e.g., chemoattractants) long have been thought to exist in developing tissues and to provide cells of these tissues with positional information necessary for the proper course of morphogenesis of defined tissues and organs in the embryo. Without being limited to any particular theory, it is believed that morphogens released by particular cells of an organ or tissue can diffuse within developing tissues and organs to provide a biochemical gradient from which cells can extract positional information needed for normal pattern formation or morphogenesis. Thus, morphogens can be viewed as chemotrophic or chemotactic factors that guide and promote differentiation of particular cell or tissue types and/or dissuade differentiation of inappropriate cell or tissue types. This concept is presented in Basler et al. (1993), 73 *Cell* 687–702, the teachings of which are incorporated herein by reference.

Altered CAM levels have been implicated in a number of tissue disorders, including congenital defects, neoplasias, and degenerative diseases. In particular, N-CAM expression is associated with normal neuronal cell development and differentiation, including retinal formation, synaptogenesis, and nerve-muscle tissue adhesion. Inhibition of one or more of the N-CAM isoforms is known to prevent proper tissue development. Altered N-CAM expression levels also are associated with neoplasias, including neuroblastomas (see infra), as well as with a number of neuropathies, including normal pressure hydrocephalous and type II schizophrenia. Application of the morphogen directly to the cells to be treated, or providing the morphogen to the mammal systemically, for example, parenterally, or indirectly by oral administration, may be used to induce cellular expression of one or more CAMs, particularly N-CAMs. Alternatively, administration of an agent capable of stimulating morphogen expression and/or secretion in vivo, preferably at the site of injury, also may be used to induce CAM production.

CAMs also have been postulated as part of a morphoregulatory pathway whose activity is induced by a to date unidentified molecule (See, for example, Edelman, G. M. (1986) *Ann. Rev. Cell Biol.* 2: 81–116). Without being limited to any given theory, the morphogens described herein may act as the inducer of this pathway.

Still further, modulations of endogenous morphogen levels may be monitored as part of a method of detecting nerve tissue dysfunction. Specifically, modulations in endogenous morphogen levels are anticipated to reflect changes in nerve tissue status. Morphogen expression may be monitored directly in biopsied cell samples, in cerebrospinal fluid, or serum. Alternatively, morphogen levels may be assessed by detecting changes in the levels of endogenous antibodies to the morphogen. For example, one may obtain serum samples from a mammal, and then detect the concentration of morphogen or antibody present in the fluid by standard protein detection means known to those skilled in the art. As an example, binding protein capable of interacting specifically with the morphogen of interest such as an anti-morphogen antibody may be used to detect a morphogen in a standard immunoassay. The morphogen levels detected then may be compared to a previously determined standard or reference level, with changes in the detected levels being indicative of the status of the tissue.

In certain embodiments of the invention, the morphogen or morphogen-stimulating agent is administered systemically to the individual, e.g., orally or parenterally. In other embodiments of the invention, the morphogen can be provided directly to the nerve tissue, e.g., by injection to the cerebral spinal fluid or to a nerve tissue locus.

In any treatment method of the invention, "administration of mophogen" refers to the administration of the morphogen, either alone or in combination with other molecules. For example, the mature form of the morphogen may be provided in association with its precursor "pro" domain, which is known to enhance the solubility of the protein. Other useful molecules known to enhance protein solubility include casein and other milk components, as well as various serum proteins. Additional useful molecules which may be associated with the morphogen or morphogen-stimulating agent include tissue targeting molecules capable of directing the morphogen or morphogen-stimulating agent to nerve tissue. Tissue targeting molecules envisioned to be useful in the treatment protocols of this invention include antibodies, antibody fragments or other binding proteins which interact specifically with surface molecules on nerve tissue cells.

Still another useful tissue targeting molecule is part or all of the morphogen precursor "pro" domain, particularly that of OP-1 or GDP-1. These proteins are found naturally associated with nerve tissue but also may be synthesized in other tissues and targeted to nerve tissue after secretion from the synthesizing tissue. For example, while the protein has been shown to be active in bone tissue, the primary source of OP-1 synthesis appears to be the tissues of the urogenic system (e.g., renal and bladder tissue), with secondary expression levels occurring in the brain, heart and lungs (see below.) Moreover, the protein has been identified in serum, saliva and various milk forms. In addition, the secreted form of the protein comprises the mature dimer in association with the pro domain of the intact morphogen sequence. Accordingly, the associated morphogen pro domains may act to target specific morphogens to different tissues in vivo.

Associated tissue targeting or solubility-enhancing molecules also may be covalently linked to the morphogen using standard chemical means, including acid-labile linkages, which likely will be preferentially cleaved in acidic environments.

Finally, the morphogens or morphogen-stimulating agents provided herein also may be administered in combination with other molecules known to be beneficial in maintaining neural pathways, including, for example, anti-inflammatory agents and nerve trophic (growth) factors.

In this regard, the present invention also features compositions and methods that comprise the step of contacting neural cells with a morphogenic protein and a nerve trophic factor as defined below, for a time and at a concentration effective for promoting dendrite outgrowth, including preserving a dendritic arbor or regenerating dendritic architecture in both the central and peripheral nervous systems.

"Nerve trophic factors" as defined herein refer to proteins able to stimulate survival and growth of nerve cells (Hefti and Lapchak (1993), 24 Adv. in Pharmacol. 239–273). Most of the characterized actions of nerve trophic actors relate to developmental events and suggest that the temporal and local regulation of expression of these proteins plays a role during maturation of the nervous system. Nerve trophic factors are also important in the function of the adult nervous system for the maintenance of structural integrity and regulation of plasticity. Such processes are altered by diseases and neurodegenerative events following acute injury to the nervous system. This has prompted speculation that nerve trophic factors are involved in the structural alterations which occur in response to injury and disease.

Nerve trophic factors are found among several protein families, including neurotrophins, fibroblast growth factors, the epidermal growth factor protein family, and lymphokines to name a few. Nerve growth factor (NGF) is the best characterized member of the nerve trophic factor protein families. NGF belongs to the protein family called neurotrophins, the other known members of which are brain-derived neurotrophic factor (BDNF), neurotrophin-3. (NT-3), neurotrophin-4 (NT-4), and neurotrophin-5 (NT-5). Individual neurotrophins are highly conserved among mammalian species and share at least about 50% amino acid sequence homology with each other known member of this group. Preferred for use herein are nerve trophic factors having amino acid sequences that comprise a sequence sharing at least about 50%, preferably at least about 60%, homology with each of the sequences of human NGF, human BDNF, human NT-3, human NT-4, and human NT-5. Alternatively, mammalian nerve trophic factors can be used herein that have amino acid sequences comprising six cysteine residues in relative positions that are strictly conserved and in common with the sequences of the currently known nerve trophic factors of rats, humans, chickens, and frogs (*Xenopus*). See, e.g., Bradshaw et al. (1993), *Trends in Biotechology Sciences* (TIBS); Ebendal (1992), 32 *J. of Neurosci. Res.* 461; Meakin and Shooter (1992), 15 *Trends in Neurosciences* (TINS) 323; Swindells (1992), 258 *Science* 1160; Daopin et al. (1992), 258 *Science* 1661.

In a related aspect, the present invention features compositions and methods for promoting dendritic outgrowth which include administering to a mammal a first agent that stimulates production of an endogenous morphogen within the mammal at a concentration effective for promoting dendritic outgrowth. As described above, these agents are referred to herein as morphogen-stimulating agents, and are understood to include substances which, when administered to a mammal, act on tissues or organs that normally are responsible for, or capable of, producing a morphogen and/or secreting a morphogen, and which cause the endogenous level of the morphogen to be altered. The agent can act, for example, by stimulating expression and/or secretion of an endogenous morphogen. Another feature of the present invention includes administering this first agent and a nerve trophic factor at concentrations and for times effective for promoting dendritic outgrowth. The first agent and the nerve trophic factor can be co-administered in a composition.

In yet another related aspect, the invention also features compositions and methods for promoting dendritic outgrowth which include administering to a mammal the above-described morphogen-stimulating factor and a second agent that stimulates production of an endogenous nerve trophic factor at concentrations effective for promoting dendritic outgrowth. It is understood that production of the endogenous nerve trophic factor includes cells or tissue normally responsible for, or capable of, producing the endogenous level of factor. Both agents can be co-administered in a composition. Preferably, both agents can cross the blood-brain barrier, either passively or actively.

In a particularly preferred embodiment, a morphogen is provided to the site of nerve impairment or damage as a composition comprising a biocompatible, in vivo bioresorbable carrier suitable for maintaining a protein at a site in vivo, wherein the morphogen is dispersed in the carrier to a concentration effective for stimulating dendritic outgrowth at the site of impairment or damage. The carrier can be composed of a polymeric material such as laminin or collagen, or comprise brain-tissue-derived extracellular matrix. In another preferred embodiment, a morphogen and a nerve trophic factor are disposed at the site of impairment or damage by means of a biocompatible, in vivo resorbable carrier suitable for maintaining both at the site in vivo. Both can be admixed with the carrier and co-provided to the site of impairment or damage.

Another preferred embodiment of the present invention comprises a composition for ameliorating a neuropathy, comprising a morphogen in combination with a nerve trophic factor, the concentrations of which in combination are competent to promote dendrite outgrowth. "Neuropathy" in this context refers to a memory, motor, associative, or metabolic disorder, and includes Alzheimer's disease, Parkinson's disease, Lewy body dementia, progressive supranuclear palsy, dementia pugilistica, olivopontocerebellar atrophy, Wernicke-Korsakoff's syndrome and diabetic neuropathy. Amelioration refers to clinical management of the disorder, including attenuation, alleviation, remission or cure of the disorder. This composition also comprises a biocompatible acellular support matrix suitable for maintaining said morphogen and said nerve trophic factor at a site-in vivo. The support matrix can be composed of a malleable gel or a solid polymeric material that permits dendrite growth around and within the matrix. Exemplary matrices include laminin or collagen.

Where the morphogen is intended for use as a therapeutic for disorders of the CNS, an additional problem must be addressed: overcoming the so-called "blood-brain barrier", the brain capillary wall structure that effectively screens out all but selected categories of molecules present in the blood, preventing their passage into the brain. The blood-brain barrier can be bypassed effectively by direct infusion of the morphogen or morphogen-stimulating agent into the brain. Alternatively, the morphogen or morphogen-stimulating agent can be modified to enhance its transport across the blood-brain barrier. For example, truncated forms of the morphogen or a morphogen-stimulating agent may be most successful. Alternatively, the morphogen or morphogen-stimulating agent may be modified to render it more lipophilic, or it may be conjugated to another molecule which is naturally transported across the barrier, using standard means known to those skilled in the art, as, for example, described in Pardridge, *Endocrine Reviews* 7: 314–330 (1986) and U.S. Pat. No. 4,801,575.

Accordingly, as used herein, a functional "analog" of a morphogen refers to a protein having morphogenic biological activity but possessing additional structural differences compared to a morphogen as defined herein, e.g., having additional chemical moieties not normally apart of a morphogen. Such moieties (introduced, for example, by acylation, alkylation, cationization, or glycosylation reactions, or other means for conjugating the moiety to the morphogen) can improve the molecule's solubility, absorption, biological half-life, or transport, e.g., across the blood-brain barrier.

Among the morphogens useful in this invention are proteins originally identified as osteogenic proteins, such as the OP-1, OP-2 and CBMP2 proteins, as well as amino acid sequence-related proteins such as DPP (from *Drosophila*), Vgl (from *Xenopus*), Vgr-1 (from mouse, see U.S. Pat. No. 5,011,691 to Oppermann et al.), GDF-1 (from mouse, see Lee (1991) *PNAS* 88: 4250–4254), all of which are presented in Table II and Seq. ID Nos.5–14), and the recently identified 60A protein (from *Drosophila*, Seq. ID No. 24, see Wharton et al. (1991) *PNAS* 88: 9214–9218.) The morphogens collectively comprise a family or genus, which includes members of a structurally distinct sub-family of the TGF-β super-family of proteins. That is, the morphogens share substantial amino acid sequence homology in their C-terminal regions, including a conserved arrangement or motif of cysteine residues shared by members of the TGFβ super-family. The proteins are translated as a precursor, having an N-terminal signal peptide sequence, typically less than about 30 residues, followed by a "pro" domain that is cleaved to yield the mature C-terminal domain. The signal peptide is cleaved rapidly upon translation, at a cleavage site that can be predicted in a given sequence using the method of Von Heijne ((1986) *Nucleic Acids Research* 14: 4683–4691.) Table I, below, describes the various morphogens identified to date, including their nomenclature as used herein, their Seq. ID references, and publication sources for the amino acid sequences for the full length proteins not included in the Seq. Listing. The disclosure of these publications is incorporated herein by reference.

Table I

"OP-1" Refers generally to a morphogenically active protein expressed from a DNA sequence encoding at least a portion of OP-1 protein bearing the above-mentioned conserved cysteine residues. Thus, for example, a human OP-1 protein has an amino acid sequence comprising at least the conserved seven cysteine skeleton defined by residues 38–139 of Seq. ID No. 5. In a broader sense, however, "OP1" refers to naturally occuring or biosynthetic conservative variants of the human OP1 disclosed in Seq. ID No. 5. Naturally occurring variants include OP1 variants isolated from individuals of a single phylogenetic species (e.g., humans). Such variants are referred to herein as "allelic variants." Other naturally occurring variants include counterparts of human OP1 isolated from phylogenetically distinct species (e.g., mouse, *Drosophila*). These variants are referred to herein as "species variants" and can also be referred to as phylogenetic counterparts or homologs. The mature protein amino acid sequence of human OP-1 ("hOP-1") is set forth in Seq. ID No. 5 and that of mouse OP-1 (mOP-1) is set forth-in Seq. ID No. 6. The conserved seven cysteine skeleton in each protein is defined by residues 38 to 139 of Seq. ID Nos. 5 and 6. The cDNA sequences and the amino acids encoding the full length proteins are provided in Seq. Id Nos. 16 and 17 (hOP1) and Seq. ID Nos. 18 and 19 (mOP1.) The mature proteins are defined by residues 293–431 (hOP1) and 292–430 (mOP1). The "pro" regions of the proteins, cleaved to yield the mature, morphogenically active proteins are defined essentially by residues 30–292 (hOP1) and residues 30–291 (mOP1).

"OP-2, refers generally to a morphogenically active protein expressed from a DNA sequence encoding at least a portion of OP-2 protein bearing the above-mentioned conservative arrangement of cysteine residues. Thus, for example, a human OP2 protein has an amino acid sequence comprising at least the conserved seven cysteine skeleton defined by residues 38–139 of Seq. ID No. 7. As explained above, "OP2" refers in a broader sense to naturally occurring or biosynthetic conservative variants of the human OP2 disclosed in Seq. ID No. 7, including allelic and species variants thereof, e.g., human OP-2 ("hOP-2", Seq. ID No. 7, mature protein amino acid sequence) or mouse OP-2 ("mOP-2", Seq. ID No. 8, mature protein amino acid sequence). The conserved seven cysteine skeleton is defined by residues 38 to 139 of Seq. ID Nos. 7 and 8. The cDNA sequences and the amino acids encoding the full length proteins are provided in Seq. ID Nos. 20 and 21 (hOP2) and Seq. ID Nos. 22 and 23 (mOP2.) The mature proteins are defined essentially by residues 264–402 (hOP2) and 261–399 (mOP2). The "pro" regions of the proteins, cleaved to yield the mature, morphogenically active proteins likely are defined essentially by residues 18–263 (hOP2) and residues 18–260 (mOP2). (Another cleavage site also occurs 21 residues upstream for both OP-2 proteins.)

"CBMP2" refers generally to a morphogenically active protein expressed from a DNA sequence encoding at least a portion of the CBMP2 proteins bearing the above-mentioned conserved arrangement of cysteine residues, including allelic and species variants thereof, e.g., human CBMP2A ("CBMP2A(fx)", Seq ID No. 9) or human CBMP2B DNA ("CBMP2B(fx)", Seq. ID No. 10). The amino acid sequence for the full length proteins, referred to in the literature as BMP2A and BMP2B, or BMP2 and BMP4, appear in Wozney, et al., (1988) *Science* 242: 1528–1534 The pro domain for BMP2 (BMP2A) likely includes residues 25–248 or 25–282; the mature protein, residues 249–396 or 283–396. The pro domain for BMP4 (BMP2B) likely includes residues 25–256 or 25–292; the mature protein, residues 257–408 or 293–408.

"DPP(fx)" refers to protein sequences encoded by the *Drosophila* DPP gene and defining the conserved seven cysteine skeleton (Seq. ID No. 11). The amino acid sequence for the full length protein appears in Padgett, et al (1987) *Nature* 325: 81–84. The pro domain likely extends from the signal peptide cleavage site to residue 456; the mature protein likely is defined by residues 457–588.

"Vgl(fx)" refers to protein sequences encoded by the *Xenopus* Vgl gene and defining the conserved seven cysteine skeleton (Seq. ID No. 12). The amino acid sequence for the full length protein appears in Weeks (1987) *Cell* 51: 861–867. The prodomain likely extends from the signal peptide cleavage site to residue 246; the mature protein likely is defined by residues 247–360.

"Vgr-1(fx)" refers to protein sequences encoded by the murine Vgr-1 gene and defining the conserved seven cysteine skeleton (Seq. ID No. 13). The amino acid sequence for the full length protein appears in Lyons, et al, (1989) *PNAS* 86: 4554–4558. The prodomain likely extends from the signal peptide cleavage site to residue 299; the mature protein likely is defined by residues 300–438.

"GDF-1(fx)" refers to protein sequences encoded by the human GDF-1 gene and defining the conserved seven cysteine skeleton (Seq. ID No. 14). The cDNA and encoded amino sequence for the full length protein is provided in Seq. ID. No. 32. The prodomain likely extends from the signal peptide clavage site to residue 214; the mature protein likely is defined by residues 215–372.

"60A" refers generally to morphogenically active proteins expressed from a DNA sequence (from the *Drosophila* 60A gene) encoding at least a portion of the 60A protein that bears the conserved arrangement of cysteine residues (see Seq. ID No. 24 wherein the cDNA and encoded amino acid sequence for the full length protein is provided). *Drosphila* 60A protein is thought to be a species variant of human OP1. "60A(fx)" refers to the protein sequences defining the conserved seven cysteine skeleton (residues 354 to 455 of Seq. ID No. 24.) The prodomain likely extends from the signal peptide cleavage site to residue 324; the mature protein likely is defined by residues 325–455.

BMP3(fx)" refers to protein sequences encoded by the human BMP3 gene and defining the conserved seven cysteine skeleton (Seq. ID No. 26). The amino acid sequence for the full length protein appears in Wozney et al. (1988) *Science* 242: 1528–1534. The pro domain likely extends from the signal peptide cleavage site to residue 290; the mature protein likely is defined by residues 291–472.

"BMP5(fx)" refers to protein sequences encoded by the human BMP5 gene and defining the conserved seven cysteine skeleton (Seq. ID No. 27). The amino acid sequence for the full length protein appears in Celeste, et al. (1991) *PNAS* 87: 9843–9847. The pro domain likely extends from the signal peptide cleavage site to residue 316; the mature protein likely is defined by residues 317–454.

"BMP6(fx)" refers to protein sequences encoded by the human BMP6 gene and defining the conserved seven cysteine skeleton (Seq. ID No. 28). The amino acid sequence for the full length protein appears in Celeste, et al. (1990) *PNAS* 87: 9843–5847. The pro domain likely includes extends from the signal peptide cleavage site to residue 374; the mature sequence likely includes residues 375–513.

The OP-2 proteins have an additional cysteine residue in this region (e.g., see residue 41 of Seq. ID Nos. 7 and 8), in addition to the conserved cysteine skeleton in common with the other proteins in this family. The GDF-1 protein has a four amino acid insert within the conserved skeleton (residues 44–47 of Seq. ID. No. 14) but this insert likely does not interfere with the relationship of the cysteines in the folded structure. In addition, the CBMP2 proteins are missing one amino acid residue within the cysteine skeleton.

The morphogens are inactive when reduced, but are active as oxidized homodimers and when oxidized in combination with other morphogens of this invention. Thus, as defined herein, a morphogen is a dimeric protein comprising a pair of polypeptide chains, wherein the sequence of each polypeptide chain comprises at least the C-terminal seven cysteine skeleton defined by the positionally conserved seven cysteine residues included within residues 38–139 of Seq. ID No. 5, including functionally equivalent arrangements of these cysteines (e.g., amino acid insertions or deletions which alter the linear arrangement of the cysteines in the sequence but not their relationship in the folded structure), such that, 15. when the polypeptide chains are folded, the dimeric protein species comprising the pair of polypeptide chains has the appropriate three-dimensional structure, including the appropriate intra- or inter-chain disulfide bonds such that the protein has morphogenic activity as defined herein. Specifically, the morphogens generally are competent to induce all of the following biological functions in a morphogenically permissive environment: stimulating proliferation of progenitor cells; stimulating the differentiation of progenitor cells; stimulating the proliferation of differentiated cells; and supporting the growth and maintenance of differentiated cells. In addition, it is also anticipated that these morphogens are capable of inducing redifferentiation of committed cells under appropriate environmental conditions.

The positional locations of cysteine residues conserved among the morphogens of this invention are set forth in Generic Sequence 1 (Seq. ID No. 1) and Generic Sequence 2 (Seq. ID No. 2); where each Xaa indicates one of the 20 naturally-occurring L-isomer, α-amino acids or a derivative thereof. Generic Sequence 1 comprises the conserved six cysteine skeleton and Generic Sequence 2 comprises the conserved six cysteine skeleton plus the additional cysteine identified in OP-2 (see residue 36, Seq. ID No. 2). The conserved seven cysteine skeleton of the morphogens is produced when the following additional sequence is present in the morphogen polypeptide chain N-terminal to and adjoining the region bearing the positionally conserved cysteines of Generic Sequences 1 and 2:

```
Cys Xaa Xaa Xaa Xaa    (Seq. ID No. 15)
 1               5
```

Preferred amino acid sequences within the foregoing generic sequences include: Generic Sequence 3 (Seq. ID No. 3), Generic Sequence 4 (Seq. ID No. 4), Generic Sequence 5 (Seq. ID No. 30) and Generic Sequence 6 (Seq. ID No. 31), listed below. These Generic Sequences accommodate homologies shared among various preferred members of the morphogen family or genus identified in Table II, as well as the amino acid sequence variation among them. Specifically, Generic Sequences 3 and 4 are composite amino acid sequences of the following proteins presented in Table II and identified in Seq. ID Nos. 5–14: human OP-1 (hOP-1, Seq. ID Nos. 5 and 16–17), mouse OP-1 (mOP-1, Seq. ID Nos. 6 and 18–19), human and mouse OP-2 (Seq. ID Nos. 7, 8, and 20–22), CBMP2A (Seq. ID No. 9), CBMP2B (Seq. ID No 10), DPP (from *Drosophila*, Seq. ID No. 11), Vgl, (from *Xenopus*, Seq. ID No. 12), Vgr-1 (from mouse, Seq. ID No. 13), and GDF-1 (from mouse, Seq. ID No. 14.) The generic sequences include both the amino acid identity shared by the sequences in Table II, as well as alternative residues for the variable positions within the sequence. Note that these generic sequences allow for an additional cysteine at position 41 or 46 in Generic Sequences 3 or 4, respectively, providing an appropriate cysteine skeleton where inter- or intramolecular disulfide bonds can form, and contain certain critical amino acids which influence the tertiary structure of the proteins.

---

Generic Sequence 3

```
Leu Tyr Val Xaa Phe
 1           5

Xaa Xaa Xaa Gly Trp Xaa Xaa Trp Xaa
                10

Xaa Ala Pro Xaa Gly Xaa Xaa Ala
 15              20

Xaa Tyr Cys Xaa Gly Xaa Cys Xaa
         25              30

Xaa Pro Xaa Xaa Xaa Xaa Xaa
             35

Xaa Xaa Xaa Asn His Ala Xaa Xaa
         40              45

Xaa Xaa Leu Xaa Xaa Xaa Xaa Xaa
             50

Xaa Xaa Xaa Xaa Xaa Xaa Xaa Cys
     55                  60

Cys Xaa Pro Xaa Xaa Xaa Xaa Xaa
             65

Xaa Xaa Xaa Leu Xaa Xaa Xaa
 70              75

Xaa Xaa Xaa Xaa Val Xaa Leu Xaa
             80

Xaa Xaa Xaa Xaa Met Xaa Val Xaa
 85                  90

Xaa Cys Gly Cys Xaa
         95
```

--- wherein each Xaa is independently selected from a group of one or more specified amino acids defined as follows: "Res." means "residue" and Xaa at res.4=(Ser, Asp or Glu); Xaa at res.6=(Arg, Gln, Ser or Lys); Xaa at res.7=(Asp or Glu); Xaa at res.8=(Leu or Val); Xaa at res.11=(Gln, Leu, Asp, His or Asn); Xaa at res.12=(Asp, Arg or Asn); Xaa at res.14=(Ile or Val); Xaa at res.15=(Ile or Val); Xaa at res.18=(Glu, Gln, Leu, Lys, Pro or Arg); Xaa at res.20=(Tyr or Phe); Xaa at res.21=(Ala, Ser, Asp, Met, His, Leu or Gln); Xaa at res.23=(Tyr, Asn or Phe); Xaa at res.26=(Glu, His, Tyr, Asp or Gln); Xaa at res.28=(Glu, Lys, Asp or Gln); Xaa at res.30=(Ala, Ser, Pro or Gln); Xaa at res.31=(Phe, Leu or Tyr); Xaa at res.33=(Leu or Val); Xaa at res.34=(Asn, Asp, Ala or Thr); Xaa at res.35=(Ser, Asp, Glu, Leu or Ala); Xaa at res.36=(Tyr, Cys, His, Ser or Ile); Xaa at res.37=(Met, Phe, Gly or Leu); Xaa at res.38=(Asn or Ser); Xaa at res.39=(Ala, Ser or Gly); Xaa at res.40=(Thr, Leu or Ser); Xaa at res.44=(Ile or Val); Xaa at res.45=(Val or Leu); Xaa at res.46=(Gln or Arg); Xaa at res.47=(Thr, Ala or Ser); Xaa at res.49=(Val or Met); Xaa at res.50=(His or Asn); Xaa at res.51=(Phe, Leu, Asn, Ser, Ala or Val); Xaa at res.52=(Ile, Met, Asn, Ala or Val); Xaa at res.53=(Asn, Lys, Ala or Glu); Xaa at res.54=(Pro or Ser); Xaa at res.55=(Glu, Asp, Asn, or Gly); Xaa at res.56=(Thr, Ala, Val, Lys, Asp, Tyr, Ser or Ala); Xaa at res.57=(Val, Ala or Ile); Xaa at res.58=(Pro or Asp); Xaa at res.59=(Lys or Leu); Xaa at res.60=(Pro or Ala); Xaa at res.63=(Ala or Val); Xaa at res.65=(Thr or Ala); Xaa at res.66=(Gln, Lys, Arg or Glu); Xaa at res.67=(Leu, Met or Val); Xaa at res.68=(Asn, Ser or Asp); Xaa at res.69=(Ala, Pro or Ser); Xaa at res.70=(Ile, Thr or Val); Xaa at res.71=(Ser or Ala); Xaa at res.72=(Val or Met); Xaa at res.74=(Tyr or Phe); Xaa at res.75=(Phe, Tyr or Leu); Xaa at res.76=(Asp or Asn); Xaa at res.77=(Asp, Glu, Asn or Ser); Xaa at res.78=(Ser, Gln, Asn or Tyr); Xaa at res.79=(Ser, Asn, Asp or Glu); Xaa at res.80=(Asn, Thr or Lys); Xaa at res.82=(Ile or Val); Xaa at res.84=(Lys or Arg); Xaa at res.85=(Lys, Asn, Gln or His); Xaa at res.86=(Tyr or His); Xaa at res.87=(Arg, Gln or. Glu); Xaa at res.88=(Asn, Glu or Asp); Xaa at res.90=(Val, Thr or Ala); Xaa at res.92=(Arg, Lys, Val, Asp or Glu); Xaa at res.93=(Ala, Gly or Glu); and Xaa at res.97=(His or Arg);

---

Generic Sequence 4

```
Cys Xaa Xaa Xaa Xaa Leu Tyr Val Xaa Phe
 1               5                   10

Xaa Xaa Xaa Gly Trp Xaa Xaa Trp Xaa
                15

Xaa Ala Pro Xaa Gly Xaa Xaa Ala
 20              25

Xaa Tyr Cys Xaa Gly Xaa Cys Xaa
         30              35

Xaa Pro Xaa Xaa Xaa Xaa Xaa
             40

Xaa Xaa Xaa Asn His Ala Xaa Xaa
         45              50

Xaa Xaa Leu Xaa Xaa Xaa Xaa Xaa
             55

Xaa Xaa Xaa Xaa Xaa Xaa Xaa Cys
     60                  65

Cys Xaa Pro Xaa Xaa Xaa Xaa Xaa
             70

Xaa Xaa Xaa Leu Xaa Xaa Xaa
 75              80

Xaa Xaa Xaa Xaa Val Xaa Leu Xaa
             85

Xaa Xaa Xaa Xaa Met Xaa Val Xaa
 90                  95

Xaa Cys Gly Cys Xaa
         100
```

--- wherein each Xaa is independently selected from a group of one or more specified amino acids as defined by the following: "Res." means "residue" and Xaa at res.2=(Lys or Arg);

Xaa at res.3=(Lys or Arg); Xaa at res.4=(His or Arg); Xaa at res.5=(Glu, Ser, His, Gly, Arg or Pro); Xaa at res.9=(Ser, Asp or Glu); Xaa at res.11=(Arg, Gln, Ser or Lys); Xaa at res.12=(Asp or Glu); Xaa at res.13=(Leu or Val); Xaa at res.16=(Gln, Leu, Asp, His or Asn); Xaa at res.17=(Asp, Arg, or Asn); Xaa at res.19=(Ile or Val); Xaa at res.20=(Ile or Val); Xaa at res.23=(Glu, Gln, Leu, Lys, Pro or Arg); Xaa at res.25=(Tyr or Phe); Xaa at res.26=(Ala, Ser, Asp, Met, His, Leu, or Gln); Xaa at res.28=(Tyr, Asn or Phe); Xaa at res.31=(Glu, His, Tyr, Asp or Gln); Xaa at res.33=Glu, Lys, Asp or Gln); Xaa at res.35=(Ala, Ser or Pro); Xaa at res.36=(Phe, Leu or Tyr); Xaa at res.38=(Leu or Val); Xaa at res.39=(Asn, Asp, Ala or Thr); Xaa at res.40=(Ser, Asp, Glu, Leu or Ala); Xaa at res.41=(Tyr, Cys, His, Ser or Ile); Xaa at res.42=(Met, Phe, Gly or Leu); Xaa at res.44=(Ala, Ser or Gly); Xaa at res.45=(Thr, Leu or Ser); Xaa at res.49=(Ile or Val); Xaa at res.50=(Val or Leu); Xaa at res.51=(Gln or Arg); Xaa at res.52=(Thr, Ala or Ser); Xaa at res.54=(Val or Met); Xaa at res.55=(His or Asn); Xaa at res.56=(Phe, Leu, Asn, Ser, Ala or Val); Xaa at res.57=(Ile, Met, Asn, Ala or Val); Xaa at res.58=(Asn, Lys, Ala or Glu); Xaa at res.59=(Pro or Ser); Xaa at res.60=(Glu, Asp, or Gly); Xaa at res.61=(Thr, Ala, Val, Lys, Asp, Tyr, Ser or Ala); Xaa at res.62=(Val, Ala or Ile); Xaa at res.63=(Pro or Asp); Xaa at res.64=(Lys or Leu); Xaa at res.65=(Pro or Ala); Xaa at res.68=(Ala or Val); Xaa at res.70=(Thr or Ala); Xaa at res.71=(Gln, Lys, Arg or Glu); Xaa at res.72=(Leu, Met or Val); Xaa at res.73=(Asn, Ser or Asp); Xaa at res.74=(Ala, Pro or Ser); Xaa at res.75=(Ile, Thr or Val); Xaa at res.76=(Ser or Ala); Xaa at res.77=(Val or Met); Xaa at res.79=(Tyr or Phe); Xaa at res.80=(Phe, Tyr or Leu); Xaa at res.81=(Asp or Asn); Xaa at res.82=(Asp, Glu, Asn or Ser); Xaa at res.83=(Ser, Gln, Asn or Tyr); Xaa at res.84=(Ser, Asn, Asp or Glu); Xaa at res.85=(Asn, Thr or Lys); Xaa at res.87=(Ile or Val); Xaa at res.89=(Lys or Arg); Xaa at res.90=(Lys, Asn, Gln or His); Xaa at res.91=(Tyr or His); Xaa at res.92=(Arg, Gln or Glu); Xaa at res.93=(Asn, Glu or Asp); Xaa at res.95=(Val, Thr or Ala); Xaa at res.97=(Arg, Lys, Val, Asp or Glu); Xaa at res.98=(Ala, Gly or Glu); and Xaa at res.102=(His or Arg).

Similarly, Generic Sequence 5 (Seq. ID No. 30) and Generic Sequence 6 (Seq. ID No. 31) accommodate the homologies shared among all the morphogen protein family members identified in Table II. Specifically, Generic Sequences 5 and 6 are composite amino acid sequences of human OP-1 (hOP-1, Seq. ID Nos. 5 and 16–17), mouse OP-1 (mOP-1, Seq. ID. Nos. 6 and 18–19), human and mouse OP-2 (Seq. ID Nos. 7, 8, and 20–22), CBMP2A (Seq. ID No. 9), CBMP2B (Seq. ID No. 10), DPP (from *Drosophila*, Seq. ID. No. 11), Vgl, (from *Xenopus*, Seq. ID No. 12), Vgr-1 (from mouse, Seq. ID No. 13), and GDF-1 (from mouse, Seq. ID No. 14), human BMP3 (Seq. ID No. 26), human BMP5 (Seq. ID No. 27), human BMP6 (Seq. ID No. 28) and 60(A) (from *Drosophila*, Seq. ID Nos. 24–25). The generic sequences include both the amino acid identity shared by these sequences in the C-terminal domain, defined by the six and seven cysteine skeltons (Generic Sequences 5 and 6, respectively), as well as alternative residues for the variable positions within the sequence. As for Generic Sequences 3 and 4, Generic Sequences 5 and 6 allow for an additional cysteine at position 41 (Generic Sequence 5) or position 46 (Generic Sequence 6), providing an appropriate cysteine skeleton where inter- or intramolecular disulfide bonds can form, and containing certain critical amino acids which influence the tertiary structure of the proteins.

```
                Generic Sequence 5

Leu Xaa Xaa Xaa Phe
         1               5

Xaa Xaa Xaa Gly Trp Xaa Xaa Trp Xaa
                         10

Xaa Xaa Pro Xaa Xaa Xaa Xaa Ala
         15                      20

Xaa Tyr Cys Xaa Gly Xaa Cys Xaa
                 25                  30

Xaa Pro Xaa Xaa Xaa Xaa Xaa
                         35

Xaa Xaa Xaa Asn His Ala Xaa Xaa
                 40                  45

Xaa Xaa Xaa Xaa Xaa Xaa Xaa
                         50

Xaa Xaa Xaa Xaa Xaa Xaa Cys
         55                      60

Cys Xaa Pro Xaa Xaa Xaa Xaa
                         65

Xaa Xaa Xaa Leu Xaa Xaa Xaa
         70                      75

Xaa Xaa Xaa Xaa Val Xaa Leu Xaa
                         80

Xaa Xaa Xaa Xaa Met Xaa Val Xaa
         85                      90

Xaa Cys Xaa Cys Xaa
                 95
``` wherein each Xaa is independently selected from a group of one or more specified amino acids defined as follows: "Res." means "residue" and Xaa at res.2=(Tyr or Lys); Xaa at res.3=Val or Ile); Xaa at res.4=(Ser, Asp or Glu); Xaa at res.6=(Arg, Gln, Ser, Lys or Ala); Xaa at res.7=(Asp, Glu or Lys); Xaa at res.8=(Leu, Val or Ile); Xaa at res.11=(Gin, Leu, Asp, His, Asn or Ser); Xaa at res.12=(Asp, Arg, Asn or Glu); Xaa at res.14=(Ile or Val); Xaa at res.15=(Ile or Val); Xaa at res.16 (Ala or Ser); Xaa at res.18=(Glu, Gln, Leu, Lys, Pro or Arg); Xaa at res.19=(Gly or Ser); Xaa at res.20=(Tyr or Phe); Xaa at res.21=(Ala, Ser, Asp, Met, His, Gln, Leu or Gly); Xaa at res.23=(Tyr, Asn or Phe); Xaa at res.26=(Glu, His, Tyr, Asp, Gln or Ser); Xaa at res.28=(Glu, Lys, Asp, Gln or Ala); Xaa at res.30=(Ala, Ser, Pro, Gin or Asn); Xaa at res.31=(Phe, Leu or Tyr); Xaa at res.33=(Leu, Val or Met); Xaa at res.34=(Asn, Asp, Ala, Thr or Pro); Xaa at res.35=(Ser, Asp, Glu, Leu, Ala or Lys); Xaa at res.36=(Tyr, Cys, His, Ser or Ile); Xaa at res.37=(Met, Phe, Gly or Leu); Xaa at res.38=(Asn, Ser or Lys); Xaa at res.39=(Ala, Ser, Gly or Pro); Xaa at res.40=(Thr, Leu or Ser); Xaa at res.44=(Ile, Val or Thr); Xaa at res.45=(Val, Leu or Ile); Xaa at res.46=(Gln or Arg); Xaa a res.47=(Thr, Ala or Ser); Xaa at res.48=(Leu or Ile); Xaa at res.49=(Val or Met); Xaa at res.50=(His, Asn or Arg); Xaa at res.51=(Phe, Leu, Asn, Ser, Ala or Val); Xaa at res.52=(Ile, Met, Asn, Ala, Val or Leu); Xaa at res.53= (Asn, Lys, Ala, Glu, Gly or Phe); Xaa at res.54=(Pro, Ser or Val); Xaa at res.55=(Glu, Asp, Asn, Gly, Val or Lys); Xaa at res.56=(Thr, Ala, Val, Lys, Asp, Tyr, Ser, Ala, Pro or His); Xaa at res.57=(Val, Ala or Ile); Xaa at res.58=(Pro or Asp); Xaa at res.59=(Lys, Leu or Glu); Xaa at res.60=(Pro or Ala); Xaa at res.63=(Ala or Val); Xaa at res.65=(Thr, Ala or Glu);

Xaa at res.66=(Gln, Lys, Arg or Glu); Xaa at res.67=(Leu, Met or Val); Xaa at res.68=(Asn, Ser, Asp or Gly); Xaa at res.69=(Ala, Pro or Ser); Xaa at res.70=(Ile, Thr, Val or Leu); Xaa at res.71=(Ser, Ala or Pro); Xaa at res.72=(Val, Met or Ile); Xaa at res.74=(Tyr or Phe); Xaa at res.75=(Phe, Tyr, Leu or His); Xaa at res.76=(Asp, Asn or Leu); Xaa at res.77=(Asp, Glu, Asn or Ser); Xaa at res.78=(Ser, Gln, Asn, Tyr or Asp); Xaa at res.79=(Ser, Asn, Asp, Glu or Lys); Xaa at res.80=(Asn, Thr or Lys); Xaa at res.82=(Ile, Val or Asn); Xaa at res.84=(Lys or Arg); Xaa at res.85=(Lys, Asn, Gln, His or Val); Xaa at res.86=(Tyr or His); Xaa at res.87=(Arg, Gln, Glu or Pro); Xaa at res.88=(Asn, Glu or Asp); Xaa at res.90=(Val, Thr, Ala or Ile); Xaa at res.92=(Arg, Lys, Val, Asp or Glu); Xaa at res.93=(Ala, Gly, Glu or Ser); Xaa at res.95=(Gly or Ala) and Xaa at res.97=(His or Arg).

```
                    Generic Sequence 6

Cys Xaa Xaa Xaa Xaa Leu Xaa Xaa Xaa Phe
     1               5                   10

Xaa Xaa Xaa Gly Trp Xaa Xaa Trp Xaa
                    15

Xaa Xaa Pro Xaa Xaa Xaa Xaa Ala
     20                  25

Xaa Tyr Cys Xaa Gly Xaa Cys Xaa
             30                  35

Xaa Pro Xaa Xaa Xaa Xaa Xaa
                    40

Xaa Xaa Xaa Asn His Ala Xaa Xaa
                 45              50

Xaa Xaa Xaa Xaa Xaa Xaa Xaa Xaa
                     55

Xaa Xaa Xaa Xaa Xaa Xaa Xaa Cys
         60                      65

Cys Xaa Pro Xaa Xaa Xaa Xaa Xaa
                 70

Xaa Xaa Xaa Leu Xaa Xaa Xaa
     75                  80

Xaa Xaa Xaa Xaa Val Xaa Leu Xaa
                 85

Xaa Xaa Xaa Xaa Met Xaa Val Xaa
     90                  95

Xaa Cys Xaa Cys Xaa
             100
``` wherein each Xaa is independently selected from a group of one or more specified amino acids as defined by the following: "Res." means "residue" and Xaa at res.2=(Lys, Arg, Ala or Gln); Xaa at res.3=(Lys, Arg or Met); Xaa at res.4=(His, Arg or Gln); Xaa at res.5=(Glu, Ser, His, Gly, Arg, Pro, Thr, or Tyr); Xaa at res.7=(Tyr or Lys); Xaa at res.8=(Val or Ile); Xaa at res.9=(Ser, Asp or Glu); Xaa at res.11=(Arg, Gln, Ser, Lys or Ala); Xaa at res.12=(Asp, Glu, or Lys); Xaa at res.13=(Leu, Val or Ile); Xaa at res.16=(Gln, Leu, Asp, His, Asn or Ser); Xaa at res.17=(Asp, Arg, Asn or Glu); Xaa at res.19=(Ile or Val); Xaa at res.20=(Ile or Val); Xaa at res.21=(Ala or Ser); Xaa at res.23-=(Glu, Gln, Leu, Lys, Pro or Arg); Xaa at res.24=(Gly or Ser); Xaa at res.25=(Tyr or Phe); Xaa at res.26 (Ala, Ser, Asp, Met, His, Gln, Leu, or Gly); Xaa at res.28=(Tyr, Asn or Phe); Xaa at res.31=(Glu, His, Tyr, Asp, Gln or Ser); Xaa at res.33=(Glu, Lys, Asp, Gln or Ala); Xaa at res.35=(Ala, Ser, Pro, Gln or Asn); Xaa at res.36=(Phe, Leu or Tyr); Xaa at res.38=(Leu, Val or Met); Xaa at res.39=(Asn, Asp, Ala, Thr or Pro); Xaa at res.40=(Ser, Asp, Glu, Leu, Ala or Lys); Xaa at res.41=(Tyr, Cys, His, Ser or Ile); Xaa at res.42=(Met, Phe, Gly or Leu); Xaa at res.43=(Asn, Ser or Lys); Xaa at res.44=(Ala, Ser, Gly or Pro); Xaa at res.45=(Thr, Leu or Ser); Xaa at res.49=(Ile, Val or Thr); Xaa at res.50=(Val, Leu or Ile); Xaa at res.51=(Gln or Arg); Xaa at res.52=(Thr, Ala or Ser); Xaa at res.53=(Leu or Ile); Xaa at res.54=(Val or Met); Xaa at res.55=(His, Asn or Arg); Xaa at res.56=(Phe, Leu, Asn, Ser, Ala or Val); Xaa at res.57=(Ile, Met, Asn, Ala, Val or Leu); Xaa at res.58=(Asn, Lys, Ala, Glu, Gly or Phe); Xaa at res.59=(Pro, Ser or Val); Xaa at res.60=(Glu, Asp, Gly, Val or Lys); Xaa at res.61=(Thr, Ala, Val, Lys, Asp, Tyr, Ser, Ala, Pro or His); Xaa at res.62=(Val, Ala or Ile); Xaa at res.63=(Pro or Asp); Xaa at res.64=(Lys, Leu or Glu); Xaa at res.65=(Pro or Ala); Xaa at res.68=(Ala or Val); Xaa at res.70=(Thr, Ala or Glu); Xaa at res.71=(Gln, Lys, Arg or Glu); Xaa at res.72=(Leu, Met or Val); Xaa at res.73=(Asn, Ser, Asp or Gly); Xaa at res.74=(Ala, Pro or Ser); Xaa at res.75=(Ile, Thr, Val or Leu); Xaa at res.76=(Ser, Ala or Pro); Xaa at res.77=(Val, Met or Ile); Xaa at res.79=(Tyr or Phe); Xaa at res.80=(Phe, Tyr, Leu or His); Xaa at res.81=(Asp, Asn or Leu); Xaa at res.82=(Asp, Glu, Asn or Ser); Xaa at res.83=(Ser, Gln, Asn, Tyr or Asp); Xaa at res.84=(Ser, Asn, Asp, Glu or Lys); Xaa at res.85=(Asn, Thr or Lys); Xaa at res.87=(Ile, Val or Asn); Xaa at res.89=(Lys or Arg); Xaa at res.90=(Lys, Asn, Gln, His or Val); Xaa at res.91=(Tyr or His); Xaa at res.92=(Arg, Gln, Glu or Pro); Xaa at res.93=(Asn, Glu or Asp); Xaa at res.95=(Val, Thr, Ala or Ile); Xaa at res.97=(Arg, Lys, Val, Asp or Glu); Xaa at res.98=(Ala, Gly, Glu or Ser); Xaa at res.100=(Gly or Ala); and Xaa at res.102=(His or Arg).

Particularly useful sequences for use as morphogens in this invention include the C-terminal domains, e.g., the C-terminal 96–102 amino acid residues of Vgl, Vgr-1, DPP, OP-1, OP-2, CBMP-2A, CBMP-2B, GDF-1 (see Table II, below, and Seq. ID Nos. 5–14), as well as proteins comprising the C-terminal domains of 60A, BMP3, BMP5 and BMP6 (see Seq. ID Nos. 24–28), all of which include at least the conserved seven cysteine skeleton. In addition, biosynthetic constructs designed from the generic sequences, such as COP-1, 3–5, 7, 16, disclosed in U.S. Pat. No. 5,011,691, also are useful. Accordingly, other useful proteins are those exhibiting morphogenic activity and having amino acid sequences sharing at least 70% amino acid sequence homology or "similarity", and preferably 80% homology or similarity with any of the sequences above. These are anticipated to include allelic variants, species variants and other sequence variants (e.g., "muteins" or "mutant proteins"), whether naturally occurring or biosynthetically produced, as well as novel members of this morphogenic family of proteins.

As used herein, "amino acid sequence homology" is understood to mean amino acid sequence similarity, and homologous sequences-share identical or similar amino acids, where similar amino acids are conserved amino acids as defined by Dayoff et al., *Atlas of Protein Sequence and Structure*; vol. 5, Suppl.3, pp. 345–362 (M. O. Dayoff, ed., Nat'l BioMed. Research Fdn., Washington D.C. 1978.) Thus, a candidate sequence sharing 70% amino acid homology with a reference sequence requires that, following alignment of the candidate sequence with the reference sequence, 70% of the amino acids in the candidate sequence are identical to the corresponding amino acid in the reference sequence, or constitute a conserved amino acid change thereto. "Amino acid sequence identity" is understood to require identical amino acids between two aligned sequences. Thus, a candidate sequence sharing 60% amino acid identity with a reference sequence requires that, following alignment of the candidate sequence with the reference sequence, 60% of the amino acids in the candidate sequence are identical to the corresponding amino acid in the reference sequence.

AS used herein, all homologies and identities calculated use OP-1 as the reference sequence. Also as used herein, sequences are aligned for homology and identity calculations using the method of Needleman et al. (1970) *J. Mol. Biol.* 48: 443–453 and identities calculated by the Align program (DNAstar, Inc.) In all cases, internal gaps and amino acid insertions in the candidate sequence as aligned are ignored when making the homology/identity calculation.

The currently most preferred protein sequences useful as morphogens in this invention include those having greater than 60% identity, preferably greater than 65% identity, with the amino sequence defining the conserved seven cysteine skeleton of hOP1 (e.g., residues 38–139 of Seq. ID No. 5). These most preferred sequences include both allelic and species variants of the OP-1 and OP-2 proteins, including the *Drosophila* 60A protein. Accordingly, in another preferred aspect of the invention, useful morphogens include active proteins comprising species of polypeptide chains having the generic amino acid sequence herein referred to as "OPX", which accommodates the homologies between the various identified species of OP1 and OP2 (Seq. ID No. 0.29).

In still another preferred aspect of the invention, useful morphogens include active proteins comprising polypeptide chains encoded by nucleic acids which hybridize to DNA or RNA sequences encoding the C-terminal sequence defining the conserved cysteine domain, e.g., nucleotides 1036–1341 and nucleotides 1390–1695 of Seq. Id. Nos. 16 and 20, respectively, of OP1 or OP2 under stringent hybridization conditions. As used herein, stringent hybridization conditions are defined as hybridization in 40% formamide, 5×SSPE, 5× Denhardt's Solution, and 0.1% SDS at 37° C. overnight, and washing in 0.1×SSPE, 0.1% SDS at 50° C.

The morphogens useful in the methods, composition and devices of this invention include proteins comprising any of the polypeptide chains described above, whether isolated from naturally-occurring sources, or produced by recombinant DNA or other synthetic techniques, and includes allelic and species variants of these proteins, naturally-occurring or biosynthetic mutants thereof, as well as various truncated and fusion constructs. Deletion or addition mutants also a envisioned to be active, including those which may alter the conserved C-terminal cysteine skeleton, provided that the alteration does not functionally disrupt the relationship of these cysteines in the folded structure. Accordingly, such active forms are considered the equivalent of the specifically described constructs disclosed herein. The proteins may include forms having varying glycosylation patterns, varying N-termini, a family of related proteins having regions of amino acid sequence homology, and active truncated or mutated forms of native or biosynthetic proteins, produced by expression of recombinant DNA in host cells.

The morphogenic proteins can be expressed from intact or truncated cDNA or from synthetic DNAs in procaryotic or eucaryotic host cells, and purified, cleaved, refolded, and dimerized to form morphogenically active compositions. Currently preferred host cells include *E. coli* or mammalian cells, such as CHO, COS or BSC cells. A detailed description of the morphogens useful in the methods, compositions and devices of this invention is disclosed in copending U.S. patent application Ser. No. 752, 764, filed Aug. 30, 1991, and Ser. No. 667, 274, filed Mar. 11, 1991, the disclosure of which are incorporated herein by reference.

Thus, in view of this disclosure, skilled genetic engineers can isolate genes from cDNA or genomic libraries of various different species which encode appropriate amino acid sequences, or construct DNAs from oligonucleotides, and then can express them in various types of host cells, including both procaryotes and eucaryotes, to produce large quantities of active proteins capable of maintaining neural pathways in a mammal, including enhancing the survival of neurons at risk of dying and stimulating nerve regeneration and repair in a variety of mammals, including humans.

The foregoing and other objects, features and advantages of the present invention will be made more apparent from the following detailed description of the invention.

BRIEF DESCRIPTION OF THE DRAWINGS

The foregoing and other objects and features of this invention, as well as the invention itself, may be more fully understood from the following description, when read together with the accompanying drawings, in which.

DETAILED DESCRIPTION OF THE INVENTION

Figure 1A:
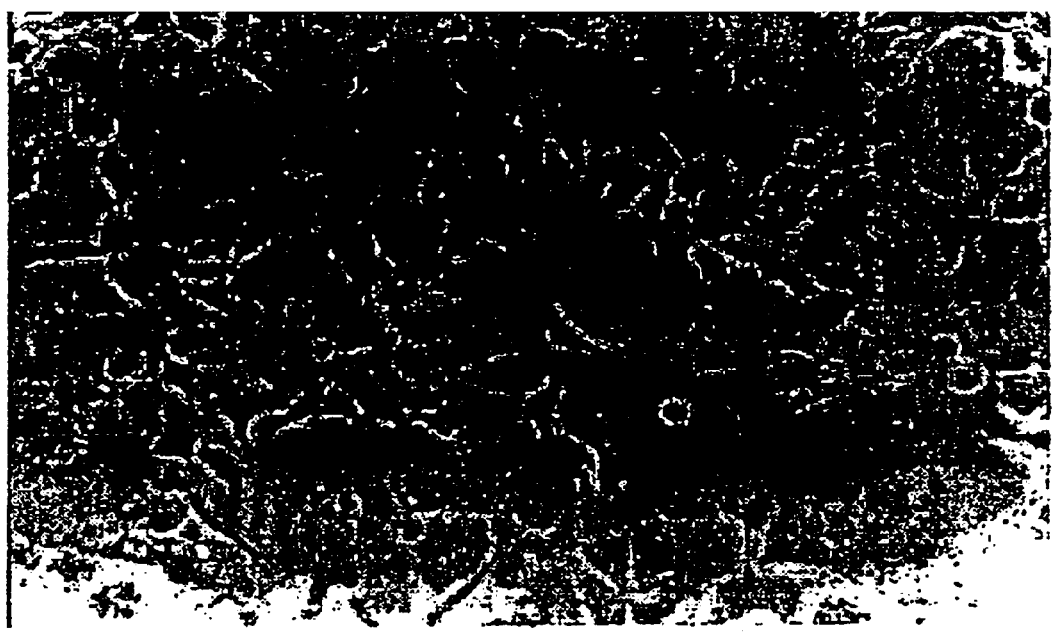
FIG. 1(A and B) are photomicrographs illustrating the ability of morphogen (OP-1) to induce transformed neuroblastoma x glioma cells (1A) to redifferentiate to a morphology characteristic of untransformed neurons (1B)

It now has been discovered that the proteins described herein are effective agents for enhancing the survival of neurons, particularly neurons at risk of dying, and for maintaining neural pathways in a mammal. As described herein, these proteins ("morphogens") can enhance survival of non-mitotic neurons, stimulate neuronal CAM expression, maintain the phenotypic expression of differentiated neurons, induce the redifferentiation of transformed cells of neural origin, and stimulating axonal growth over breaks in neural processes, particularly large gaps in distal axons. The proteins also can provide a neuroprotective effect to alleviate the tissue destructive effects associated with immunologically-related nerve tissue damage. Finally, the proteins can be used in a method for monitoring the viability of nerve tissue in a mammal.

Provided below are detailed descriptions of suitable morphogens useful in the methods, compositions and devices of this invention, as well as methods for their administration and application, and numerous, nonlimiting examples which 1) illustrate the suitability of the morphogens and morphogen-stimulating agents described herein as therapeutic agents for maintaining nerual pathways in a mammal and enhancing survival of neuronal cells at risk of dying; and 2) provide assays with which to test candidate morphogens and morphogen-stimulating agents for their efficacy.

I. Useful Morphogens

As defined herein a protein is morphogenic if it can induce the developmental cascade of cellular and molecular events that culminates in the formation of new, organ-specific tissue and comprises at least the conserved C-terminal seven cysteine skeleton of human OP1 or its functional equivalent (see supra). Specifically, the morphogens generally can elicit all of the following biological responses in an orderly fashion, when disposed in a morphogenically permissive environment: stimulating proliferation of progenitor cells; stimulating the differentiation of progenitor cells; stimulating the proliferation of differentiated cells; and supporting the growth and maintenance of differentiated cells. Each of these biological responses is elicited upon productive interaction (binding) between the morphogen and a morphogen-specific receptor displayed by the stimulated cells. Further, each of the foregoing biological responses, culminating with the morphogenesis of new or replacement functional tissue of a desired, specific organ or tissue type, is elicited in a morphogenically permissive environment. This permissive environment is free of or contains reduced levels of signals that inhibit morphogenesis. Further, the permissive environment contains signals informing uncommitted progenitor cells of a desired morphogenic pathway. Such informative signals can induce progenitor cells to commit, for example, to morphogenetic pathways leading to bone, liver, nerve, periodontal tissue, gastrointestinal mucosa or other specific tissue types. "Signals" thus include diffusible molecules (e.g. cytokines, lymphokines, differentiative factors, chemoattractants, chemotrophic factors, and other cell products) and substantially indiffusible molecules (e.g., extracellular matrix components such as collagen, laminin, fibronectin; cell attached or cell surface molecules, such as cell adhesion molecules, cadherins and the like).

Details of how the morphogens useful in the method of this invention first were identified, as well as a description on how to make, use and test them for morphogenic activity are disclosed in international application US92/01968 (WO92/15323), the disclosure of which is hereby incorporated by reference. US92/01968 describes in particular a preferred test for morphogenic activity which tests whether a suspected morphogen can elicit the full developmental cascade of endochondral bone morphogenesis when sorbed on a matrix and implanted in a mammal at a nonbony site.

This test essentially follows the teachings of Sampath et al. (1983), 80 *Proc. Natl. Acad. Sci. USA* 6591–6595. Thus, a candidate morphogen or morphogen composition, such as a matrix composition, is surgically injected or implanted in a mammal by conventional means. The extent of any resulting morphogenesis preferably is assessed by histological sectioning and staining. Surgically excised implants are fixed in Bouin's Solution, embedded in parrafin, and cut into 6–8 $\mu$m sections. Staining with toluidine blue or haematoxylin/eosin demonstrates clearly the ultimate development (morphogenesis) of new tissue. Twelve day implants are usually sufficient to determine whether the candidate induces formation of new tissue.

Thus, successful implants exhibit a controlled progression through the stages of induced tissue development, allowing one to identify and follow the tissue-specific events that occur. For example, in the Sampath et al. (1983) assay, the following stages of endochondral bone formation may be observed:

(1) leukocytes on day one;
(2) mesenchymal cell migration and proliferation on days two and three;
(3) chondrocyte appearance on days five and six;
(4) cartilage matrix formation on day seven;
(5) cartilage calcification on day eight;
(6) vascular invasion, appearance of osteoblasts, and formation of new bone on days nine and ten;
(7) appearance of osteoclasts and bone remodeling and dissolution of the implanted matrix on days twelve to eighteen; and
(8) hematopoietic bone marrow differentiation in the ossicle on day twenty-one.

In addition to histological evaluation, biological markers may be used to monitor tissue morphogenesis. Useful markers include tissue-specific enzymes whose activity may be assayed (e.g., spectrophotometrically) after homogenization of the implant. These assays may be useful for quantitation and for obtaining an estimate of tissue formation quickly after the implant is removed from the animal. For example, alkaline phosphatase activity may be used as a marker for osteogenesis.

The morphogen to be assayed according to the above-described exemplary procedures can be purified from naturally-sourced material, or can be recombinantly produced from procaryotic or eucaryotic host cells, into which genetic material encoding a morphogen, e.g., genetic material bearing one of the nucleic acid sequences disclosed herein, has been introduced. Alternatively, the above-described exemplary procedures can be used to determine whether a novel protein suspected of being a morphogen indeed has morphogenic activity. It should be recognized and appreciated that the endochondral bone assay is a representative example of morphogenesis of a variety of specific tissues and organs, particularly tissues and organs of mesenchymal origin. Caplan (1991), 9 *J. Orthopedic Res.* 641–650. Thus, analogous systems can be devised through no more than routine experimentation in light of the guidance provided in US92/01968 to assess morphogenesis of liver (U.S. Ser. No. 07/946,238, the teachings of which are incorporated herein by reference) or other tissues including nerve tissue as described herein. As disclosed in US92/01968, the morphogens can be purified from naturally-sourced material or recombinantly produced from procaryotic or eucaryotic host cells, using the genetic sequences disclosed therein. Alternatively, novel morphogenic sequences can be identified following the procedures disclosed therein.

Particularly useful morphogens include the naturally-sourced proteins listed in Table II. Other useful morphogens include biosynthetic constructs such as those disclosed in U.S. Pat. No. 5,011,691, the disclosure of which is incorporated herein by reference (e.g., COP-1, COP-3, COP-4, COP-5, COP-7, and COP-16). Still other useful morphogens include OP3, disclosed in U.S. Ser. No. 07/971,091, dorsalin-1, disclosed in Basler et al. (1993), 73 *Cell* 687–702 and GDF5, disclosed in Storm et al. (1994), 368 *Nature* 639–643, the teachings of each of which are incorporated herein by reference.

Accordingly, the morphogens useful in the methods and compositions of this invention also may be described by morphogenically active proteins having amino acid sequences sharing 70% or, preferably, 80% homology (similarity) with any of the sequences described above, where "homology" is as defined herein above.

Structural features of the morphogens useful in the method of this invention also can be described by any of the six Generic Sequences described herein (Generic Sequences 1, 2, 3, 4, 5 and 6). Generic Sequence 6 provides a preferred definition of the structural features of a morphogen useful in the present invention.

Table II, set forth below, compares the amino acid sequences of the active regions of native proteins that have been identified as morphogens, including human OP-1 (hOP-1, Seq. ID Nos. 5 and 16–17), mouse OP-1 (mOP-1Seq. ID Nos. 6 and 18–19), human and mouse OP-2 (Seq. ID Nos. 7, 8, and 20–23), CBMP2A (Seq. ID No. 9), CBMP2B (Seq. ID No. 10), BMP3 (Seq. ID No. 26), DPP (from *Drosophila*, Seq. ID No. 11), Vgl, (from *Xenopus*, Seq. ID No. 12), Vgr-1 (from mouse, Seq. ID No. 13), GDF-1 (from mouse, Seq. ID Nos. 14, 32 and 33), 60A protein (from *Drosophila*, Seq. ID Nos. 24 and 25), BMP5 (Seq. ID No. 27) and BMP6 (Seq. ID No. 28). The sequences are aligned essentially following the method of Needleman et al. (1970) *J. Mol. Biol.,* 48: 443–453, calculated using the Align Program (DNAstar, Inc.) In the table, three dots indicates that the amino acid in that position is the same as the amino acid in hOP-1. Three dashes indicates that no amino acid is present in that position, and are included for purposes of illustrating homologies. For example, amino acid residue 60 of CBMP-2A and CBMP-2B is "missing". Of course, both these amino acid sequences in this region comprise Asn-Ser (residues 58, 59), with CBMP-2A then comprising Lys and Ile, whereas CBMP-2B comprises Ser and Ile.

TABLE II

| | 1 | | | | 5 | | | |
|---|---|---|---|---|---|---|---|---|
| hOP-1 | Cys | Lys | Lys | His | Glu | Leu | Tyr | Val |
| mOP-1 | — | — | — | — | — | — | — | — |
| hOP-2 | — | Arg | Arg | — | — | — | — | — |
| mOP-2 | — | Arg | Arg | — | — | — | — | — |
| DPP | — | Arg | Arg | — | Ser | — | — | — |
| Vg1 | — | — | Lys | Arg | His | — | — | — |
| Vgr-1 | — | — | — | — | Gly | — | — | — |
| CBMP-2A | — | — | Arg | — | Pro | — | — | — |
| CBMP-2B | — | Arg | Arg | — | Ser | — | — | — |
| BMP3 | — | Ala | Arg | Arg | Tyr | — | Lys | — |
| GDF-1 | — | Arg | Ala | Arg | Arg | — | — | — |
| 60A | — | Gln | Met | Glu | Thr | — | — | — |
| BMP5 | — | — | — | — | — | — | — | — |
| BMP6 | — | Arg | — | — | — | — | — | — |
| | | | | | | | | |
| | | | | | | | | |
| | | | 10 | | | | 15 | |
| hOP-1 | Ser | Phe | Arg | Asp | Leu | Gly | Trp | Gln | Asp |
| mOP-1 | — | — | — | — | — | — | — | — | — |
| hOP-2 | — | — | Gln | — | — | — | — | Leu | — |
| mOP-2 | Ser | — | — | — | — | — | — | Leu | — |
| DPP | Asp | — | Ser | — | Val | — | — | Asp | — |
| Vg1 | Glu | — | Lys | — | Val | — | — | — | Asn |
| Vgr-1 | — | — | Gln | — | Val | — | — | — | — |
| CBMP-2A | Asp | — | Ser | — | Val | — | — | Asn | — |
| CBMP-2B | Asp | — | Ser | — | Val | — | — | Asn | — |
| BMP3 | Asp | — | Ala | — | Ile | — | — | Ser | Glu |
| GDF-1 | — | — | — | Glu | Val | — | — | His | Arg |
| 60A | Asp | — | Lys | — | — | — | — | His | — |
| BMP5 | — | — | — | — | — | — | — | — | — |
| BMP6 | — | — | Gln | — | — | — | — | — | — |
| | | | | | | | | |
| | | | | | | | | |
| | | | | | | 15 | | |
| hOP-1 | Trp | Ile | Ile | Ala | Pro | Glu | Gly | Tyr | Ala |
| mOP-1 | — | — | — | — | — | — | — | — | — |
| hOP-2 | — | Val | — | — | — | Gln | — | — | Ser |
| mOP-2 | — | Val | — | — | — | Gln | — | — | Ser |
| DPP | — | — | Val | — | — | Leu | — | — | Asp |
| Vg1 | — | Val | — | — | — | Gln | — | — | Met |
| Vgr-1 | — | — | — | — | — | Lys | — | — | — |
| CBMP-2A | — | — | Val | — | — | Pro | — | — | His |
| CBMP-2B | — | — | Val | — | — | Pro | — | — | Gln |
| BMP3 | — | — | — | Ser | — | Lys | Ser | Phe | Asp |
| GDF-1 | — | Val | — | — | — | Arg | — | Phe | Leu |
| 60A | — | — | — | — | — | — | — | — | Gly |
| BMP5 | — | — | — | — | — | — | — | — | — |
| BMP6 | — | — | — | — | — | Lys | — | — | — |
| | | | | | | | | |
| | | | 20 | | | | 25 | |
| hOP-1 | Ala | Tyr | Tyr | Cys | Glu | Gly | Glu | Cys | Ala |
| mOP-1 | — | — | — | — | — | — | — | — | — |
| hOP-2 | — | — | — | — | — | — | — | — | Ser |
| mOP-2 | — | — | — | — | — | — | — | — | — |

TABLE II-continued

| Protein | | | | | | | | | |
|---|---|---|---|---|---|---|---|---|---|
| DPP | — | — | — | — | His | — | Lys | — | Pro |
| Vg1 | — | Asn | — | — | Tyr | — | — | — | Pro |
| Vgr-1 | — | Asn | — | — | Asp | — | — | — | Ser |
| CBMP-2A | — | Phe | — | — | His | — | Glu | — | Pro |
| CBMP-2B | — | Phe | — | — | His | — | Asp | — | Pro |
| BMP3 | — | — | — | — | Ser | — | Ala | — | Gln |
| GDF-1 | — | Asn | — | — | Gln | — | Gln | — | — |
| 60A | — | Phe | — | — | Ser | — | — | — | Asn |
| BMP5 | — | Phe | — | — | Asp | — | — | — | Ser |
| BMP6 | — | Asn | — | — | Asp | — | — | — | Ser |

Positions 30–35:

| Protein | | | | | | | | | |
|---|---|---|---|---|---|---|---|---|---|
| hOP-1 | Phe | Pro | Leu | Asn | Ser | Tyr | Met | Asn | Ala |
| mOP-1 | — | — | — | — | — | — | — | — | — |
| hOP-2 | — | — | — | Asp | — | Cys | — | — | — |
| mOP-2 | — | — | — | Asp | — | Cys | — | — | — |
| DPP | — | — | — | Ala | Asp | His | Phe | — | Ser |
| Vg1 | Tyr | — | — | Thr | Glu | Ile | Leu | — | Gly |
| Vgr-1 | — | — | — | — | Ala | His | — | — | — |
| CBMP-2A | — | — | — | Ala | Asp | His | Leu | — | Ser |
| CBMP-2B | — | — | — | Ala | Asp | His | Leu | — | Ser |
| GDF-1 | Leu | — | Val | Ala | Leu | Ser | Gly | Ser** | — |
| BMP3 | — | — | Met | Pro | Lys | Ser | Leu | Lys | Pro |
| 60A | — | — | — | — | Ala | His | — | — | — |
| BMP5 | — | — | — | — | Ala | His | Met | — | — |
| BMP6 | — | — | — | — | Ala | His | Met | — | — |

Positions 40:

| Protein | | | | | | | | | |
|---|---|---|---|---|---|---|---|---|---|
| hOP-1 | Thr | Asn | His | Ala | Ile | Val | Gln | Thr | Leu |
| mOP-1 | — | — | — | — | — | — | — | — | — |
| hOP-2 | — | — | — | — | — | Leu | — | Ser | — |
| mOP-2 | — | — | — | — | — | Leu | — | Ser | — |
| DPP | — | — | — | — | Val | — | — | — | — |
| Vg1 | Ser | — | — | — | — | Leu | — | — | — |
| Vgr-1 | — | — | — | — | — | — | — | — | — |
| CBMP-2A | — | — | — | — | — | — | — | — | — |
| CBMP-2B | — | — | — | — | — | — | — | — | — |
| BMP3 | Ser | — | — | — | Thr | Ile | — | Ser | Ile |
| GDF-1 | Leu | — | — | — | Val | Leu | Arg | Ala | — |
| 60A | — | — | — | — | — | — | — | — | — |
| BMP5 | — | — | — | — | — | — | — | — | — |
| BMP6 | — | — | — | — | — | — | — | — | — |

Positions 45–50:

| Protein | | | | | | | | | |
|---|---|---|---|---|---|---|---|---|---|
| hOP-1 | Val | His | Phe | Ile | Asn | Pro | Glu | Thr | Val |
| mOP-1 | — | — | — | — | — | — | Asp | — | — |
| hOP-2 | — | His | Leu | Met | Lys | — | Asn | Ala | — |
| mOP-2 | — | His | Leu | Met | Lys | — | Asp | Val | — |
| DPP | — | Asn | Asn | Asn | — | — | Gly | Lys | — |
| Vg1 | — | — | Ser | — | Glu | — | — | Asp | Ile |
| Vgr-1 | — | — | Val | Met | — | — | — | Tyr | — |
| CBMP-2A | — | Asn | Ser | Val | — | Ser | — | Lys | Ile |
| CBMP-2B | — | Asn | Ser | Val | — | Ser | — | Ser | Ile |
| BMP3 | — | Arg | Ala** | Gly | Val | Val | Pro | Gly | Ile |
| GDF-1 | Met | — | Ala | Ala | Ala | — | Gly | Ala | Ala |
| 60A | — | — | Leu | Leu | Glu | — | Lys | Lys | — |
| BMP5 | — | — | Leu | Met | Phe | — | Asp | His | — |
| BMP6 | — | — | Leu | Met | — | — | — | Tyr | — |

Positions 55–60:

| Protein | | | | | | | | | |
|---|---|---|---|---|---|---|---|---|---|
| hOP-1 | Pro | Lys | Pro | Cys | Cys | Ala | Pro | Thr | Gln |
| mOP-1 | — | — | — | — | — | — | Asp | — | — |
| hOP-2 | — | — | Ala | — | — | — | — | — | Lys |
| mOP-2 | — | — | Ala | — | — | — | — | — | Lys |
| DPP | — | — | Ala | — | — | Val | — | — | — |
| Vg1 | — | Leu | — | — | — | Val | — | — | Lys |
| Vgr-1 | — | — | — | — | — | — | — | — | Lys |
| CBMP-2A | — | — | Ala | — | — | Val | — | — | Glu |
| CBMP-2B | — | — | Ala | — | — | Val | — | — | Glu |
| BMP3 | — | Glu | — | — | — | Val | — | Gly | Lys |
| GDF-1 | Asp | Leu | — | — | — | Val | — | Ala | Arg |
| 60A | — | — | — | — | — | — | — | — | Arg |
| BMP5 | — | — | — | — | — | — | — | — | Lys |
| BMP6 | — | — | — | — | — | — | — | — | Lys |

Positions 65–70:

| Protein | | | | | | | | | |
|---|---|---|---|---|---|---|---|---|---|
| hOP-1 | Leu | Asn | Ala | Ile | Ser | Val | Leu | Tyr | Phe |
| mOP-1 | — | — | — | — | — | — | — | — | — |
| hOP-2 | — | Ser | — | Thr | — | — | — | — | Tyr |
| mOP-2 | — | Ser | — | Thr | — | — | — | — | Tyr |
| Vg1 | Met | Ser | Pro | — | — | Met | — | Phe | Tyr |
| Vgr-1 | Val | — | — | — | — | — | — | — | — |
| DPP | — | Asp | Ser | Val | Ala | Met | — | — | Leu |
| CBMP-2A | — | Ser | — | — | — | Met | — | — | Leu |

TABLE II-continued

| Protein | | | | | | | | | |
|---|---|---|---|---|---|---|---|---|---|
| CBMP-2B | — | Ser | — | — | — | Met | — | — | Leu |
| BMP3 | Met | Ser | Ser | Leu | — | Ile | — | Phe | Tyr |
| GDF-1 | — | Ser | Pro | — | — | — | — | Phe | — |
| 60A | — | Gly | — | Leu | Pro | — | — | — | His |
| BMP5 | — | — | — | — | — | — | — | — | — |
| BMP6 | — | — | — | — | — | — | — | — | — |
|  |  |  |  | 75 |  |  |  |  | 80 |
| hOP-1 | Asp | Asp | Ser | Ser | Asn | Val | Ile | Leu | Lys |
| mOP-1 | — | — | — | — | — | — | — | — | — |
| hOP-2 | — | Ser | — | Asn | — | — | — | — | Arg |
| mOP-2 | — | Ser | — | Asn | — | — | — | — | Arg |
| DPP | Asn | — | Gln | — | Thr | — | Val | — | — |
| Vg1 | — | Asn | Asn | Asp | — | — | Val | — | Arg |
| Vgr-1 | — | — | Asn | — | — | — | — | — | — |
| CBMP-2A | — | Glu | Asn | Glu | Lys | — | Val | — | — |
| CBMP-2B | — | Glu | Tyr | Asp | Lys | — | Val | — | — |
| BMP3 | — | Glu | Asn | Lys | — | — | Val | — | — |
| GDF-1 | — | Asn | — | Asp | — | — | Val | — | Arg |
| 60A | Leu | Asn | Asp | Glu | — | — | Asn | — | — |
| BMP5 | — | — | — | — | — | — | — | — | — |
| BMP6 | — | — | Asp | — | — | — | — | — | — |
|  |  |  |  |  | 85 |  |  |  |  |
| hOP-1 | Lys | Tyr | Arg | Asn | Met | Val | Val | Arg |  |
| mOP-1 | — | — | — | — | — | — | — | — |  |
| hOP-2 | — | His | — | — | — | — | — | Lys |  |
| mOP-2 | — | His | — | — | — | — | — | Lys |  |
| DPP | Asn | — | Gln | Glu | — | Thr | — | Val |  |
| Vg1 | His | — | Glu | — | — | Ala | — | Asp |  |
| Vgr-1 | — | — | — | — | — | — | — | — |  |
| CBMP-2A | Asn | — | Gln | Asp | — | — | — | Glu |  |
| CBMP-2B | Asn | — | Gln | Glu | — | — | — | Glu |  |
| BMP3 | Val | — | Pro | — | — | Thr | — | Glu |  |
| GDF-1 | Gln | — | Glu | Asp | — | — | — | Asp |  |
| 60A | — | — | — | — | — | Ile | — | Lys |  |
| BMP5 | — | — | — | — | — | — | — | — |  |
| BMP6 | — | — | — | Trp | — | — | — | — |  |
| | 90 | | | | | 95 | | | |
| hOP-1 | Ala | Cys | Gly | Cys | His |  |  |  |  |
| mOP-1 | — | — | — | — | — |  |  |  |  |
| hOP-2 | — | — | — | — | — |  |  |  |  |
| mOP-2 | — | — | — | — | — |  |  |  |  |
| DPP | Gly | — | — | — | Arg |  |  |  |  |
| Vg1 | Glu | — | — | — | Arg |  |  |  |  |
| Vgr-1 | — | — | — | — | — |  |  |  |  |
| CBMP-2A | Gly | — | — | — | Arg |  |  |  |  |
| CBMP-2B | Gly | — | — | — | Arg |  |  |  |  |
| BMP3 | Ser | — | Ala | — | Arg |  |  |  |  |
| GDF-1 | Glu | — | — | — | Arg |  |  |  |  |
| 60A | Ser | — | — | — | — |  |  |  |  |
| BMP5 | Ser | — | — | — | — |  |  |  |  |
| BMP6 | — | — | — | — | — |  |  |  |  |
| | | | 100 | | | | | | |

**Between residues 56 and 57 of BMP3 is a Val residue; between residues 43 and 44 of GDF-1 lies the amino acid sequence Gly-Gly-Pro-Pro.

As is apparent from the foregoing amino acid sequence comparisons, significant amino acid changes can be made within the generic sequences while retaining the morphogenic activity. For example, while the GDF-1 protein sequence depicted in Table II shares only about 50% amino acid identity with the hOP1 sequence described therein, the GDF-1 sequence shares greater than 70% amino acid sequence homology (or "similarity") with the hOP1 sequence, where "homology" or "similarity" includes allowed conservative amino acid changes within the sequence as defined by Dayoff, et al., *Atlas of Protein Sequence and Structure* vol.5, supp.3, pp. 345–362, (M. O. Dayoff, ed., Nat'l BioMed. Res. Fd'n, Washington D.C. 1979.)

The currently most preferred protein sequences useful as morphogens in this invention include those having greater than 60% identity, preferably greater than 65% identity, with the amino acid sequence defining the conserved seven cysteine skeleton of hOP1 (e.g., residues 38–139 of Seq. ID No. 5). These most preferred sequences include both allelic and species variants of the OP-1 and OP-2 proteins, including the *Drosophila* 60A protein. Accordingly, in still another preferred aspect, the invention includes morphogens comprising species of polypeptide chains having the generic amino acid sequence referred to herein as "OPX", which defines the seven cysteine skeleton and accommodates the identities between the various identified mouse and human OP1 and OP2 proteins. OPX is-presented in Seq. ID No. 29. As described therein, each Xaa at a given position independently is selected from the residues occurring at the corresponding position in the C-terminal sequence of mouse or human OP1 or OP2 (see Seq. ID Nos. 5–8 and/or Seq. ID Nos. 16–23).

Accordingly, each "Xaa" at a given position in OPX (SEQ ID NO:29) independently is selected from the residues occurring at the corresponding position in the C-terminal sequence of mouse or human OP-1 or-OP-2. Specifically, each "Xaa" is independently selected from a group of one or more specified amino acids as defined below:

```
Cys  Xaa  Xaa  His  Glu  Leu  Tyr  Val  Ser  Phe  Xaa  Asp  Leu  Gly  Trp
1                    5                        10                        15

Xaa  Asp  Trp  Xaa  Ile  Ala  Pro  Xaa  Gly  Tyr  Xaa  Ala  Tyr  Tyr  Cys
               20                             25                        30

Glu  Gly  Glu  Cys  Xaa  Phe  Pro  Leu  Xaa  Ser  Xaa  Met  Asn  Ala  Thr
                    35                        40                        45

Asn  His  Ala  Ile  Xaa  Gln  Xaa  Leu  Val  His  Xaa  Xaa  Xaa  Pro  Xaa
                    50                        55                        60

Xaa  Val  Pro  Lys  Xaa  Cys  Cys  Ala  Pro  Thr  Xaa  Leu  Xaa  Ala  Xaa
                    65                        70                        75

Ser  Val  Leu  Tyr  Xaa  Asp  Xaa  Ser  Xaa  Asn  Val  Ile  Leu  Xaa  Lys
                    80                        85                        90

Xaa  Arg  Asn  Met  Val  Xaa  Ala  Cys  Gly  Cys  His
                    95                        100
``` wherein Xaa at res.2=(Lys or Arg); Xaa at res.3=(Lys or Arg); Xaa at res.11=(Arg or Gln); Xaa at res.16=(Gin or Leu); Xaa at res.19=(Ile or Val); Xaa at res.23=(Glu or Gln); Xaa at res.26=(Ala or Ser); Xaa at res.35=(Ala or Ser); Xaa at res.39=(Asn or Asp); Xaa at res.41=(Tyr or Cys); Xaa at res.50=(Val or Leu); Xaa at res.52=(Ser or Thr); Xaa at res.56=(Phe or Leu); Xaa at res.57=(Ile or Met); Xaa at res.58=(Asn or Lys); Xaa at res.60=(Glu, Asp or Asn); Xaa at res.61=(Thr, Ala or Val); Xaa at res.65=(Pro or Ala); Xaa at res.71=(Gln or Lys); Xaa at res.73=(Asn or Ser); Xaa at res.75=(Ile or Thr); Xaa at res.80=(Phe or Tyr); Xaa at res.82=(Asp or Ser); Xaa at res.84=(Ser or Asn); Xaa at res.89=(Lys or Arg); Xaa at res.91=(Tyr or His); and Xaa at res.97=(Arg or Lys).

II. Formulations and Methods for Administering Therapeutic Agents

The morphogens can be administered to an individual by any suitable means, preferably directly (e.g., locally, as by injection to a nerve tissue locus) or systemically (e.g., parenterally or orally). Where the morphogen is to be administered parenterally, such as by intravenous, subcutaneous, intramuscular, intraorbital, ophthalmic, intraventricular, intracranial, intracapsular, intraspinal, intracisternal, intraperitoneal, buccal, rectal, vaginal, intranasal or by aerosol administration, the morphogen preferably comprises part of an aqueous solution. The solution is physiologically acceptable so that in addition to delivery of the desired morphogen to the patient, the solution does not otherwise adversely affect the patient's electrolyte and volume balance. The aqueous medium for the morphogen thus may comprise normal physiologic saline (9.85% NaCl, 0.15M), pH 7–7.4. The aqueous solution containing the morphogen can be made, for example, by dissolving the protein in 50% ethanol containing acetonitrile in 0.1% trifluoroacetic acid (TFA) or 0.1% HCl, or equivalent solvents. One volume of the resultant solution then is added, for example, to ten volumes of phosphate buffered saline (PBS), which further may include 0.1–0.2% human serum albumin (HSA). The resultant solution preferably is vortexed extensively. If desired, a given morphogen can be made more soluble by association with a suitable molecule. For example, association of the mature dimer with the pro domain of the morphogen increases solubility of the protein significantly (see Section II.1, below). In fact, the endogenous protein is thought to be transported in this form. Another molecule effective for enhancing solubility and particularly useful for oral administrations, is casein. For example, addition of 0.2% casein increases solubility of the mature active form of OP-1 by 80%. Other components found in milk and/or various serum proteins also may be useful.

Useful solutions for parenteral administration can be prepared by a variety of methods well known in the pharmaceutical art, described, for example, in *Remington's Pharmaceutical Sciences* (Gennaro, A., ed.), Mack Pub., 1990. Formulations can include, for example, polyalkylene glycols such as polyethylene glycol, oils of vegetable origin, hydrogenated naphthalenes, and the like. Formulations for direct administration, in particular, can include glycerol and other compositions of high viscosity. Biocompatible, preferably bioresorbable, polymers, including, for example, hyaluronic acid, collagen, polybutyrate, tricalcium phosphate, lactide and lactide/glycolide copolymers, can be useful excipients to control the release of the morphogen in vivo. Other potentially useful parenteral delivery systems for these morphogens include ethylene-vinyl acetate copolymer particles, osmotic pumps, implantable infusion systems, and liposomes. Formulations for inhalation administration contain as excipients, for example, lactose, or can be aqueous solutions containing, for example, polyoxyethylene-9-lauryl ether, glycocholate and deoxycholate, or oily solutions for administration in the form of nasal drops, or as a gel to be applied intranasally. Formulations for parenteral administration can also include glycocholate for buccal administration, methoxysalicylate for rectal administration, or cutric acid for vaginal administration.

Alternatively, the morphogens described herein can be administered orally. Oral administration of proteins as therapeutics generally is not practiced as most proteins are readily degraded by digestive enzymes and acids in the mammalian digestive system before they can be absorbed into the bloodstream. However, the morphogens described herein typically are acid stable and protease-resistant (see, for example, U.S. Pat. No. 4,968,590.) In addition, at least one morphogen, OP-1, has been identified in mammary gland extract, colostrum and 57-day milk. Moreover, the OP-1 purified from mammary gland extract is morphogenically active. Specifically, this protein induces endochondral bone formation in mammals when implanted subcutaneously in association with a suitable matrix material, using a standard in vivo bone assay, such as is disclosed in U.S. Pat. No. 4,968,590. Moreover, the morphogen also is detected in the bloodstream (see Example 9, below). Finally, soluble form morphogen, e.g., mature morphogen associated with the pro domain, is capable of maintaining neural pathways in a mammal (See Examples 4 and 6 below). These findings indicate that oral and parenteral administration are viable means for administering morphogens to an individual. In addition, while the mature forms of certain morphogens described herein typically are sparingly soluble, the morphogen form found in milk (and mammary gland extract and colostrum) is readily soluble, probably by association of the mature, morphogenically active form with part or all of the pro domain of the intact sequence and/or by association with one or more milk components. Accordingly, the compounds provided herein also can be associated with molecules capable of enhancing their solubility in vitro or in vivo.

The compounds provided herein also can be associated with molecules capable of targeting the morphogen or morphogen-stimulating agent to nerve tissue. For example, an antibody, antibody fragment, or other binding protein that interacts specifically with a surface molecule on nerve tissue cells, including neuronal or glial cells, can be used. Useful targeting molecules can be designed, for example, using the single chain binding site technology disclosed, for example, in U.S. Pat. No. 5,091,513.

As described above, the morphogens provided herein share significant sequence homology in the C-terminal active domains. By contrast, the sequences typically diverge significantly in the sequences which define the pro domain. Accordingly, the pro domain is thought to be morphogen-specific. As described above, it is also known that the various morphogens identified to date are differentially expressed in the different tissues. Accordingly, without being limited to any given theory, it is likely that, under natural conditions in the body, selected morphogens typically act on a given tissue. Accordingly, part or all of the pro domains which have been identified associated with the active form of the morphogen in solution, can serve as targeting molecules for the morphogens described herein. For example, the pro domains can interact specifically with one or more molecules at the target tissue to direct the morphogen associated with the pro domain to that tissue. Accordingly, another useful targeting molecule for targeting morphogen to nerve tissue is part or all of a morphogen pro domain, particularly part or all of the pro domains of OP-1 or GDF-1, both of which proteins are found naturally associated with nerve tissue.

Finally, the morphogens or morphogen-stimulating agents provided herein can be administered alone or in combination with other molecules known to be beneficial in maintaining neural pathways, including anti-inflammatory agents and nerve trophic (growth) factors.

Nerve trophic factors as defined herein refer to proteins able to stimulate survival and growth of nerve cells. Most of the characterized actions of nerve trophic actors relate to developmental events and suggest that the temporal and local regulation of expression of these proteins plays a role during maturation of the nervous system. Nerve trophic factors are also important in the function of the adult nervous system for the maintenance of structural integrity and regulation of plasticity. Such processes are altered in neurodegenerative diseases and neurodegenerative events following acute injury to the nervous system. This has prompted speculation that nerve trophic factors are involved in the structural alterations which occur in response to injury and disease.

Nerve trophic factors are found among several protein families including neurotrophins fibroblast growth factors, the epidermal-growth factor-protein family, and lymphokines to name a few. Nerve growth factor (NGF) is the best characterized member of the nerve trophic factor protein families. NGF belongs to the protein family called neurotrophins, the other known members of which are brain-derived neurotrophic factor (BDNF), neurotrophin-3 (NT-3), neurotrophin-4 (NT-4), and neurotrophin-5 (NT-5). Individual neurotrophins are highly conserved among mammalian species and share at least about 50%, preferably at least 60%, amino acid sequence homology with other members of this group. In particular, nerve trophic factors that are suitable for use herein have amino acid sequences comprising a sequence sharing at least 60% homology with each of the sequences of human NGF, human BDNF, human NT-3, human NT-4, and human NT-5. Alternatively, nerve trophic factors can include mammalian proteins comprising amino acid sequences having six cysteine residues at relative positions that are strictly conserved and in common with the sequences of nerve trophic factors from rats, humans, chickens, and frogs.

The compounds provided herein can be formulated into pharmaceutical compositions by admixture with pharmaceutically acceptable nontoxic excipients and carriers. As noted above, such compositions can be prepared for parenteral administration, particularly in the form of liquid solutions or suspensions; for oral administration, particularly in the form of tablets or capsules; or intranasally, particularly in the form of powders, nasal drops, or aerosols.

The compositions can be formulated for parenteral or oral administration to humans or other mammals in therapeutically effective amounts, e.g., amounts which provide appropriate concentrations for a time sufficient to eliminate or reduce the patient's pathological condition, to provide therapy for the neurological diseases and disorders described above, and amounts effective to enhance neural cell survival an/or to protect neurons and neural pathways in anticipation of injury to nerve tissue.

As will be appreciated by those skilled in the art, the concentration of the compounds described in a therapeutic composition will vary depending upon a number of factors, including the dosage of the drug to be administered, the chemical characteristics (e.g., hydrophobicity) of the compounds employed, and the route of administration. The preferred dosage of drug to be administered also is likely to depend on such variables as the type and extent of progression of the neurological disease, the overall health status of the particular patient, the relative biological efficacy of the compound selected, the formulation of the compound, excipients, and its route of administration. In general terms, the compounds of this invention can be provided in an aqueous physiological buffer solution containing about 0.1 to 10% w/v compound for parenteral administration. Typical dose ranges are from about 10 ng/kg to about 1 g/kg of body weight per day; a preferred dose range is from about 0.1 $\mu$g/kg to 100 mg/kg of body weight per day. Optimally, the morphogen dosage given in all cases is between 2–20 $\mu$g of protein per kilogram weight of the patient per day. No obvious OP-1 induced pathological lesions are induced when mature morphogen (e.g., OP-1, 20 $\mu$g) is administered daily to normal growing rats for 21 consecutive days. Moreover, 10 $\mu$g systemic injections of morphogen (e.g., OP-1) injected daily for 10 days into normal newborn mice does not produce any gross abnormalties.

Since the ability of proteins and protein fragments to penetrate the blood-brain barrier can be related to their size, lipophilicity or their net ionic charge, suitable modifications of the morphogens can be formulated (e.g., by substituting pentafluorophenylalanine for phenylalanine, or by conjugation to a cationized protein such as albumin) to increase their transportability across the barrier, using standard methodologies known in the art. See, for example, Kastin et al., *Pharmac. Biochem. Behav.* (1979) 11: 713–716; Rapoport et al., *Science* (1980) 207: 84–86; Pardridge et al., (1987) *Biochem. Biophys. Res. Commun.* 146: 307–313; Riekkinen et al., (1987) *Peptides* 8: 261–265. The efficacy of these functional analogs can be assessed for example, by evaluating the ability of these compounds to induce redifferentiation of transformed cells, or enhance survival of neurons at risk of dying, as described in the Examples provided herein.

In administering morphogens systemically in the methods of the present invention, preferably a large volume loading dose is used at the start of the treatment. The treatment then is continued with a maintenance dose. Further administration then can be determined by monitoring at intervals the levels of the morphogen in the blood.

Where injury to neurons of a neural pathway is induced deliberately as part of for example, a surgical procedure, the morphogen preferably is provided just prior to, or concomitant with induction of the trauma. Preferably, the morphogen is administered prophylactically in a surgical setting. Optimally, the morphogen dosage given in all cases is between 2–20 µg of protein per kilogram weight of the patient.

Alternatively, an effective amount of an agent that stimulates endogenous morphogen levels can be administered by any of the routes described above. For example, an agent effective for stimulating morphogen production and/or secretion from nerve tissue cells can be provided to a mammal, e.g., by direct administration of the morphogen stimulating agent to glial cells associated with the nerve tissue to be treated. A method for identifying and testing agents capable of modulating the levels of endogenous morphogens in a given tissue is described generally herein in Example 13, and in detail in internatinal application US92/07359 (WO93/015172), the disclosure of which is incorporated herein by reference. Briefly, candidate compounds can be identified and tested by incubating the compound in vitro with a test tissue or cells thereof, for a time sufficient to allow the compound to affect the production, i.e., the expression and/or secretion, of a morphogen that said cells are competent to produce. Here, suitable tissue or cultured cells of a tissue preferably would comprise neurons and/or glial cells. For example, suitable tissue for testing can includes cultured cells isolated from the substantia nigra, adendema glial cells, and the like.

A currently preferred detection means for evaluating the level of the morphogen in culture upon exposure to the candidate compound comprises an immunoassay utilizing an antibody or other suitable blinding protein capable of reacting specifically with a morphogen and being detected as part of a complex with the morphogen. Immunoassays can be performed using standard techniques known in the art and antibodies raised against a morphogen and specific for that morphogen. As described herein, morphogen stimulating agents can be isolated from natural-sourced material or they can be recombinantly produced or chemically synthesized by those skilled in the art of medicinal chemistry. Agents effective for stimulating endogenous morphogens then can formulated into pharmaceutical preparations and administered as described herein.

Where the morphogen is to be provided to a site to stimulate axon regeneration, the morphogen preferably is provided to the site in association with a biocompatible, preferably bioresorbable carrier suitable for maintaining a protein at a site in vivo, and through which a neural process can regenerate. A currently preferred carrier also comprises sufficient structure to assist direction of axonal growth. Currently preferred carriers include structural molecules such as collagen, hyaluronic acid or laminin, and/or synthetic polymers or copolymers of, for example, polylactic acid, polyglycolic acid or polybutyric acid. Currently most preferred are carriers comprising tissue extracellular matrix. These can be obtained commercially. In addition, a brain tissue-derived extracellular matrix can be prepared as described in international application US92/01968 (WO92/15323), incorporated hereinabove by reference, and/or by other means known in the art.

The currently-preferred means for-repairing breaks in neural pathways, particularly pathways of the peripheral nervous system, include providing the morphogen to the site as part of a device that includes a biocompatible membrane or casing of a dimension sufficient to span the break and having openings adapted to receive severed nerve ends. The morphogen is disposed within the casing, preferably dispersed throughout a suitable carrier, and is accessible to the severed nerve ends. Alternatively, the morphogen can be adsorbed onto the interior surface of the casing, or otherwise associated therewith. In addition, currently preferred casings have an impermeable exterior surface. The casing acts as a nerve guidance channel, aiding in directing axonal growth. In addition, the casing also protects the damaged nerve from immunologically-related agents which can assist in scar tissue formation. Suitable channel or casing materials include silicone or bioresorbable materials such as collagen, hyaluronic acid, laminin, polylactic acid, polyglycolic acid, polybutyric acid and the like. Additionally, although the nerve guidance channels described herein generally are tubular in shape, it should be evident to those skilled in the art that various alternative shapes can be employed. The lumen of the guidance channels can, for example, be oval or even square in cross section. Moreover the guidance channels can be constructed of two or more parts which can be clamped together to secure the nerve stumps. Nerve endings can be secured to the nerve guidance channels by means of sutures, biocompatible adhesives such as fibrin glue, or other means known in the medical art.

II.1 Soluble Morphogen Complexes

A currently preferred form of the morphogen useful in therapeutic formulations, having improved solubility in aqueous solutions and consisting essentially of amino acids, is a dimeric morphogenic protein comprising at least the 100 amino acid peptide sequence having the pattern of seven or more cysteine residues characteristic of the morphogen family complexed with a peptide comprising part or all of a pro region of a member of the morphogen family, or an allelic, species or other sequence variant thereof. Preferably, the dimeric morphogenic protein is complexed with two peptides. Also, the dimeric morphogenic protein preferably is noncovalently complexed with the pro region peptide or peptides. The pro region peptides also preferably comprise at least the N-terminal eighteen amino acids that define a given morphogen pro region. In a most preferred embodiment, peptides defining substantially the full length pro region are used.

Other soluble forms of morphogens include dimers of the uncleaved pro forms of these proteins, as well as "hemi-dimers" wherein one subunit of the dimer is an uncleaved pro form of the protein, and the other subunit comprises the mature form of the protein, including truncated forms thereof, preferably noncovalently associated with a cleaved pro domain peptide.

As described above, useful pro domains include the full length pro regions, as well as various truncated forms hereof, particularly truncated forms cleaved at proteolytic Arg-Xaa-Xaa-Arg cleavage sites. For example, in OP-1, possible pro sequences include sequences defined by residues 302–292 (full length form); 48–292; and 158–292. Soluble OP-1 complex stability is enhanced when the pro region comprises the full length form rather than a truncated form, such as the 48–292 truncated form, in that residues 30–47 show sequence homology to the N-terminal portions of other morphogens, and are believed to have particular utility in enhancing complex stability for all morphogens. Accordingly, currently preferred pro sequences are those encoding the full length form of the pro region for a given morphogen. Other pro sequences contemplated to have utility include biosynthetic pro sequences, particularly those that incorporate a sequence derived from the N-terminal portion of one or more morphogen pro sequences.

As will be appreciated by those having ordinary skill-in the art, useful sequences encoding the pro region can be obtained from genetic sequences encoding known morphogens. Alternatively, chimeric pro regions can be constructed from the sequences of one or more known morphogens. Still another option is to create a synthetic sequence variant of one or more known pro region sequences.

In another preferred aspect, useful pro region peptides include polypeptide chains comprising an amino acid sequence encoded by a nucleic acid that hybridizes under stringent conditions with a DNA or RNA sequence encoding at least the N-terminal eighteen amino acids of the pro region sequence for OP1 or OP2, e.g., nucleotides 136–192 and 152–211 of Seq. ID No. 16 and 20, respectively.

A. Isolation of Soluble Morphogen Complex from Conditioned Media or Body Fluid

Morphogens are expressed from mammalian cells as soluble complexes. Typically, however the complex is most often disassociated during purification, generally by exposure to denaturants often added to the purification solutions, such as detergents, alcohols, organic solvents, chaotropic agents and compounds added to reduce the pH of the solution. Provided below is a currently preferred protocol for purifying the soluble proteins from conditioned media (or, optionally, a body fluid such as serum, cerebro-spinal or peritoneal fluid), under non-denaturing conditions. The method is rapid, reproducible and yields isolated soluble morphogen complexes in substantially pure form.

Soluble morphogen complexes can be isolated from conditioned media using a simple, three step chromatographic protocol performed in the absence of denaturants. The protocol involves running the media (or body fluid) over an affinity column, followed by ion exchange and gel filtration chromatographies. The affinity column described below is a Zn-IMAC column. The present protocol has general applicability to the purification of a variety of morphogens, all of which are anticipated to be isolatable using only minor modifications of the protocol described below. An alternative protocol also envisioned to have utility an immunoaffinity column, created using standard procedures and, for example, using antibody specific for a given morphogen pro domain (complexed, for example, to a protein A-conjugated Sepharose column.) Protocols for developing immunoaffinity columns are well described in the art, (see, for example, *Guide to Protein Purification*, M. Deutscher, ed., Academic Press, San Diego, 1990, particularly sections VII and XI.)

In this experiment human OP-1 was expressed in mammalian CHO (chinese hamster ovary) cells as described in the art (see, for example, international application US90/05903 (WO91/05802).) The CHO cell conditioned media containing 0.5% FBS was initially purified using Immobilized Metal-Ion Affinity Chromatography (IMAC). The soluble OP-1 complex from conditioned media binds very selectively to the Zn-IMAC resin and a high concentration of imidazole (50 mM imidazole, pH 8.0) is required for the effective elution of the bound complex. The Zn-IMAC step separates the soluble OP-1 from the bulk of the contaminating serum proteins that elute in the flow through and 35 mM imidazole wash fractions. The Zn-IMAC purified soluble OP-1 is next applied to an S-Sepharose cation-exchange column equilibrated in 20 mM $NaPO_4$ (pH 7.0) with 50 mM NaCl. This S-Sepharose step serves to further purify and concentrate the soluble OP-1 complex in preparation for the following gel filtration step. The protein was applied to a Sephacryl S-200HR column equilibrated in TBS. Using substantially the same protocol, soluble morphogens also can be isolated from one or more body fluids, including serum, cerebro-spinal fluid or peritoneal fluid.

IMAC was performed using Chelating-Sepharose (Pharmacia) that had been charged with three column volumes of 0.2 M $ZnSO_4$. The conditioned media was titrated to pH 7.0 and applied directly to the ZN-IMAC resin equilibrated in 20 mM HEPES (pH 7.0) with 500 mM NaCl. The Zn-IMAC resin was loaded with 80 mL of starting conditioned media per mL of resin. After loading, the-column was washed with equilibration buffer and most of the contaminating proteins were eluted with 35 mM imidazole (pH 7.0) in equilibration buffer. The soluble OP-1 complex then is eluted with 50 mM imidazole (pH 8.0) in 20 mM HEPES and 500 mM NaCl.

The 50 mM imidazole eluate containing the soluble OP-1 complex was diluted with nine volumes of 20 mM $NaPO_4$ (pH 7.0) and applied to an S-Sepharose (Pharmacia) column equilibrated in 20 mM $NaPO_4$ (pH 7.0) with 50 mM NaCl. The S-Sepharose resin was loaded with an equivalent of 800 mL of starting conditioned media per mL of resin. After loading the S-Sepharose column was washed with equilibration buffer and eluted with 100 mM NaCl followed by 300 mM and 500 mM NaCl in 20 mM $NaPO_4$ (pH 7.0). The 300 mM NaCl pool was further purified using gel filtration chromatography. Fifty mls of the 300 mm NaCl eluate was applied to a 5.0×90 cm Sephacryl S-200HR (Pharmacia) equilibrated in Tris buffered saline (TBS), 50 mM Tris, 150 mM NaCl (pH 7.4). The column was eluted at a flow rate of 5 mL/minute collecting 10 mL fractions. The apparent molecular of the soluble OP-1 was determined by comparison to protein molecular weight standards (alcohol dehydrogenase (ADH, 150 kDa), bovine serum albumin (BSA, 68 kDa), carbonic anhydrase (CA, 30 kDa) and cytochrome C (cyt C, 12.5 kDa). The purity of the S-200 column fractions was determined by separation on standard 15% polyacrylamide SDS gels stained with coomassie blue. The identity of the mature OP-1 and the pro-domain was determined by N-terminal sequence analysis after separation of the mature OP-1 from the pro-domain using standard reverse phase C18 HPLC.

The soluble OP-1 complex elutes with an apparent molecular weight of 110 kDa. This agrees well with the predicted composition of the soluble OP-1 complex with one mature OP-1 dimer (35–36 kDa) associated with two pro-domains (39 kDa each). Purity of the final complex can be verified by running the appropriate fraction in a reduced 15% polyacrylamide gel.

The complex components can be verified by running the complex-containing fraction from the S-200 or S-200HR columns over a reverse phase C18 HPLC column and eluting in an acetonitrile gradient (in 0.1% TFA), using standard procedures. The complex is dissociated by this step, and the pro domain and mature species elute as separate species. These separate species then can be subjected to N-terminal sequencing using standard procedures (see, for example, *Guide to Protein Purification*, M. Deutscher, ed., Academic Press, San Diego, 1990, particularly pp. 602–613), and the identity of the isolated 36 kD, 39 kDa proteins confirmed as mature morphogen and isolated, cleaved pro domain, respectively. N-terminal sequencing of the isolated pro domain from mammalian cell produced OP-1 revealed 2 forms of the pro region, the intact form (beginning at residue 30 of Seq. ID No. 16) and a truncated form, (beginning at residue 48 of Seq. ID No. 16.) N-terminal sequencing of the polypeptide subunit of the isolated mature species reveals a range of N-termini for the mature sequence, beginning at residues 293, 300, 313, 315, 316, and 318, of Seq. ID No. 16, all of which are active as demonstrated by the standard bone induction assay.

B. In Vitro Soluble Morphogen Complex Formation

As an alternative to purifying soluble complexes from culture media or a body fluid, soluble complexes can be formulated from purified pro domains and mature dimeric species. Successful complex formation apparently requires association of the components under denaturing conditions sufficient to relax the folded structure of these molecules, without affecting disulfide bonds. Preferably, the denaturing conditions mimic the environment of an intracellular vesicle sufficiently such that the cleaved pro domain has an opportunity to associate with the mature dimeric species under relaxed folding conditions. The concentration of denaturant in the solution then is decreased in a controlled, preferably step-wise manner, so as to allow proper refolding of the dimer and pro regions while maintaining the association of the pro domain with the dimer. Useful denaturants include 4–6M urea or guanidine hydrochloride (GuHCl), in buffered solutions of pH 4–10, preferably pH 6–8. The soluble complex then is formed by controlled dialysis or dilution into a solution having a final denaturant concentration of less than 0.1–2M urea or GuHCl, preferably 1–2 M urea of GuHCl, which then preferably can be diluted into a physiological buffer. Protein purification/renaturing procedures and considerations are well described in the art, and details for developing a suitable renaturing protocol readily can be determined by one having ordinary skill in the art. One useful text one the subject is *Guide to Protein Purification*, M. Deutscher, ed., Academic Press, San Diego, 1990, particularly section V. Complex formation also can be aided by addition of one or more chaperone proteins.

C. Stability of Soluble Morphogen Complexes

The stability of the highly purified soluble morphogen complex in a physiological buffer, e.g., tris-buffered saline (TBS) and phosphate-buffered saline (PBS), can be enhanced by any of a number of means. Currently preferred is by means of a pro region that comprises at least the first 18 amino acids of the pro sequence (e.g., residues 30–47 of Seq. ID NO. 16 for OP-1), and preferably is the full length pro region. Residues 30–47 show sequence homology to the N-terminal portion of other morphogens and are believed to have particular utility in enhancing complex stability for all morphogens. Other useful means for enhancing the stability of soluble morphogen complexes include three classes of additives. These additives include basic amino acids (e.g., L-arginine, lysine and betaine); nonionic detergents (e.g., Tween 80 or NonIdet P-120); and carrier proteins (e.g., serum albumin and casein). Useful concentrations of these additives include 1–100 mM, preferably 10–70 mM, including 50 mM, basic amino acid;, 0.01–1.0%, preferably 0.05–0.2%, including 0.1% (v/v) nonionic detergent;, and 0.01–1.0%, preferably 0.05–0.2%, including 0.1% (w/v) carrier protein.

III. EXAMPLES

Example 1

Identification of Morphogen-Expressing Tissue

Determining the tissue distribution of morphogens can be used to identify different morphogens expressed in a given tissue, as well as to identify new, related morphogens. Tissue distribution also can be used to identify useful morphogen-producing tissue for use in screening and identifying candidate morphogen-stimulating agents. The morphogens (or their mRNA transcripts) readily are identified in different tissues using standard methodologies and minor modifications thereof in tissues where expression can be low. For example, protein distribution can be determined using standard Western blot analysis or immunofluorescent techniques, and antibodies specific to the morphogen or morphogens of interest. Similarly, the distribution of morphogen transcripts can be determined using standard Northern hybridization or in situ hybridization protocols and transcript-specific probes.

Any probe capable of hybridizing specifically to a transcript, and distinguishing the transcript of interest from other, related transcripts can be used. Because the morphogens described herein share such high sequence homology in their active, C-terminal domains, the tissue distribution of a specific morphogen transcript can best be determined using a probe specific for the pro region of the protein and/or the N-terminal region of the mature protein. Another useful sequence is the 3' non-coding region flanking and immediately following the stop codon. These portions of the sequence vary substantially among the morphogens of this invention, and accordingly, are specific for each protein. For example, a particularly useful Vgr-1-specific probe sequence is the PvuII-SacI fragment, a 265 bp fragment encoding both a portion of the pro region and the N-terminus of the mature sequence (see Lyons et al. (1989) *PNAS* 86: 4554–4558 for a description of the cDNA (sequence). Similarly, particularly useful mOP-1-specific-probe-sequences-are the BstX1-BglII fragment, a 0.68 Kb sequence that covers approximately two-thirds of the mOP-1 pro region; a StuI—StuI fragment, a 0.2 Kb sequence immediately upstream of the 7-cysteine domain; and the Ear1-Pst1 fragment, an 0.3 Kb fragment containing a portion of the 3'untranslated sequence (See Seq. ID No. 18, where the pro region is defined essentially by residues 30–291.) Similar approaches can be used, for example, with hOP-1 (Seq. ID No. 16) or human or mouse OP-2 (Seq. ID Nos. 20 and 22.)

Using these morphogen-specific probes, which can be synthetically engineered or obtained from cloned sequences, morphogen transcripts can be identified in mammalian tissue, using standard methodologies well known to those having ordinary skill in the art. Briefly, total RNA is prepared from various adult murine tissues (e.g., liver, kidney, testis, heart, brain, thymus and stomach) by a standard methodology such as by the method of Chomczyaski et al. ((1987) *Anal. Biochem* 162: 156–159) and described below. Poly (A)+ RNA is prepared by using oligo (dT)-cellulose chromatography (e.g., Type 7, from Pharmacia LKB Biotechnology, Inc.). Poly (A)+ RNA (generally 15 $\mu$g) from each tissue is fractionated on a 1% agarose/formaldehyde gel and transferred onto a Nytran membrane (Schleicher & Schuell). Following the transfer, the membrane is baked at 80° C. and the RNA is cross-linked under UV light (generally 30 seconds at 1 mW/cm$^2$). Prior to hybridization, the appropriate probe is denatured by heating. The hybridization is carried out in a lucite cylinder rotating in a roller bottle apparatus at approximately 1 rev/min for approximately 15 hours at 37° C. using a hybridization mix of 40% formamide, 5× Denhardts, 5×SSPE, and 0.1% SDS. Following hybridization, the non-specific counts are washed off the filters in 0.1×SSPE, 0.1% SDS at 50° C.

Examples demonstrating the tissue distribution of various morphogens, including vgr-1, OP-1, BMP2, BMP3, BMP4, BMP5, GDF-1, and OP-2 in developing and adult tissue are disclosed in international application US92/01968 (WO92/15323), and in Ozkaynak, et al., (1991) *Biochem. Biophys. Res. Commn.* 179: 116–123, and Ozkaynak, et al. (1992) *J. Biol. Chem.* 267: 25220–25227. Using the general probing methodology described herein, northern blot hybridizations using probes specific for these morphogens to probe brain, spleen, lung, heart, liver and kidney tissue indicate that kidney-related tissue appears to be the primary expression source for OP-1, with brain, heart and lung tissues being secondary sources. Lung tissue appears to be the primary tissue expression source for Vgr-1, BMP5, BMP4 and BMP3. Lower levels of Vgr-1 also are seen in kidney and heart tissue, while the liver appears to be a secondary expression source for BMP5, and the spleen appears to be a secondary expression source for BMP4. GDF-1 appears to be expressed primarily in brain tissue. To date, OP-2 appears to be expressed primarily in early embryonic tissue. Specifically, northern blots of murine embryos and 6-day post-natal animals shows abundant OP2 expression in 8-day embryos. Expression is reduced significantly in 17-day embryos and is not detected in post-natal animals.

Example 2

Morphogen Localization in the Nervous System

Morphogens have been identified in developing and adult rat brain and spinal cord tissue, as determined both by northern blot hybridization of morphogen-specific probes to mRNA extracts from developing and adult nerve tissue (see Example 1, above) and by immunolocalization studies. For example, northern blot analysis of developing rat tissue has identified significant OP-1 mRNA transcript expression in the CNS international application US92/01968 (WO92/15323), and Ozkaynak et al. (1991) *Biochem. Biophys. Res. Comm.*, 179: 11623 and Ozkaynak, et al. (1992) *J. Biol. Chem.* 267: 25220–25227. GDF-1 mRNA appears to be expressed primarily in developing and adult nerve tissue, specifically in the brain, including the cerebellum and brain stem, spinal cord and peripheral nerves (Lee, S. (1991) *PNAS* 88: 4250–4254). BMP2B (also referred in the art as BMP4) and Vgr-1 transcripts also have been reported to be expressed in nerve tissue (Jones et al. (1991) *Development* 111: 531–542), although the nerve tissue does not appear to be the primary expression tissue for these genes (Ozkaynak, et al., (1992) *J. Biol. Chem.* 267: 25220–25227. Specifically, CBMP2 transcripts are reported in the region of the diencephalon associated with pituitary development, and Vgr-1 transcripts are reported in the anteroposterior axis of the CNS, including in the roof plate of the developing neural tube, as well as in the cells immediately adjacent the floor plate of the developing neural tube. In older rats, Vgr-1 transcripts are reported in developing hippocampus tissue. In addition, the genes encoding OP-1 and BMP2 originally were identified by probing human hippocampus cDNA libraries.

Immunolocalization studies, performed using standard methodologies known in the art and disclosed in international application US92/01968 (WO92/15323), the disclosure of which is incorporated herein, localized OP-1 expression to particular areas of developing and adult rat brain and spinal cord tissue. Specifically, OP-1 protein expression was assessed in adult (2–3 months old) and five or six-day old mouse embryonic nerve tissue, using standard morphogen-specific antisera, specifically, rabbit anti-OP1 antisera, made using standard antibody protocols known in the art and preferably purified on an OP-1 affinity column. The antibody itself was labelled using standard fluorescent labelling techniques, or a labelled anti-rabbit IgG molecule was used to visualize bound OP-1 antibody.

As revealed by the above-described procedure, immunofluorescence staining demonstrated the presence of OP-1 in adult rat central nervous system (CNS.) Similar and extensive staining was seen in both the brain and spinal cord. OP-1 appeared to be localized predominantly to the extracellular matrix of the grey matter (neuronal cell bodies), distinctly present in all areas except the cell bodies themselves. In white matter, formed mainly of myelinated nerve fibers, staining appeared to be confined to astrocytes (glial cells). A similar staining pattern also was seen in newborn rat (10 day old) brain sections.

In addition, OP-1 has been specifically localized in the substantia nigra, which is composed primarily of striatal basal ganglia, a system of accessory motor neurons that function is association with the cerebral cortex and corticospinal system. Dysfunctions in this subpopulation or system of neurons are associated with a number of neuropathies, including Huntington's chorea and Parkinson's disease.

OP1 also has been localized at adendema glial cells, known to secrete factors into the cerebrospinal fluid, and which occur around the intraventricular valve, choroid fissure, and central canal of the brain in both developing and adult rat.

Finally, morphogen inhibition in developing embryos inhibits nerve tissue development. Specifically, 9-day mouse embryo cells, cultured in vitro under standard culturing conditions, were incubated in the presence and absence of an OP-1-specific monoclonal antibody prepared using recombinantly produced, purified mature OP-1 and the immunogen. The antibody was prepared using standard antibody production means well known in the art and as described generally in Example 13. After two days, the effect of the antibody on the developing embryo was evaluated by histology. As determined by histological examination, the OP-1-specific antibody specifically inhibits eye lobe formation in the developing embryo. In particular, the diencephalon outgrowth does not develop. In addition, the heart is malformed and enlarged. Moreover, in separate immunolocalization studies on embryo sections with labelled OP-1 specific antibody, the OP-1-specific antibody localizes to neural epithelia.

The endogenous morphogens which act on neuronal cells can be expressed and secreted by nerve tissue cells, e.g., by neurons and/or glial cells associated with the neurons, and/or they can be transported to the neurons by the cerebrospinal fluid and/or bloodstream. Recently, OP-1 has been identified in the human blood (See Example 9, below). In addition, transplanted Schwann cells recently have been shown to stimulate nerve fiber formation in rat spinal cord, including inducing vascularization and myelin sheath formation around at least some of the new neuronal processes (Bunge (1991) *Exp. Neurology* 114: 254–257.) The regenerative property of these cells can be mediated by the secretion of a morphogen by the Schwann cells.

Example 3

Morphogen Enhancement of Neuronal Cell Survival

The morphogens described herein enhance cell survival, particularly of neuronal cells at risk of dying. For example, fully differentiated neurons are non-mitotic and die in vitro when cultured under standard mammalian cell culture conditions, using a chemically defined or low serum medium known in the art, (see, for example, Charness (1986) *J. Biol. Chem.* 26: 3164–3169 and Freese et al. (1990) *Brain Res.* 521: 254–264.) However, if a primary culture of non-mitotic neuronal cells is treated with a morphogen, the survival of these cells is enhanced significantly. For example, a primary culture of striatal basal ganglia isolated from the substantia nigra of adult rat brain was prepared using standard procedures, e.g., by dissociation by trituration with pasteur pipette of substania nigra tissue, using standard tissue culturing protocols, and grown in a low serum medium, e.g., containing 50% DMEM (Dulbecco's modified Eagle's medium), 50% F-12 medium, heat inactivated horse serum supplemented with penicillin/streptomycin and 4 g/l glucose. Under standard culture conditions, these cells are undergoing significant cell death by three weeks when cultured in a serum free medium. Cell death is evidenced morphologically by the inability of cells to remain adherent and by changes in their ultrastructural characteristics, e.g., by chromatin clumping and organelle disintegration.

In this example, the cultured basal ganglia were were treated with chemically defined medium conditioned with 0.1–100 ng/ml OP-1. Fresh, morphogen-conditioned medium was provided to the cells every 3–4 days. Cell survival was enhanced significantly and was dose dependent upon the level of OP-1 added: cell death decreased significantly as the concentration of OP-1 was increased in cell cultures. Specifically, cells remained adherent and continued to maintain the morphology of viable differentiated neurons. In the absence of morphogen treatment, the majority of the cultured cells dissociated and underwent cell necrosis.

Dysfunctions in the basal ganglia of the sustania nigra are associated with Huntington's chorea and parkinsonism in vivo. The ability of the morphogens defined herein to enhance neuron survival indicates that these morphogens will be useful as part of a therapy to enhance survival of neuronal cells at risk of dying in vivo due, for example, to a neuropathy or chemical or mechanical trauma. It is particularly anticipated that these morphogens will provide a useful therapeutic agent to treat neuropathies which affect the striatal basal ganglia, including Huntington's chorea and Parkinson's disease. For clinical applications, the morphogen may be administered or, alternatively, a morphogen-stimulating agent can be administered.

Example 4

Morphogen-Induced Redifferentiation of Transformed Cells

The morphogens described herein also induce redifferentiation of transformed cells to a morphology characteristic of untransformed cells. In particular, the morphogens are capable of inducing redifferentiation of transformed cells of neuronal origin to a morphology characteristic of untransformed neurons. The example provided below details morphogen induced redifferentiation of a transformed cell line of neuronal origin, NG108-15. Morphogen-induced redifferentiation of transformed cells also has been shown in mouse neuroblastoma cells (NlE-115) and in human embryo carcimona cells (see international application US92/01968 (WO92/15323).

NG108-15 is a transformed hybrid cell line produced by fusing neuroblastoma x glioma cells (obtained from America Type Tissue Culture, Rockville, Md.), and exhibiting a morphology characteristic of transformed embryonic neurons, e.g., having a fibroblastic morphology. Specifically, the cells have polygonal cell bodies, short, spike-like processes and make few contacts with neighboring cells (see FIG. 1A). Incubation of NG108-15 cells, cultured in a chemically defined, serum-free medium, with 0.1 to 300 ng/ml of OP-1 for four hours induces an orderly, dose-dependent change in cell morphology.

Figure 1B:
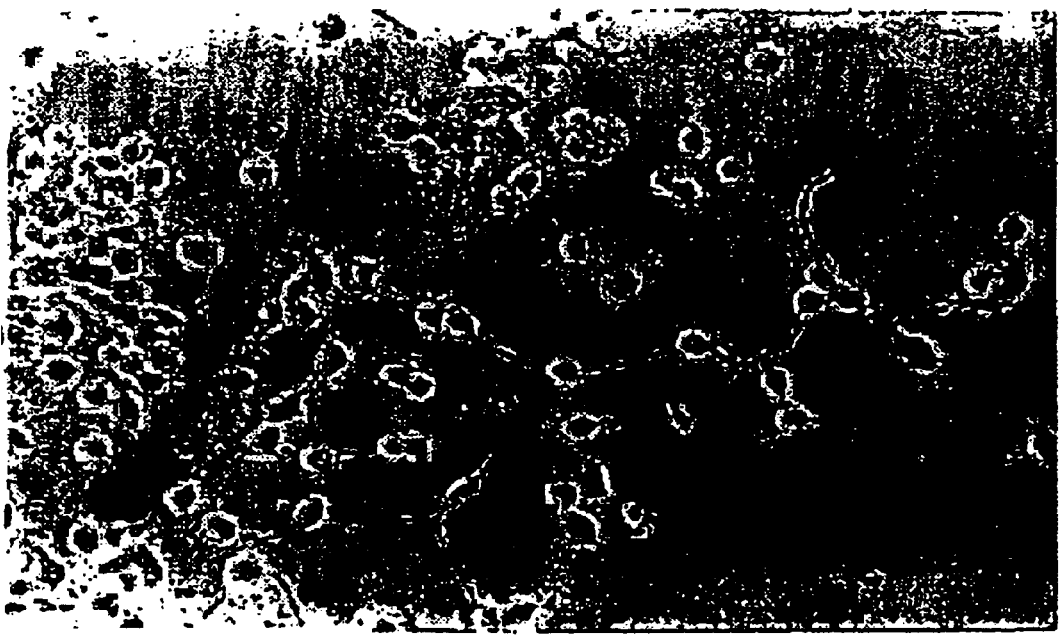

In the experiment NG108-15 cells were subcultured on poly-L-lysine coated 6-well plates. Each well contained 40–50,000 cells in 2.5 ml of chemically defined medium. On the third day 2.5 $\mu$l of OP-1 in 60% ethanol containing 0.025% trifluoroacetic was added to each well. OP-1 concentrations of 0–300 ng/ml were tested. Typically, the media was changed daily with new aliquots of OP-1, although morphogenesis can be induced by a single four hour incubation with OP-1. In addition, OP-1 concentrations of 10 ng/ml were sufficient to induce redifferentiation. After one day, hOP-1-treated cells undergo a significant change in their cellular ultrastructure, including rounding of the soma, increase in phase brightness and extension of the short neurite processes. After two days, cells treated with OP-1 begin to form epithelioid sheets, which provide the basis for the growth of mutilayered aggregates at three day's post-treatment. By four days, the great majority of OP-1-treated cells are associated in tightly-packed, mutilayered aggregates (FIG. 1B). FIG. 2 plots the mean number of multilayered aggregates or cell clumps identified in twenty randomly selected fields from six independent experiments, as a function of morphogen concentration. Forty ng/ml of OP-1 is sufficient for half maximum induction of cell aggregation.

The morphogen-induced redifferentiation occurred without any associated changes in DNA synthesis, cell division, or cell viability, making it unlikely that the morphologic changes were secondary to cell differentiation or a toxic effect of hOP-1. Moreover, the OP-1-induced morphogenesis does not inhibit cell division, as determined by $^3$H-thymidine uptake, unlike other molecules which have been shown to stimulate differentiation of transformed cells, such as butyrate, DMSO, retanoic acid or Forskolin. The data indicate that OP-1 can maintain cell stability and viability after inducing redifferentiation. In addition, the effects are morphogen specific, and redifferentiation is not induced when NG108-15 cells are incubated with 0.1–40 ng/ml TGF-$\beta$.

The experiments also have been performed with highly purified soluble morphogen (e.g., mature OP1 associated with its pro domain) which also specifically induced redifferentiation of NG110-15 cells.

The morphogens described herein accordingly provide useful therapeutic agents for the treatment of neoplasias and neoplastic lesions of the nervous system, particularly in the treatment of neuroblastomas, including retinoblastomas, and gliomas. The morphogens themselves can be administered or, alternatively, a morphogen-stimulating agent can be administered.

Example 5

Nerve Tissue Protection from Chemical Trauma

The ability of the morphogens described herein to enhance survival of neuronal cells and to induce cell aggregation and cell—cell adhesion in redifferentiated cells, indicates that the morphogens will be useful as therapeutic agents to maintain neural pathways by protecting the cells defining the pathway from the damage caused by chemical trauma. In particular, the morphogens can protect neurons, including developing neurons, from the effects of toxins known to inhibit the proliferation and migration of neurons and to interfere with cell—cell adhesion. Examples of such toxins include ethanol, one or more of the toxins present in cigarette smoke, and a variety of opiates. The toxic effects of ethanol on developing neurons induces the neurological damage manifested in fetal alcohol syndrome. The morphogens also can protect neurons from the cytoxic effects associated with excitatory amino acids such as glutamate.

For example, ethanol inhibits the cell—cell adhesion effects induced in morphogen-treated NG108-15 cells when provided to these cells at a concentration of 25–50 mM. Half maximal inhibition can be achieved with 5–10 mM ethanol, the concentration of blood alcohol in an adult following ingestion of a single alcoholic beverage. Ethanol likely interferes with the homophilic binding of CAMs between cells, rather than their induction, as morphogen-induced N-CAM levels are unaffected by ethanol. Moreover, the inhibitory effect is inversely proportional to morphogen concentration. Accordingly, it is envisioned that administration of a morphogen or morphogen-stimulating agent to neurons, particularly developing neurons, at risk of damage from exposure to toxins such as ethanol, can protect these cells from nerve tissue damage by overcoming the toxin's inhibitory effects. The morphogens described herein also are useful in therapies to treat damaged neural pathways resulting from a neuropathy induced by exposure to these toxins.

Example 6

Morphogen-Induced CAM Expression

The morphogens described herein induce CAM expression, particularly N-CAM expression, as part of their induction of morphogenesis. CAMs are morphoregulatory molecules identified in all tissues as an essential step in tissue development. N-CAMs, which comprise at least 3 isoforms (N-CAM-180, N-CAM-140 and N-CAM-120, where "180", "140" and "120", indicate the apparent molecular weights of the isoforms as measured by polyacrylamide gel electrophoresis) are expressed at least transiently in developing tissues, and permanently in nerve tissue. Both the N-CAM-180 and N-CAM-140 isoforms are expressed in both developing and adult tissue. The N-CAM-120 isoform is found only in adult tissue. Another neural CAM is L1.

N-CAMs are implicated in appropriate neural development, including appropriate nuerulation, neuronal migration, fasciculation, and synaptogenesis. Inhibition of N-CAM production, as by complexing the molecule with an N-CAM-specific antibody, inhibits retina organization, including retinal axon migration, and axon regeneration in the peripheral nervous system, as well as axon synapsis with target muscle cells. In addition, significant evidence indicates that physical or chemical trauma to neurons, oncogenic transformation and some genetic neurological disorders are accompanied by changes in CAM expression, which alter the adhesive or migratory behavior of these cells. Specifically, increased N-CAM levels are reported in Huntington's disease striatum (e.g., striatal basal ganglia), and decreased adhesion is noted in Alzheimer's disease.

The morphogens described herein can stimulate CAM production, particularly L1 and N-CAM production, including all three isoforms of the N-CAM molecule. For example, N-CAM expression is stimulated significantly in morphogen-treated NG108-15 cells. Untreated NG108-15 cells exhibit a fibroblastic, or minimally differentiated morphology and express only the 180 and 140 isoforms of N-CAM normally associated with a developing cell. Following morphogen treatment these cells exhibit a morphology characteristic of adult neurons and express enhanced levels of all three N-CAM isoforms. Using a similar protocol as described in the example below, morphogen treatment of NG108-15 cells also induced L1 expression.

Figure 2A:
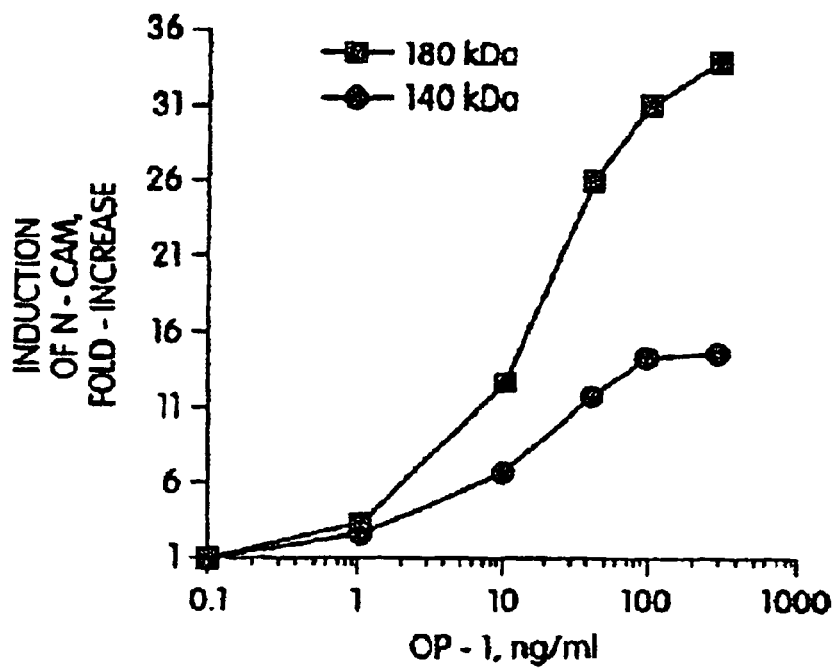
FIG. 2A is a dose response curve for the induction of the 180 kDa and 140 kDa N-CAM isoforms in morphogen-treated NG108-15 cells.
Figure 2B:
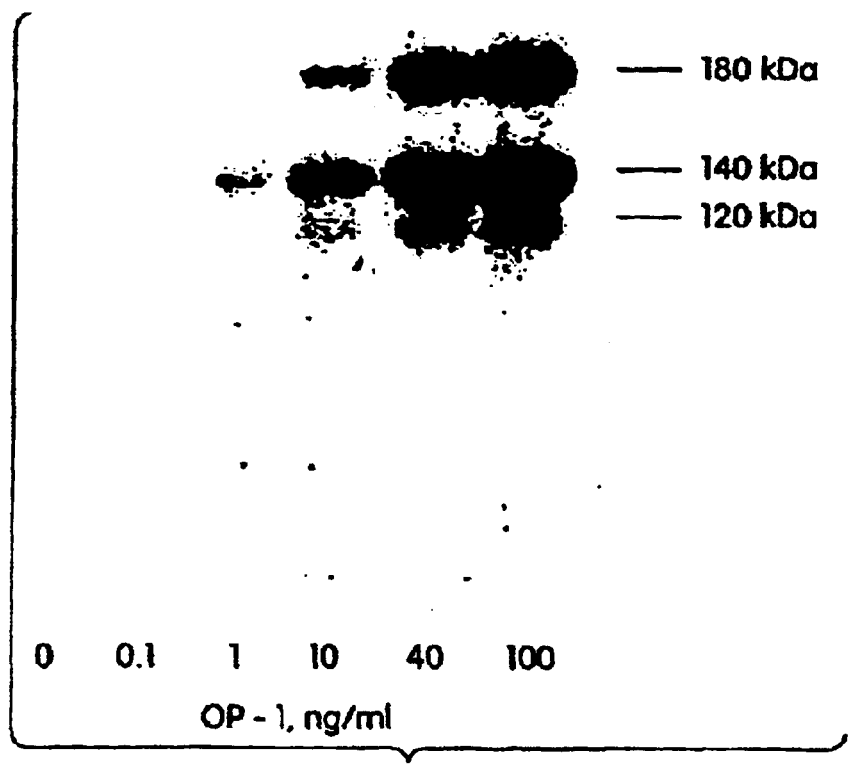
FIG. 2B is a photograph of a Western blot of whole cell extracts from morphogen-treated NG108-15 cells with an N-CAM-specific antibody.

In this example NG108-15 cells were cultured for 4 days in the presence of increasing concentrations of OP-1 and standard Western blots performed on whole cells extracts. N-CAM isoforms were detected with an antibody which crossreacts with all three isoforms, mAb H28.123, obtained from Sigma Chemical Co., St. Louis, the different isoforms being distinguishable by their different mobilities on an electrophoresis gel. Control NG108-15 cells (untreated) express both the 140 kDa and the 180 kDa isoforms, but not the 120 kDa, as determined by western blot analyses using up to 100 $\mu$g of protein. Treatment of NG108-15 cells with OP-1 resulted in a dose-dependent increase in the expression of the 180 kDa and 140 kDa isoforms, as well as the induction of the 120 kDa isoform. See FIGS. 2A and 2B. FIG. 2B is a Western blot of OP1-treated NG108-15 cell extracts, probed with mAb H28.123, showing the induction of all three isoforms. FIG. 2A is a dose response curve of N-CAM-180 and N-CAM-140 induction as a function of morphogen concentration. N-CAM-120 is not shown in the graph as it could not be quantitated in control cells. However, as is clearly evident from the Western blot in FIG. 2A, N-CAM-120 is induced in response to morphogen treatment. The differential induction of N-CAM 180 and 140 isoforms seen can be because constitutive expression of the 140 isoform is close to maximum.

Figure 3:
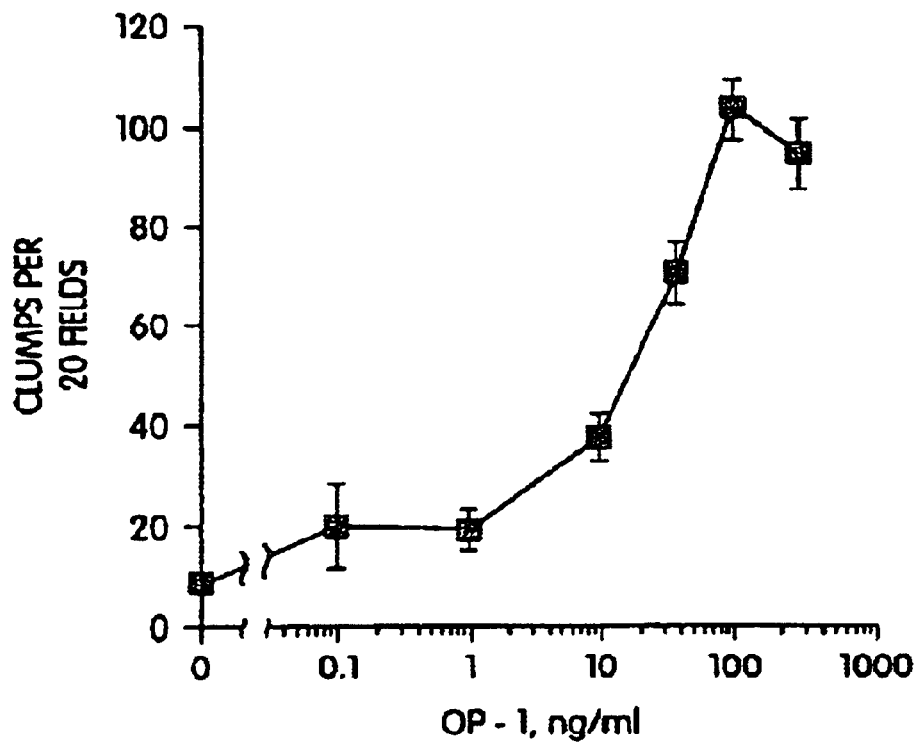
FIG. 3 is a line graph plot of the mean number of cell aggregates counted in 20 randomly selected fields as a function of morphogen concentration.

The increase in N-CAM expression corresponded in a dose-dependent manner with the morphogen induction of multicellular aggregates. Compare FIG. 2A and FIG. 3. FIG. 3 graphs the mean number of multilayered aggregates (clumps) counted per 20 randomly selected fields in 6 independent experiments, versus the concentration of morphogen. The induction of the 120 isoform also indicates that morphogen-induced redifferentiation of transformed cells stimulates not only redifferentiation of these cells from a transformed phenotype, but also differentiation to a phenotype corresponding to a developed cell. Standard immunolocalization studies performed with the mAb H28.123 on morphogen-treated cells show N-CAM cluster formation associated with the periphery and processes of treated cells and no reactivity with untreated cells. Moreover, morphogen treatment does not appear to inhibit cell division as determined by cell counting or $^3$H-thymidine uptake. Finally, known chemical differentiating agents, such as Forskolin and dimethylsulfoxide do not induce N-CAM production.

In addition, the cell aggregation effects of OP-1 on NG108-15 cells can be inhibited with anti-N-CAM antibodies or antisense N-CAM oligonucleotides. Antisense oligonucleotides can be made synthetically on a nucleotide synthesizer, using standard means known in the art. Preferably, phosphorothioate oligonucleotides ("S-oligos") are prepared, to enhance transport of the nucleotides across cell membranes. Concentrations of both N-CAM antibodies and N-CAM antisense oliognucleotides sufficient to inhibit N-CAM induction also inhibited formation of multilayered cell aggregates. Specifically, incubation of morphogen-treated NG108-115 cells with 0.3–3 $\mu$M N-CAM antisense S-oligos, 5–500 $\mu$M unmodified N-CAM antisense oligos, or 10 $\mu$g/ml mAb H28.123 significantly inhibits cell aggregation. It is likely that morphogen treatment also stimulates other CAMs, as inhibition is not complete.

The experiments also have been performed with soluble morphogen (e.g., mature OP-1 associated with its pro domain) which also specifically induced CAM expression.

The morphogens described herein are useful as therapeutic agents to treat neurological disorders associated with altered CAM levels, particularly N-CAM levels, such as Huntington's chorea and Alzheimers'-disease, and the like. In clinical applications, the morphogens themselves can be administered or, alternatively, a morphogen-stimulating agent can be administered.

The efficacy of the morphogens described herein to affect N-CAM expression can be assessed in vitro using a suitable cell line and the methods described herein.

In addition to a transformed cell line, N-CAM expression can be assayed in a primary cell culture of neural or glial cells, following the procedures described herein. The efficacy of morphogen treatment on N-CAM expression in vivo can be evaluated by tissue biopsy as described in Example 9, below, and detecting N-CAM molecules with an N-CAM-specific antibody, such as mAb H28.123, or using the animal model described in Example 11.

Alternatively, the level of N-CAM proteins or protein fragments present in cerebrospinal fluid or serum also can be detected to evaluate the effect of morphogen treatment. N-CAM molecules are known to slough off cell surfaces and have been detected in both serum and cerebrospinal fluid. In addition, altered levels of the soluble form of N-CAM are associated with normal pressure hydrocephalus and type II schizophrenia. N-CAM fluid levels can be detected following the procedure described in Example 9 and using an N-CAM specific antibody, such as mAb H28.123.

Example 7

Morphogen-Induced Nerve Gap Repair (PNS)

The morphogens described herein also stimulate peripheral nervous system axonal growth over extended distances allowing repair and regeneration of damaged neural pathways. While neurons of the peripheral nervous system can sprout new processes following injury, without guidance these sproutings typically fail to connect appropriately and die. Where the break is extensive, e.g., greater than 5 or 10 mm, regeneration is poor or nonexistent.

In this example morphogen stimulation of nerve regeneration was assessed using the rat sciatic nerve model. The rat sciatic nerve can regenerate spontaneously across a 5 mm gap, and occasionally across a 10 mm gap, provided that the severed ends are inserted in a saline-filled nerve guidance channel. In this experiment, nerve regeneration across a 12 mm gap was tested.

Adult female Sprague-Dawley rats (Charles River Laboratories, Inc.) weighing 230–250 g were anesthetized with intraperitoneal injections of sodium pentobarbital 35 mg/kg body weight). A skin incision was made parallel and just posterior to the femur. The avascular intermuscular plane between vastus lateralis and hamstring muscles were entered and followed to the loose fibroareolar tissue surrounding the sciatic nerve. The loose tissue was divided longitudinally thereby freeing the sciatic nerve over its full extent without devascularizing any portion. Under a surgical microscope the sciatic nerves were transected with microscissors at mid-thigh and grafted with an OP-1 gel graft that separated the nerve stumps by 12 mm. The graft region was encased in a silicone tube 20 mm in length with a 1.5 mm inner diameter, the interior of which was filled a morphogen solution. Specifically, The central 12 mm of the tube consisted of an OP-1 gel prepared by mixing 1 to 5 $\mu$g of substantially pure CHO-produced recombinant OP-1 with approximately 100 $\mu$l of MATRIGEL (from Collaborative Research, Inc., Bedford, Mass.), an extracellular matrix extract derived from mouse sarcoma tissue, and containing solubilized tissue basement membrane, including laminin, type IV collagen, heparin sulfate, proteoglycan and entactin, in phosphate-buffered saline. The OP-1-filled tube was implanted directly into the defect site, allowing 4 mm on each end to insert the nerve stumps. Each stump was abutted against the OP-1 gel and was secured in the silicone tube by three stitches of commercially available surgical 10-0 nylon through the epineurium, the fascicle protective sheath.

In addition to OP-1 gel grafts, empty silicone tubes, silicone tubes filled with gel only and "reverse" autografts, wherein 12 mm transected segments of the animal's sciatic nerve were rotated 180° prior to suturing, were grafted as controls. All experiments were performed in quadruplicate. All wounds were closed by wound clips that were removed after 10 days. All rats were grafted on both legs. At 3 weeks the animals were sacrificed, and the grafted segments removed and frozen on dry ice immediately. Frozen sections then were cut throughout the graft site, and examined for axonal regeneration by immunofluorescent staining using anti-neurofilament antibodies labeled with flurocein (obtained from Sigma Chemical Co., St. Louis).

Regeneration of the sciatic nerve occurred across the entire 12 mm distance in all graft sites wherein the gap was filled with the OP-1 gel. By contrast, empty silicone tubes and reverse autografts did not show nerve regeneration, and only one graft site containing the gel alone showed axon regeneration.

Example 8

Morphogen-Induced Nerve Gap Repair (CNS)

Following axonal damage in vivo the CNS neurons are unable to resprout processes. Accordingly, trauma to CNS nerve tissue, including the spinal cord, optic nerve and retina, severely damages or destroys the neural pathways defined by these cells. Peripheral nerve grafts have been used in an effort to bypass CNS axonal damage. Successful autologous graft repair to date apparently requires that the graft site occur near the CNS neuronal cell body, and a primary result of CNS axotomy is neuronal cell death. The efficacy of morphogens described herein on CNS nerve repair, can be evaluated using a rat crushed optic nerve model such as the one described by Bignami et al., (1979) *Exp. Eye Res.* 28: 63–69, the disclosure of which is incorporated herein by reference. Briefly, and as described therein, laboratory rats (e.g., from Charles River Laboratories, Wilmington, Mass.) are anesthesized using standard surgical procedures, and the optic nerve crushed by pulling the eye gently out of the orbit, inserting a watchmaker forceps behind the eyeball and squeezing the optic nerve with the forceps for 15 seconds, followed by a 30 second interval and second 15 second squeeze. Rats are sacrificed at different time intervals, e.g., at 48 hours, and at 3, 4, 11, 15 and 18 days after operation. The effect of morphogen on optic nerve repair can be assessed by performing the experiment in duplicate and providing morphogen or PBS (e.g., 25 µl solution, and 25 µg morphogen) to the optic nerve, e.g., just prior to the operation, concommitant with the operation, or at specific times after the operation.

In the absence of therapy, the surgery induces glial scarring of the crushed nerve, as determined by immunofluoresence staining for glial fibrillary acidic protein (GFA), a marker protein for glial scarring, and by histology. Indirect immunofluoresence on air-dried cryostat sections as described in Bignami et al. (1974) *J. Comp. Neur.* 153: 27–38, using commercially available antibodies to GFA (e.g., Sigma Chemical Co., St. Louis). Reduced levels of GFA are anticipated in animals treated with the morphogen, evidencing the ability of morphogens to inhibit glial scar formation and to stimulate optic nerve regeneration.

Example 9

Nerve Tissue Diagnostics

Morphogen localization in nerve tissue can be used as part of a method for diagnosing a neurological disorder or neuropathy. The method can be particularly advantageous for diagnosing neuropathies of brain tissue. Specifically, a biopsy of brain tissue is performed on a patient at risk, using standard procedures known in the medical art. Morphogen expression associated with the biopsied tissue then is assessed using standard methodologies, as by immunolocalization, using standard immunofluorescence techniques in concert with morphogen-specific antisera or monoclonal antibodies. Specifically, the biopsied tissue is thin sectioned using standard methodologies known in the art, and fluorescently labelled (or otherwise detectable) antibodies incubated with the tissue under conditions sufficient to allow specific antigen-antibody complex formation. The presence and quantity of complex formed then is detected and compared with a predetermined standard or reference value. Detection of altered levels of morphogen present in the tissue then can be used as an indicator of tissue dysfunction. Alternatively, fluctuation (increase or decrease) in morphogen levels can be assessed by monitoring morphogen transcription levels, either by standard northern blot analysis or in situ hybridization, using a labelled probe capable of hybridizing specifically to morphogen RNA and standard RNA hybridization protocols well described in the art.

Monitoring fluctuations (increases or decreases) over time in morphogen levels present in the cerebrospinal fluid or bloodstream of an individual also can be used to evaluate nerve tissue viability. For example, morphogens are detected in association with adendema cells which are known to secrete factors into the cerebrospinal fluid, and are localized generally associated with glial cells, and in the extracellular matrix, but not with neuronal cell bodies. Accordingly, the cerebrospinal fluid may be a natural means of morphogen transport. Alternatively, morphogens can be released from dying cells into cerebrospinal fluid. In addition, OP-1 recently has been identified in human blood, which also can be a means of morphogen transport, and/or a repository for the contents of dying cells.

Spinal fluid can be obtained from an individual by a standard lumbar puncture, using standard methodologies known in the medical art. Similarly, serum samples can be obtained by standard venipuncture and serum prepared by centrifugation at 3,000 RPM for ten minutes. The presence of morphogen in the serum or cerebral spinal fluid then can be assessed by standard Western blot (immunoblot), ELISA or RIA procedures. Briefly, for example, with the ELISA, samples can be diluted in an appropriate buffer, such as phosphate-buffered saline, and 50 µl aliquots allowed to absorb to flat bottomed wells in microtitre plates pre-coated with morphogen-specific antibody, and allowed to incubate for 18 hours at 4° C. Plates then can be washed with a standard buffer and incubated with 50 µl aliquots of a second morphogen-specific antibody conjugated with a detecting agent, e.g., biotin, in an appropriate buffer, for 90 minutes at room temperature. Morphogen-antibody complexes then can be detected using standard procedures.

Alternatively, a morphogen-specific affinity column can be created using, for example, morphogen-specific antibodies adsorbed to a column matrix, and passing the fluid sample through the matrix to selectively extract the morphogen of interest. The morphogen then is eluted. A suitable elution buffer can be determined empirically by determining appropriate binding and elution conditions first with a control (e.g., purified, recombinantly-produced morphogen.) Fractions then are tested for the presence of the morphogen by standard immunoblot, and confirmed by N-terminal sequencing. Morphogen concentrations in serum or other fluid samples then can be determined using standard portein quantification techniques, including by spectrophotometric absorbance or by quantitation by ELISA or RIA antibody assays. Using this procedure, OP-1 has been identified in serum.

Figure 4:
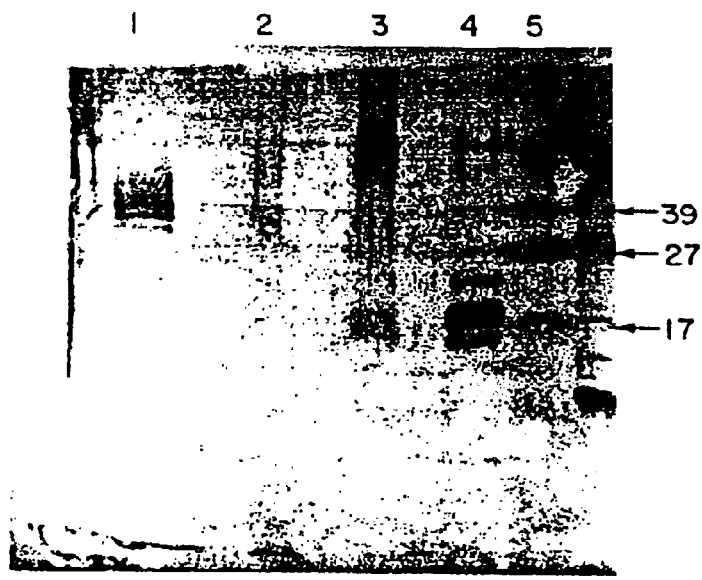
FIG. 4 is a photograph of an immunoblot demonstrating the presence of OP-1 in human serum.

OP-1 was detected in human serum using the following assay. A monoclonal antibody raised against mammalian, recombinantly produced OP-1 using standard immunology techniques well described in the art and described generally in Example 13, was immobilized by passing the antibody over an activated agarose gel (e.g., Affi-Gel™, from Bio-Rad Laboratories, Richmond, Calif., prepared following manufacturer's instructions), and used to purify OP-1 from serum. Human serum then was passed over the column and eluted with 3M K-thiocyanate. K-thiocyanante fractions then were dialyzed in 6M urea, 20 mM $PO_4$, pH 7.0, applied to a C8 HPLC column, and eluted with a 20 minute, 25–50% acetonitrile/0.1% TFA gradient. Mature, recombinantly produced OP-1 homodimers elute between 20–2.2 minutes. Fractions then were collected and tested for the presence of OP-1 by standard immunoblot. FIG. 4 is an immunoblot showing OP-1 in human sera under reducing and oxidized conditions. In the figure, lanes 1 and 4 are OP-1 standards, run under oxidized (lane 1) and reduced (lane 4) conditions. Lane 5 shows molecular weight markers at 17, 27 and 39 kDa. Lanes 2 and 3 are human sera OP-1, run under oxidized (lane 2) and reduced (lane 3) conditions.

Morphogens can be used in diagnostic applications by comparing the quantity of morphogen present in a body fluid sample with a predetermined reference value, with fluctuations in fluid morphogen levels indicating a change in the status of nerve tissue. Alternatively, fluctuations in the level of endogenous morphogen antibodies can be detected by this method, most likely in serum, using an antibody or other binding protein capable of interacting specifically with the endogenous morphogen antibody. Detected fluctuations in the levels of the endogenous antibody can be used as indicators of a change in tissue status.

Example 10

Alleviation of Immune Response-Mediated Nerve Tissue Damage

The morphogens described herein can be used to alleviate immunologically-related damage to nerve tissue. Details of this damage and the use of morphogens to alleviate this injury are disclosed in international application US92/07358 (WO93/04692). A primary source of such damage to nerve tissue follows hypoxia or ischemia-reperfusion of a blood supply to a neural pathway, such as can result from an embolic stroke, or can be induced during a surgical procedure. As described in international application US92/07358 (WO93/04692), morphogens have been shown to alleviate damage to myocardial tissue following ischemia-reperfusion of the blood supply to the tissue. The effect of morphogens on alleviating immunologically-related damage to nerve tissue can be assessed using methodologies and models known to those skilled in the art and described below.

For example, the rabbit embolic stroke model provides a useful method for assessing the effect of morphogens on tissue injury following cerebral ischemia-reperfusion. The protocol disclosed below is essentially that of Phillips et al. (1989) *Annals of Neurology* 25: 281–285, the disclosure of which is herein incorporated by reference. Briefly, white New England rabbits (2–3 kg) are anesthetized and placed on a respirator. The intracranial circulation then is selectively catheterized by the Seldinger technique. Baseline cerebral angiography then is performed, employing a digital substraction unit. The distal internal carotid artery or its branches then is selectively embolized with 0.035 ml of 18-hour-aged autologous thrombus. Arterial occlusion is documented by repeat angiography immediately after embolization. After a time sufficient to induce cerebral infarcts (15 minutes or 90 minutes), reperfusion is induced by administering a bolus of a reperfusion agent such as the TPA analogue FB-FB-cF (e.g., 0.8 mg/kg over 2 minutes).

The effect of morphogen on cerebral infarcts can be assessed by administering varying concentrations of morphogens, e.g., OP-1, at different times before or following embolization and/or reperfusion. The rabbits are sacrificed 3–14 days post embolization and their brains prepared for neuropathological examination by fixing by immersion in 10% neutral buffered formation for at least 2 weeks. The brains then are sectioned in a coronal plane at 2–3 mm intervals, numbered and submitted for standard histological processing in paraffin, and the degree of nerve tissue necrosis determined visually. Morphogen-treated animals are anticipated to reduce or significantly inhibit nerve tissue necrosis following cerebral ischemia-reperfusion in the test animals as determined by histology comparison with non-treated animals.

Example 11

Animal Model for Assessing Morphogen Efficacy
In Vivo

The in vivo activities of the morphogens described herein also are assessed readily in an animal model as described herein. A suitable animal, preferably exhibiting nerve tissue damage, for example, genetically or environmentally induced, is injected intracerebrally with an effective amount of a morphogen in a suitable therapeutic formulation, such as phosphate-buffered saline, pH 7. The morphogen preferably is injected within the area of the affected neurons. The affected tissue is excised at a subsequent time point and the tissue evaluated morphologically and/or by evaluation of an appropriate biochemical marker (e.g., by morphogen or N-CAM localization; or by measuring the dose-dependent effect on a biochemical marker for CNS neurotrophic activity or for CNS tissue damage, using for example, glial fibrillary acidic protein as the marker. The dosage and incubation time will vary with the animal to be tested. Suitable dosage ranges for different species can be determined by comparison with established animal models. Presented below is an exemplary protocol for a rat brain stab model.

Briefly, male Long Evans rats, obtained from standard commercial sources, are anesthesized and the head area prepared for surgery. The calvariae is exposed using standard surgical procedures and a hole drilled toward the center of each lobe using a 0.035K wire, just piercing the calvariae. 25 μl solutions containing either morphogen (e.g., OP-1, 25 μg) or PBS then is provided to each of the holes by Hamilton syringe. Solutions are delivered to a depth approximately 3 mm below the surface, into the underlying cortex, corpus callosum and hippocampus. The skin then is sutured and the animal allowed to recover.

Three days post surgery, rats are sacrificed by decapitation and their brains processed for sectioning. Scar tissue formation is evaluated by immunofluoresence staining for glial fibrillary acidic protein, a marker protein for glial scarring, to qualitatively determine the degree of scar formation. Glial fibrillary acidic protein antibodies are available commercially, e.g., from Sigma Chemical Co., St. Louis, Mo. Sections also are probed with anti-OP-1 antibodies to determine the presence of OP-1. Reduced levels of glial fibrillary acidic protein are anticipated in the tissue sections of animals treated with the morphogen, evidencing the ability of morphogens to inhibit glial scar formation and stimulate nerve regeneration.

Example 12

In Vitro Model for Evaluating Morphogen
Transport Across the Blood-Brain Barrier Described below is an in vitro method for evaluating the facility with which a selected morphogen likely will pass across the blood-brain barrier. A detailed description of the model and protocol are provided by Audus et al. (1987) *Ann. N.Y. Acad. Sci.* 507: 9–18, the disclosure of which is incorporated herein by reference.

Briefly, microvessel endothelial cells are isolated from the cerebral gray matter of fresh bovine brains. Brains are obtained from a local slaughter house and transported to the laboratory in ice cold minimum essential medium (MEM) with antibiotics. Under sterile conditions the large surface blood vessels and meninges are removed using standard dissection procedures. The cortical gray matter is removed by aspiration, then minced into cubes of about 1 mm. The minced gray matter then is incubated with 0.5% dispase (BMB, Indianapolis, Ind.) for 3 hours at 37° C. in a shaking water bath. Following the 3 hour digestion, the mixture is concentrated by centrifugation (1000×g for 10 min.), then resuspended in 13% dextran and centrifuged for 10 min. at 5800×g. Supernatant fat, cell debris and myelin are discarded and the crude microvessel pellet resuspended in 1 mg/ml collagenase/dispase and incubated in a shaking water bath for 5 hours at 37° C. After the 5-hour digestion, the microvessel suspension is applied to a pre-established 50% Percoll gradient and centrifuged for 10 min at 1000×g. The band containing purified endothelial cells (second band from the top of the gradient) is removed and washed two times with culture medium (e.g., 50% MEM/50% F-12 nutrient mix). The cells are frozen (−80° C.) in medium containing 20% DMSO and 10% horse serum for later use.

After isolation, approximately $5 \times 10^5$ cells/cm$^2$ are plated on culture dishes or 5–12 mμ pore size polycarbonate filters that are coated with rat collagen and fibronectin. 10–12 days after seeding the cells, cell monolayers are inspected for confluency by microscopy.

Characterization of the morphological, histochemical and biochemical properties of these cells has shown that these cells possess many of the salient features of the blood-brain barrier. These features include: tight intercellular junctions, lack of membrane fenestrations, low levels of pinocytotic activity, and the presence of gamma-glutamyl transpeptidase, alkaline phosphatase, and Factor VIII antigen activities.

The cultured cells can be used in a wide variety of experiments where a model for polarized binding or transport is required. By plating the cells in multi-well plates, receptor and non-receptor binding of both large and small molecules can be conducted. In order to conduct transendothelial cell flux measurements, the cells are grown on porous polycarbonate membrane filters (e.g., from Nucleopore, Pleasanton, Calif.). Large pore size filters (5–12 m$\mu$) are used to avoid the possibility of the filter becoming the rate-limiting barrier to molecular flux. The use of these large-pore filters does not permit cell growth under the filter and allows visual inspection of the cell monolayer.

Once the cells reach confluency, they are placed in a side-by-side diffusion cell apparatus (e.g., from Crown Glass, Sommerville, N.J.). For flux measurements, the donor chamber of the diffusion cell is pulsed with a test substance, then at various times following the pulse, an aliquot is removed from the receiver chamber for analysis. Radioactive or fluorescently-labelled substances permit reliable quantitation of molecular flux. Monolayer integrity is simultaneously measured by the addition of a non-transportable test substance such as sucrose or inulin and replicates of at least 4 determinations are measured in order to ensure statistical significance.

Example 13

OP-1 Induces Dendritic Growth in Sympathetic Neurons

Suspensions of neurons dissociated from the superior cervical ganglia of Sprague-Dawley rat fetuses (19–21 day) or rat pups (1–3 day postnatal) were prepared according to the method of (Higgins et al. (1991), *Culturing Nerve Cells* Banker and Goslin, eds., MIT Press, pp. 177–205, the teachings of which herein incorporated by reference). Equivalent results were obtained with pre- and postnatal animals. Neurons were plated at low density (about 10 cells/mm$^2$) onto poly-D-lysine coated (100 $\mu$g/ml) coverslips and maintained in a serum-free medium (Higgins et al. (1991), *Culturing Nerve Cells*) containing NGF (100ng/ml Cytosine-$\beta$-D-furanoside (1 $\mu$M) was added to the medium of all cultures for 48 hrs on the second day. This exposure was sufficient to render them virtually free of nonneuronal cells for 30 days. To label sympathetic neuroblasts, ganglia from 15-day embryos were grown in explant culture for 18 hrs in the presence of $^3$H-(methyl)-thymidine (0.3 $\mu$Ci/ml, ICN) before being dissociated. Because NT3 (50 ng/ml) enhances the survival of immature sympathetic neurons (Birren et al. (1993), 119 *Develop* 597–610), it was added to the NGF-containing medium during the period of explant culture and the next 4 days in vitro. As in cultures of sympathetic neurons, exposure to NGF, OP-1 or both was initiated after the elimination of nonneuronal cells.

Cellular morphology was routinely assessed by intracellular injection of fluorescent dyes (4% Lucifer Yellow or 5% 5, 6 dicarboxyfluorescein)(Bruckenstein and Higgins (1988), 128 *Dev. Biol.* 924–936). Only neurons whose cell bodies were at least 150 $\mu$m from their nearest neighbor were injected because density-dependent changes in morphology occur when somata of sympathetic neurons are separated by lesser distances. Mature human recombinant OP-1 was isolated from medium conditioned by transfected Chinese hamster ovary cells using S-Sepharose and phenyl-Sepharose chromatography followed by reverse phase high performance liquid chromatography as described previously.

Under control conditions, sympathetic neurons typically extended a single process during the first 24–48 hrs in vitro. This process has the cytoskeletal and ultrastructural characteristics of an axon. The axon continued to elongate during the next few weeks and generate an elaborate plexus. The basic morphology of the cells, however, remained essentially unchanged, with 80% of the neurons still being unipolar after 1 month in vitro. Most of the remainder had either 2 axons (13% of the cells) or an axon and a short dendrite (7%). Thus, the mean number of processes at this time was 1.13±0.06 axons/cells and 0.07±0.04 dendrites/cell.

Exposure to OP-1 caused sympathetic neurons to form additional processes. This response was relatively slow with only 42% of the cells forming a second process within 24 hrs. However, virtually all cells (94%) had begun to respond to maximally effective concentrations of OP-1 within 3 days. The processes that formed in the presence of OP-1 had the appearance of dendrites in that they were broad-based (up to 5 $\mu$m diameter), exhibited a distinct taper, and branched in a "Y"-shaped pattern, with daughter processes being distinctly smaller than the parent process. Dendrites were much thicker than sympathetic axons and, unlike axons, they ended locally, usually extending less than 300 $\mu$m from the soma. The mean number of dendrites/cell continued to increase during a 4 week exposure to OP-1 with most of the change occurring during the first 10 days of treatment. After 4 weeks, OP-1-treated neurons had a mean of 7.3±0.3 dendrites/cell, representing a 100-fold increase over control cells. During this time, the size of the dendritic arbor also increased with cells progressing from simple cells to a more complicated morphology. These observations are summarized in panels A, B and C of FIG. 5.

TABLE III

COMPARISON OF THE DENDRITIC ARBORS GENERATED BY SYMPATHETIC NEURONS IN SITU AND AFTER A 2 WEEK EXPOSURE TO OP-1.

| PARAMETER | IN SITU* | IN VITRO |
|---|---|---|
| Number of dendrites/cells | 6.9 ± 2.1 | 7.6 ± 0.4 |
| Total linear length of dendritic arbor ($\mu$m) | 779 ± 288 | 1078 ± 77 |
| Maximum extent of arbor ($\mu$m) | 99 ± 31 | 171 ± 6 |
| Number of branches crossing 50% circle | 8.0 ± 2.8 | 9.3 ± 0.7 |
| Soma diameter ($\mu$m) | 29.2 ± 6.0 | 32.9 ± 0.5 |

*in situ data are from Snider (1988) 8 J. Neurosci. 2628-2634. Mean ± SD.
After a 2 week exposure to OP-1, cultures of sympathetic neurons from 2 different dissections were immunostained with dendrite-specific antibody (SMI-32 or AP14)(Lein and Higgins (1989), 136 Dev. Biol. 330–345). Dendritic growth was quantitated using the Image 1 Software image analysis system (Lein and Higgins (1989), 136 Dev. Biol. 330–345). The dendritic extent is the radius of a circle encompassing the entire arbor. The number of branches crossing a circle of half that diameter was used as an index of branching (Scholl (1953), 87 J. Anat. (London) 387, the teachings of which are herein incorporated by reference). Data are expressed as the mean ± SEM (N = 40).

Figure 5A:
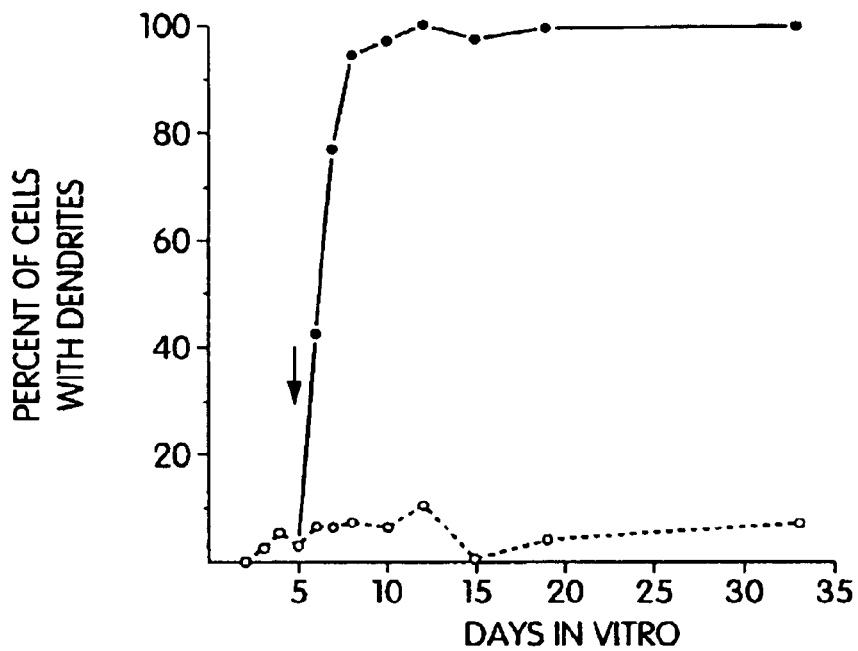
FIG. 5A is a line plot time course of the response of cultured sympathetic neurons to OP-1. Intracellular dye injections (N>30 for each time point) were performed at various times to determine the percentage of cells with dendrites (open symbols, control; closed symbols, cell supplemented with 100 ng/ml OP-1 during the time course study).
Figure 5B:
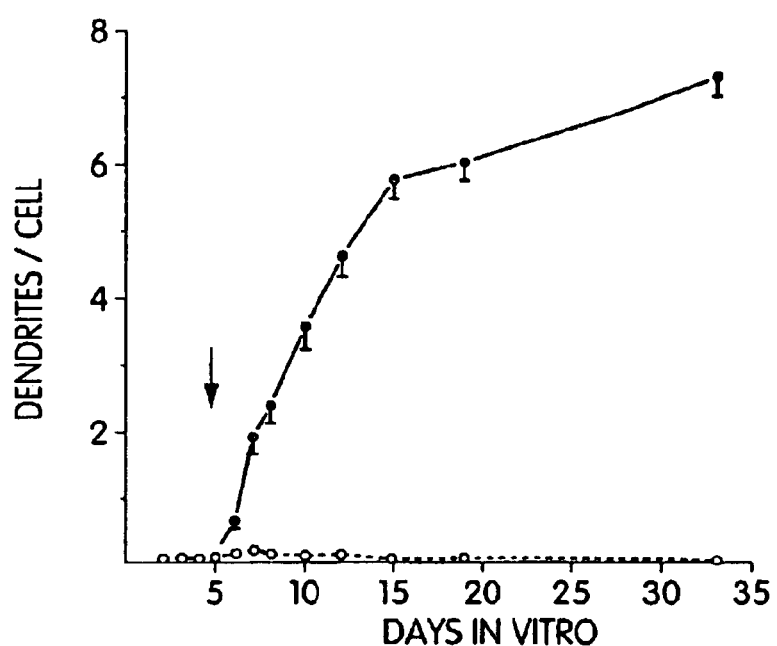
FIG. 5B is a line plot time course carried out as described for FIG. 5A and depicting the mean number of dendrites per cell. The bars shown represent the SEM; where bars are not shown, the SEM was smaller than the size of the symbol.
Figure 5C:
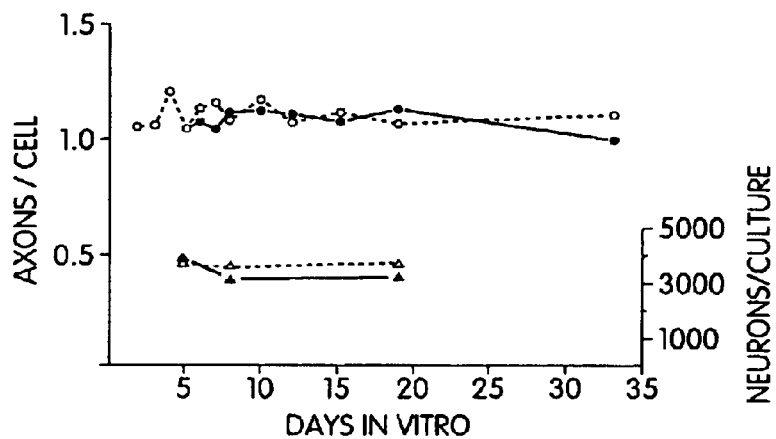
FIG. 5C is a line plot time course carried out as described for FIG. 5A and depicting the number of axons per cell (circles).

The effects of OP-1 appeared to be dendrite-specific since there was no increase in axon number when tested in the delayed introduction paradigm used in the experiment shown in FIG. 5. The effects of OP-1 on initial axon growth during the first 48 hrs. in culture were also examined. It did not affect either the rate at which axons were initially extended or the number of axons extended per cell. Cell number also remained constant during the exposure to OP-1, indicating that it was not acting by enhancing the survival of a subpopulation of neurons as shown in FIG. 5.

Example 14

Properties of Dendrites Formed in the Presence of OP-1

Other techniques were used to confirm the light microscopic identification of processes and to access the state of differentiation of the dendrites formed in the presence of OP-1. For example, cultures were immunostained with antibodies previously shown to react selectively with either axons or dendrites (Lein and Higgins (1989), 136 *Dev. Biol.* 330–345). Monoclonal (mAb) antibodies to MAP2 (AP14, a gift of L. I. Binder), to nonphosphorylated forms of the M and H neurofilaments (SMI32, Sternbery-Meyer Immunocytochemicals), and to the transferrin receptor (MRC OX-26, Serotech) were used as dendritic markers. The teachings of each of the above-mentioned publications are incorporated herein by reference. Axonal probes included mAb's to synaptophysin (SY-38, Boehringer Mannheim), tau (Tau 1, L. I. Binder), and phosphorylated forms of the H (NE14, Boehringer Mannheim) and the M and H (SMI31, Sternbery-Meyer Immunocytochemicals) neurofilament subunits. All antigens were localized by indirect immunofluoresence using previously described procedures (Lein and Higgins (1989), 136 *Dev. Biol.* 330–345). Image 1 Software (Universal Imaging) was used for the morphometric analyses of dendritic growth in immunostained cultures.

When cultures exposed to OP-1 were immunostained with a MAb to MAP2, immunoreactivity was observed in the somata and the dendritic processes, but not in the thinner axons. Moreover, the mean number and average length of the MAP2-positive processes corresponded closely (within 10%) to the values obtained from dye injections suggesting that all dendrites were stained in their entirety. A similar staining pattern was observed with mAbs to non-phosphorylated neurofilaments and to the transferrin receptor. In contrast, monoclonal antibodies to tau, synaptophysin, or phosphorylated forms of the H or the M and H neurofilament subunits selectively stained the thin axons, with little or no immunoreactivity being observed in the dendrites. Additional features ascertained by immunostaining are summarized in Table III.

Example 15

Concentration Effect of OP-1

Figure 6:
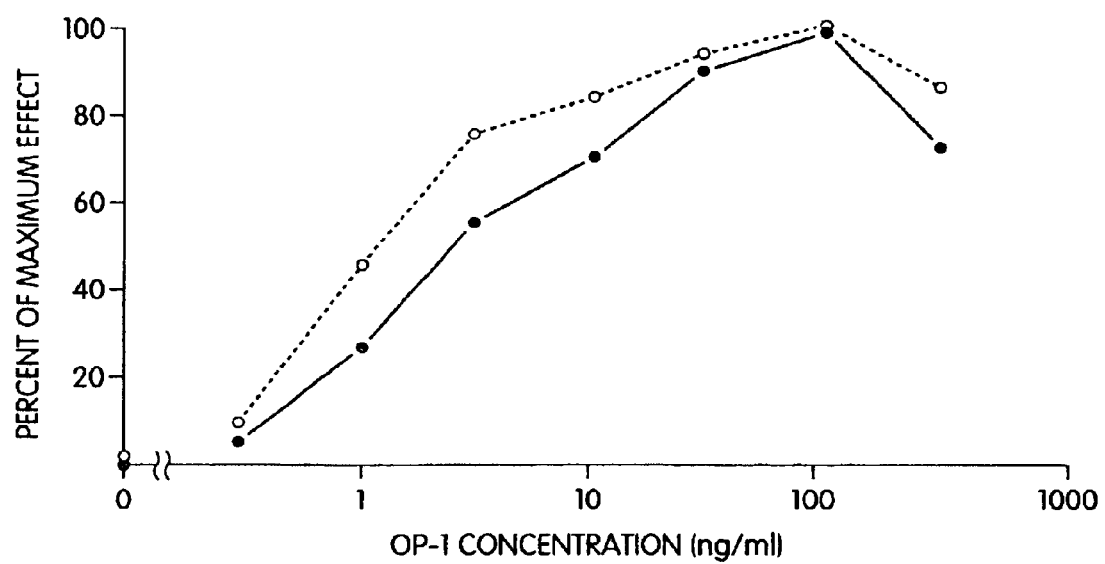
FIG. 6 is a line graph plot of the effects of varying concentrations of OP-1 on dendritic growth. Sympathetic neurons were exposed to OP-1 in culture for 3 days and then immunostained with a dendrite-specific mAb (SMI 32). Percentage of cells with dendrites, open circles; mean number of dendrites per cell, filled circles.

The effects of OP-1 were concentration-dependent (FIG. 6). Significant changes in dendritic growth could be detected with concentrations as low as 300 pg/ml and half-maximal effects were observed at about 2 ng/ml. Maximal dendritic growth was obtained with medial concentrations between 30 and 100 ng/ml.

Although typically added to the medium on day 5, earlier initiation of dendritic growth (by the third day of culture) could be obtained by adding OP-1 to the medium at the time of plating. No dendritic growth was detected in cultures in which the OP-1 (1 µg/ml) had been allowed to absorb to coverslips before plating cells.

It appeared that several parameters of dendritic growth, including the percentage of cells with dendrites, the mean number of dendrites/cell, dendritic length (not shown), changed over the same concentration range (FIG. 6). In addition, three other changes in cellular morphology in this concentration range were observed. As had been observed while dendritic growth is occurring in vivo, the somata became larger. In addition, the nuclei became less eccentric and the axons formed small fascicles.

Example 16

Comparison of OP-1 to Other Growth Factors

Mature human recombinant Op-1 was isolated from medium conditioned by transfected Chinese hamster ovary cells using S-Sepharose and phenyl-Sepharose chromatography followed by reverse phase high performance liquid chromatography as described above. Ciliary neurotrophic factor (CNTF) was purified from rat sciatic nerve (Manthorpe et al. (1986) 367 *Brain Research* 282–286, the teachings of which are herein incorporated by reference) and activin A was generously provided by Ralph Schwall (Genentech). Other growth factors were obtained from commercial sources: GIBCOBRL (IL-1β,3,4,6,7; LIF, EGF, GM-CSF, RANTES, MCAF, TGFα, TGFβ1 and 3, rat gamma interferon); Collaborative Research (HGF, PDGF); Boehringer (IL 2); and Promega (IL 8).

Since OP-1 is a member of the TGFβ superfamily, its actions were compared to those of the growth factors (Table IV). Dendritic growth was not observed in the presence of TGFβ1, TGFβ3, activin A or inhibin, all of which are members of the TGFβ family but are not members of the structurally distinct sub-family thereof to which the morphogens belong. In addition, negative results were obtained with most neurotrophins and nine other growth factors known to affect neuronal survival or differentiation. In other experiments, negative results were also obtained with: TGFβ2, interleukins 1β,2,3,4,6,7,8, PDGF, HGF, GM-CSF, MCAF, RANTES, TGFα and gamma interferon. It would thus appear that the dendrite-promoting effect of OP-1 is a highly specific response that is observed with a very limited subset of growth factors. It is believed that the OP-1 effect will be reproduced or approximated by other morphogens.

TABLE IV

COMPARISON OF THE EFFECTS OF OP-1 AND OTHER GROWTH FACTORS ON DENDRITIC GROWTH

| GROWTH FACTOR | MEAN NUMBER OF DENDRITES/CELL |
| --- | --- |
| NONE | 0.8 ± 0.04 |
| OP1 | 3.08 ± 0.20 |
| TGFβ1 | 0.17 ± 0.09 |
| TGFβ3 | 0.00 ± 0.00 |
| INHIBIN | 0.20 ± 0.10 |
| ACTIVIN A | 0.08 ± 0.05 |
| BDNF | 0.11 ± 0.05 |
| NT3 | 0.11 ± 0.07 |
| NT4 | 0.32 ± 0.11 |
| CNTF | 0.10 ± 0.05 |
| LIF | 0.13 ± 0.07 |
| EGF | 0.07 ± 0.07 |
| bFGF | 0.03 ± 0.03 |

Beginning on day 5, cultures of sympathetic neurons were exposed to varying concentrations of growth factors. Seven to eight days later, the mean number of dendrites/cell was assessed by intracellular dye injection (N > 30 cells for each condition). Only the results obtained with the highest concentration tested (100 ng/wl) are shown in this table, but lower concentrations yielded similar results.

Example 17

NGF and the Response to OP-1

Figure 7:
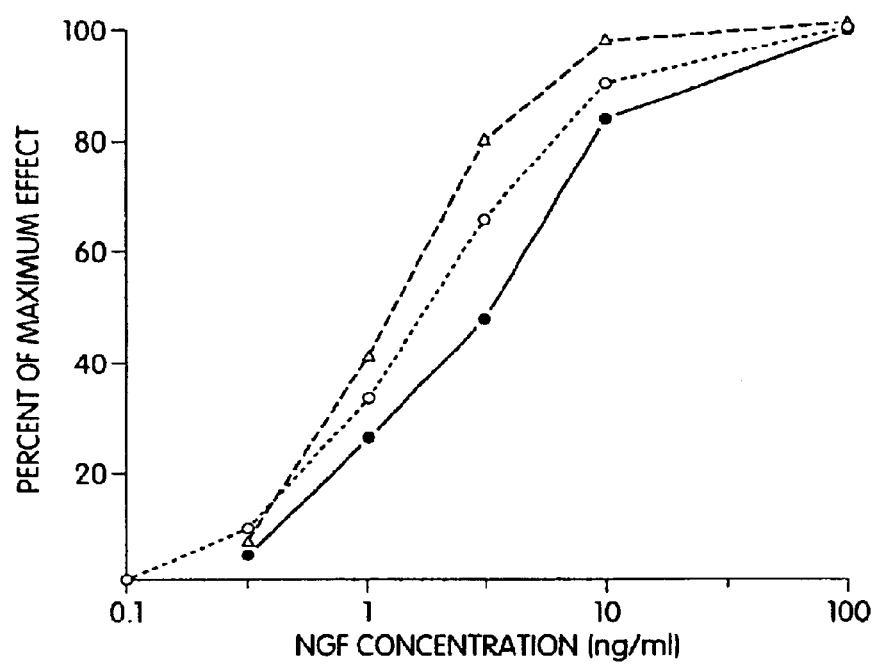
FIG. 7 is a line graph plot of the effects of varying concentrations of NGF on OP-1 induced dendritic growth in cultured sympathetic neurons. Percentage of cells with dendrites (97%, open triangles); mean number of dendrites/cell (4.7±0.3, solid circles); neurons surviving/culture (2808±267, open circles).

Since NGF regulates the growth of sympathetic dendrites in situ, the possibility that it might exert a similar action in vitro was investigated. For this study, murine NGF was purified from mouse salivary glands according to standard protocols. Recombinant NGF also could have been used. Since dendritic growth was not observed in the control medial which contained high levels of NGF, it seemed reasonable that NGF might function as a modulator rather than an inducer of dendritic growth. Neurons were, therefore, exposed to a maximally effective concentration of OP-1 while the concentration of NGF was varied. As the concentration of NGF was decreased from 100 ng/ml to 0.3 ng/ml (FIG. 7), there was a dose dependent decrease in the mean number of dendrites/cell, the percentage of cells with dendrites, and the length of the longest dendrite. Cell number decreased over this same concentration range and the half-maximal concentration for cell survival differed less than 2-fold from that for either the percentage of cells with dendrites or the mean number of dendrites. These data suggest NGF is a necessary cofactor for OP-1 induced dendritic growth and that the amount of dendritic growth that occurs is highly dependent on the trophic state of the cell.

Example 18

OP-1 and Neuronal Survival

A separate study investigated the effects of OP-1 on neuronal survival in the primary culture system described in Example 13 above. After 48 hrs, the number of neurons in OP-1 treated cultures was less than 3% of that in NGF-treated cultures and by 72 hrs all neurons in the OP-1 cultures had died. Thus, the effects of OP-1 are distinct from those NGF. In particular, NGF was significantly more effective in promoting survival of primary symphathetic neurons in culture.

Example 19

Comparison of Dendritic Growth In Vitro and In Situ

To assess the potential importance of OP-1 as a regulatory molecule, the extent of dendritic growth that occurs in vitro was compared to that which normally occurs during a comparable period in situ (Table III). For the former, cultures were used that had been exposed to optimal concentrations of OP-1 and NGF for 2 weeks (and then immunostained with a dendrite-specific mAb). For the latter, published in situ data (Snider (1988), 8 *J. Neurosci,* 2628–2634) was used that relates particularly to the dendrites of superior cervical ganglion neurons of 2-week postnatal rats. This published in situ data was generated as follows: NGF was administered daily to newborn Sprague-Dawley rats beginning on postnatal day 1 or 2. Purified β subunit of mouse NGF (kindly provided by E. M. Johnson, Jr. and P. Osborne) was dissolved in saline and injected subcutaneously in a dosage of 5 mg/kg. A similar dose is known to increase sympathetic ganglion cell size and enhance synthesis of transmitter enzymes (Thoenen et al. (1971), 68 *Proc. Natl. Acad. Sci. USA* 1598–1602). Animals were treated for either 17 or 14 d and compared with controls at these same ages.

For intracellular staining, the superior cervical ganglia were removed and pinned in a chamber superfused with an oxygenated mammalian saline. Neurons were impaled with triangular glass electrodes (Glass Co. of America) filled with a 4% solution of HRP (Sigma, type 6). The HRP was introduced into the cell by iontophoresis and the reaction product was visualized by the pyrocathecol-phenylenediamine method (Hanker et al. (1977), 9 *Histochem. J.* 789–792; for details see Purves and Hume (1981), 1 *J. Neurosci.* 441–452; Forehand and Purves (1984), 4 *J. Neurosci.* 1–12). Stained neurons were viewed at 300× in whole-mount preparations and traced with the aid of a camera lucida. Dendritic and axonal processes were distinguished using established criteria (Purves and Hume (1981), 1 *J. Neurosci.* 441–452). Dendrites had numerous short processes arising from the main shaft and branched into secondary and tertiary segments relatively close to the cell soma. The axon was readily identified as a smooth, thick process that usually could be followed for at least several hundred microns and frequently could be seen exiting the ganglion via a postganglionic nerve. In control ganglia neurons invariably possessed a single axon, whereas a few cells in the NGF groups had 2. Also in the NGF group, axons frequently elaborated branches within the ganglion, a feature not seen in controls. Occasional processes in treated animals could not be clearly categorized and were not included in the quantitative analysis. The arbor of each neuron was assessed by 4 measures of dendritic complexity. The number of primary dendrites was determined by viewing the cells at 480× in multiple focal planes. A primary dendrite was defined as any process extending from the soma a distance greater than one cell diameter. Total dendritic lengths were measured from the camera lucida tracings with the aid of a digitizing tablet and a general purpose program for neural imaging (Voyvodic (1986), 12 *Soc. Neurosci. Abstr.* 390). The radius of a circle incorporating the entire arbor was measured as an indicator of the process length. Finally, the extent-of branching was determined by counting the number of branches crossing a 50% circle (Scholl (1953), 244 *J. Comp. Neurol.* 245–253).

All well-stained neurons were analyzed. At 1 week, 47 neurons from 6 ganglia in NGF-treated animals were compared with 39 neurons in 10 ganglia from controls. Morphologic data on some cells in the 1 week control group are from a previous study (Snider, 1986). At 2 weeks, 43 cells in 6 ganglia from NGF-treated animals were compared with 36 cells in 8 ganglia from controls.

Cells exposed to OP-1 in vitro were at least as complex as their counterparts in situ. They had about the same number of dendrites as cells in situ but the length of their dendritic arbor was 38% greater. In addition, the maximum extent of the arbor and complexity of the branching pattern were increased in vitro. Since these experiments were performed in a chemically defined medium, it appears that the combination OP-1 and NGF presents a sufficient condition for establishment of a normal dendritic arbor.

Example 20

Screening Assay for Candidate Compounds which Alter Endogenous Morphogen and Nerve Trophic Factor Levels The following screening assay can be used to establish whether candidate compound(s) can affect the production (gene expression and/or protein secretion) of a given morphogen by cells competent to produce said morphogen. Cells that are competent to produce a desired morphogen include, within their genetic material, a gene encoding the desired morphogen. This morphogen gene is preferably a cellular gene naturally present in the cells, but can also be a foreign gene introduced by standard genetic engineering techniques. The morphogen gene is in operative association with nucleic acid expression regulatory elements thereof, including but not necessarily limited to a promoter element. Thus, such cells, although not necessarily actively expressing the morphogen gene, are competent to express this gene when appropriately stimulated by a candidate morphogen stimulating agent. The desired morphogen can be a known morphogen (e.g., OP1, OP2 or other protein listed in Table II or otherwise described herein) or a new, previously unidentified morphogen. In the following screening assay, the level of morphogen production by competent cells which can produce measurable levels of the morphogen is determined with and without incubating the cell in culture with the compound, in order to assess the effects of the compound on the cell. This can be accomplished by detection of the morphogen either at the protein or RNA level. Classes of candidate compounds that can be tested for morphogen stimulating activity include but are not limited to biological response modifiers (lymphokines, cytokines, hormones, vitamins, neurotransmitters, chemotrophic factors, chemoattractants and other cell products), plant extracts and/or phytochemicals, microbial products, including fungal and bacterial products, body fluids, tissue or organ extracts, and broth or medium conditioned by living cells of prokaryotic or eukaryotic origin. Other classes of compounds that can be assessed for morphgen-stimulating activity include naturally sourced or synthetic compounds with known or suspected pharmacologic activity. Thus, for example, Ishibashi et al. (1993), 193 *Biochem. Biophys. Res. Comm.* 235–239 (the disclosure of which is hereby incorporated by reference), teaches that naturally sourced and synthetic modulators of protein kinase A and protein kinase C expression and/or activity can affect the expression of OP1 (referred to in the reference as BMP-7). The specific modulators tested in Ishibashi et al. included Forskolin, 8-bromo-cyclic AMP and phorbolmyristyl acetate (PMA). A more detailed description of the screening assay also can be found in international application US92/07359 (WO92/05172), the teachings of which are incorporated herein by reference.

20.1 Growth of Cells in Culture

Primary or immortalized cultures of cells of kidney, adrenal glands, bladder, brain, or other tissue specific origin can be prepared as described widely in the literature. For example, kidneys can be explanted from neonatal or new born or young or adult rodents (mouse or rat) and used in organ culture as whole or sliced (1–4 mm) tissues. Primary tissue cultures and established cell lines, also derived from kidney, adrenals, urinary, bladder, brain, mammary, or other tissues can be established in multiwell plates (6 well or 24 well) according to conventional cell culture techniques, and are cultured in the absence or presence of serum for a period of time (1–7 days). Cells can be cultured, for example, in Dulbecco's Modified Eagle medium (Gibco, Long Island, N.Y.) containing serum (e.g., fetal calf serum at 1%–10%, Gibco) or in serum-deprived medium, as desired, or in defined medium (e.g., containing insulin, transferrin, glucose, albumin, or other growth factors).

Samples for testing the level of morphogen production include culture supernatants or cell lysates, collected periodically prior to and following exposure to one or more concentrations of a known or candidate morphogen-stimulating agent, and evaluated for morphogen production by immunoblot analysis with an appropriate specific antibody or fragment thereof. (Sambrook et al., eds., 1989, Molecular Cloning, Cold Spring Harbor Press, Cold Spring Harbor, N.Y.). Alternatively, samples can be used to prepare polyA+ RNA for RNA analysis with an appropriate morphogen specific probe. To monitor de novo morphogen synthesis, some cultures are labeled according to conventional procedures with an $^{3\ 5}$S-methionine/$^{3\ 5}$ S-cysteine mixture for 6–24 hours and then evaluated to OP-1synthesis by conventional immunoprecipitation methods. Optionally, samples can be assayed for morphogenic activity using a suitable bioassay therefor, (e.g., an in vitro bioassay for indicia of tissue-specific morphogenesis. Such as bioassay system can be particularly suitable for investigating expression of novel or previously uncharacterized morphogens.

20.2 Determination of Level of Morphogenic Protein

In order to quantitate the production of a morphogenic protein by a cell type, an immunoassay can be performed to detect the morphogen using a polyclonal or monoclonal antibody specific for that protein. For example, OP-1 can be detected using a polyclonal antibody specific for OP-1 in an ELISA, as follows.

1 $\mu$g/100 $\mu$l of affinity-purified polyclonal rabbit IgG specific for OP-1 is added to each well of a 96-well plate and incubated at 37° C. for an hour. The wells are washed four times with 0.167M sodium borate buffer with 0.15 M NaCl (BSB), pH 8.2, containing 0.1% Tween 20. To minimize non-specific binding, the wells are blocked by filling completely with 1% bovine serum albumin (BSA) in BSB and incubating for 1 hour at 37° C. The wells are then washed four times with BSB containing 0.1% Tween 20. A 100 $\mu$l aliquot of an appropriate dilution of each of the test samples of cell culture supernatant is added to each well in triplicate and incubated at 37° C. for 30 min. After incubation, 100 $\mu$l biotinylated rabbit anti-OP-1 serum (stock solution is about 1 mg/ml and diluted 1:400 in BSB containing 1% BSA before use) is added to each well and incubated at 37° C. for 30 ml. The wells are then washed four times with BSB containing 0.1% Tween 20. 100 $\mu$l strepavidin-alkaline (Southern Biotechnology Associates, Inc. Birmingham, Ala., diluted 1:2000 in BSB containing 0.1% Tween 20 before use) is added to each well and incubated at 37° C. for 30 min. The plates are washed four times with 0.5M Tris buffered Saline (TBS), pH 7.2. 50 $\mu$l substrate (ELISA Amplification System Kit, Life Technologies, Inc., Bethesda, Md.) is added to each well incubated at room temperature for 15 min. Then, 50 $\mu$l amplifier (from the same amplification system kit) is added and incubated for another 15 min at room temperature. The reaction is stopped by the addition of 50 $\mu$l 0.3 M sulphuric acid. The OD at 490 nm of the solution in each well is recorded. To quantitate OP-1 in culture media, a OP-1 standard curve is performed in parallel with the test samples.

Polyclonal antibody can be prepared as follows. Each rabbit is given a primary immunization of 100 $\mu$g/500 $\mu$l *E. coli* produced OP-1 monomer (amino acids 328–431 in SEQ ID NO:5) in 0.1% SDS mixed with 500 $\mu$l Complete Freund's Adjuvant. The antigen is injected subcutaneously at multiple sites on the back and flanks of the animal. The rabbit is boosted after a month in the same manner using incomplete Freund's Adjuvant. Test bleeds are taken from the ear vein seven days later. Two additional boosts and test bleeds are performed at monthly intervals until antibody against OP-1 is detected in the serum using an ELISA assay. Then, the rabbit is boosted monthly with 100 $\mu$g of antigen and bled (15 ml per bleed) at days seven and ten after boosting.

Monoclonal antibody specific for a given morphogen can be prepared as follows. A mouse is given two injections of *E. coli* produced OP-1 monomer. The first injection contains 100 $\mu$g of OP-1 in complete Freund's adjuvant and is given subcutaneously. The second injection contains 50 $\mu$g of OP-1 in incomplete adjuvant and is given intraperitoneally. The mouse then receives a total of 230 $\mu$g of OP-1 (amino acids 307–431 in SEQ ID NO:5) in four intraperitoneal injections at various times over an eight month period. One week, prior to fusion, both mice are boosted intraperitoneally with 100 $\mu$g of OP-1 (307–431) and 30 $\mu$g of the N-terminal peptide (Ser$_{293}$-Asn$_{309}$-Cys) conjugated through the added cysteine to bovine serum albumin with SMCC crosslinking agent. This boost was repeated five days (IP), four days (IP), three days (IP) and one day (IV) prior to fusion. The mouse spleen cells are then fused to myeloma (e.g., 653) cells at a ratio of 1:1 using PEG 1500 (Boeringer Mannheim), and the cell fusion is plated and screened for OP-1-specific antibodies using OP-1 (307–431) as antigen. The cell fusion and monoclonal screening then are according to standard procedures well described in standard texts widely available in the art.

20.3 Determination of Level of Nerve Trophic Factor

In a manner analogous to that described above, substances which stimulate production of nerve trophic factors can also be identified by the skilled artisan. See, e.g., Ebendal et al. (1991), *Plasticity and Regeneral of the Nervous System*, pp. 207–225 (Timeras et al., eds.; Plenum Press, N.Y.; Caswell (1993), 124 *Exp. Neurol.* 36, the teachings of both references being herein-incorporated by reference). Cells that are competent to produce a desired nerve trophic factor include, within their genetic material, a gene encoding the desired factor. This nerve trophic factor gene is preferably a cellular gene naturally present in the cells, but can also be a foreign gene introduced by standard genetic engineering techniques. The nerve trophic factor gene is in operative association with nucleic acid expression regulatory elements thereof, including but not necessarily limited to a promoter element. Thus, such cells, although not necessarily actively expressing the nerve trophic factor gene, are competent to express this gene when appropriately stimulated by a candidate nerve trophic factor stimulating agent. In the exemplary assay, the level of nerve trophic factor production is determined with and without incubating the cell in culture with the putative stimulating agent in order to assess the effects of the agent on the cell. This can be accomplished by detection of the nerve trophic factor either at the protein or RNA level. Classes of candidate compounds that can be tested for stimulating activity include but are not limited to those discussed above.

The invention can be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method for promoting dendrite outgrowth by a neuron, comprising contacting said neuron with a composition comprising a morphogen, wherein said morphogen comprises a dimeric protein having an amino acid sequence selected from:
 (1) a conserved C-terminal seven-cysteine skeleton at least about 60% identical or 70% homologous to the residues 38–139 of SEQ ID NO: 5;
 (2) generic sequence 3 (SEQ ID NO: 3) or generic sequence 4 (SEQ ID NO: 4);
 (3) generic sequence 5 (SEQ ID NO: 30) or generic sequence 6 (SEQ ID NO: 31); or
 (4) generic sequence OPX (SEQ ID NO: 29);
 wherein said morphogen promotes dendrite outgrowth in said neuron.

2. The method of claim 1, wherein said morphogen comprises residues 38–139 of SEQ ID NO: 5.

3. The method of claim 1, wherein said morphogen comprises the amino acid sequence of SEQ ID NO: 5.

4. The method of claim 1, wherein said morphogen comprises residues 38–139 of SEQ ID NO: 6.

5. The method of claim 1, wherein said morphogen comprises the amino acid sequence of SEQ ID NO: 6.

6. The method of claim 1, wherein said morphogen is a CBMP2 polypeptide.

7. The method of claim 6, wherein said CBMP2 polypeptide comprises the amino acid sequence of SEQ ID NO: 9.

8. The method of claim 6, wherein said CBMP2 polypeptide comprises the amino acid sequence of SEQ ID NO: 10.

9. The method of claim 1, wherein said morphogen is a BMP-6 polypeptide.

10. The method of claim 9, wherein said BMP-6 polypeptide comprises the amino acid sequence of SEQ ID NO: 28.

11. The method of claim 1, wherein said morphogen is a 60A polypeptide.

12. The method of claim 11, wherein said 60A polypeptide comprises the amino acid sequence of SEQ ID NO: 24.

13. The method of claim 1, wherein the composition includes NGF.

14. The method of claim 1, wherein the neurons are sympathetic neurons.

15. The method of claim 1, wherein said morphogen is human OP-1, mouse OP-1, human OP-2, mouse OP-2, BMP5, BMP6, Vgr-1, 60A, BMP2A, BMP-2B, DPP, Vgl, GDF-1, or BMP3.

16. The method of claim 1, wherein said morphogen is human OP-1, mouse OP-1, human OP-2, mouse OP-2, BMP5, BMP6, Vgr-1, 60A, BMP2A, BMP-2B, DPP, Vgl, or GDF-1.

17. The method of claim 1, wherein said morphogen is human OP-1, mouse OP-1, human OP-2, mouse OP-2, BMP5, BMP6, Vgr-1, 60A, BMP2A, BMP-2B, or DPP.

18. The method of claim 1, wherein said morphogen is human OP-1, mouse OP-1, human OP-2, mouse OP-2, BMP5, BMP6, Vgr- 1, 60A, BMP2A, or BMP-2B.

* * * * *